US012742764B2

(12) United States Patent
Cardone

(10) Patent No.: US 12,742,764 B2
(45) Date of Patent: Sep. 22, 2026

(54) METHODS FOR PREDICTING CANCER DRUG RESPONSIVENESS

(71) Applicant: Eutropics Pharmaceuticals, Inc., Cambridge, MA (US)

(72) Inventor: Michael Cardone, Dorchester, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 456 days.

(21) Appl. No.: 16/962,720

(22) PCT Filed: Jan. 18, 2019

(86) PCT No.: PCT/US2019/014208
§ 371 (c)(1),
(2) Date: Jul. 16, 2020

(87) PCT Pub. No.: WO2019/143947
PCT Pub. Date: Jul. 25, 2019

(65) Prior Publication Data

US 2020/0348280 A1 Nov. 5, 2020

Related U.S. Application Data

(60) Provisional application No. 62/772,368, filed on Nov. 28, 2018, provisional application No. 62/719,789, filed on Aug. 20, 2018, provisional application No. 62/618,786, filed on Jan. 18, 2018.

(51) Int. Cl.
*G01N 33/15* (2006.01)
*C07K 16/00* (2006.01)
*C07K 16/28* (2006.01)

(52) U.S. Cl.
CPC ........... *G01N 33/15* (2013.01); *C07K 16/005* (2013.01); *C07K 16/28* (2013.01); *C07K 2317/32* (2013.01); *G01N 2800/52* (2013.01)

(58) Field of Classification Search
None
See application file for complete search history.

(56) References Cited

U.S. PATENT DOCUMENTS 5,856,445 A 1/1999 Korsmeyer
5,955,593 A 9/1999 Korsmeyer
5,998,583 A 12/1999 Korsmeyer
6,165,732 A 12/2000 Korsmeyer et al.
6,258,540 B1 7/2001 Lo et al.
6,326,354 B1 12/2001 Gross et al.
7,026,456 B1 4/2006 Gately et al.
7,247,700 B2 7/2007 Korsmeyer et al.
7,723,469 B2 5/2010 Walensky et al.
7,829,662 B2 11/2010 Korsmeyer et al.
7,868,133 B2 1/2011 Korsmeyer et al.
7,871,769 B2 1/2011 Baker et al.
8,168,755 B2 5/2012 Cardone et al.
8,198,405 B2 6/2012 Walensky et al.
8,221,966 B2 7/2012 Letai
8,323,987 B2 12/2012 Threadgil et al.
8,652,469 B2 * 2/2014 Kavanaugh ............. A61P 19/00 424/130.1
8,796,418 B2 8/2014 Walensky et al.
8,889,632 B2 11/2014 Bernal et al.
9,273,099 B2 3/2016 Walensky et al.
9,464,115 B2 10/2016 Walensky et al.
9,527,896 B2 12/2016 Bernal et al.
9,540,674 B2 1/2017 Letai
9,856,303 B2 1/2018 Korsmeyer et al.
9,902,759 B2 2/2018 Korsmeyer et al.
2002/0177692 A1 11/2002 Bartel
2003/0073661 A1 4/2003 Matsuyama et al.
2003/0181404 A1 9/2003 Avraham et al.
2004/0241902 A1 12/2004 Letertre et al.
2005/0191696 A1 9/2005 Goldmakher et al.
2006/0183687 A1 8/2006 Cory et al.
2008/0104721 A1 5/2008 Barsova et al.
2009/0030005 A1 1/2009 Kamb et al.
2009/0280510 A1 11/2009 Cardone et al.
2010/0015058 A1 1/2010 Li et al.
2011/0008371 A1 1/2011 Michelson
2011/0071042 A1 3/2011 Kim et al.
2011/0154522 A1 6/2011 Korsmeyer et al.
2012/0225794 A1 9/2012 Cardone et al.
2012/0225851 A1 9/2012 Cardone et al.
2013/0079424 A1 3/2013 Gerber et al.

(Continued)

FOREIGN PATENT DOCUMENTS

CN 1583776 A 2/2005
WO WO 96/13614 A1 5/1996

(Continued)

OTHER PUBLICATIONS

Piche-Nicholas et al., MAbs. 2018; 10: 81-94. doi: 10.1080/19420862.2017.1389355 (Year: 2018).*

(Continued)

*Primary Examiner* — Christina M Borgeest
(74) *Attorney, Agent, or Firm* — Morgan, Lewis & Bockius LLP

(57) ABSTRACT

The present disclosure relates to compositions and methods of determining cancer cell sensitivity to treatment using antibodies that detect heterodimers comprising Bcl-2 proteins. The disclosure also provides methods for predicting a cancer patient's sensitivity to the cancer treatment.

8 Claims, 52 Drawing Sheets

Specification includes a Sequence Listing.

(56) References Cited

U.S. PATENT DOCUMENTS

2015/0301053 A1 10/2015 Pierceall et al.
2016/0178634 A1 6/2016 Cardone
2016/0222118 A1 8/2016 Chen et al.
2016/0273020 A1 9/2016 Pierceall et al.
2020/0392585 A1 12/2020 Dettman et al.

FOREIGN PATENT DOCUMENTS

WO WO 96/15263 A1 5/1996
WO WO 98/09643 A1 3/1998
WO WO 98/09980 A1 3/1998
WO WO 98/17682 A1 4/1998
WO WO 99/16787 A1 4/1999
WO WO 2000/06187 A2 2/2000
WO WO 2000/11162 A1 3/2000
WO WO 2002/05835 A2 1/2002
WO WO 2003/057158 A2 7/2003
WO WO 2004/022580 A2 3/2004
WO WO 2004/087887 A2 10/2004
WO WO 2005/044839 A2 5/2005
WO WO 2007/123791 A2 11/2007
WO WO 2008/021484 A2 2/2008
WO WO 2009/137664 A1 11/2009
WO WO 2010/093742 A1 8/2010
WO WO 2011/088137 A2 7/2011
WO WO 2012/122370 A2 9/2012
WO WO 2013/138702 A2 9/2013
WO WO 2013/170176 A2 11/2013
WO WO 2014/047342 A1 3/2014
WO WO 2015/017788 A1 2/2015
WO WO 2015/042249 A1 3/2015
WO WO 2016/154380 A1 9/2016
WO WO 2016/176288 A1 11/2016
WO WO 2016/176299 A1 11/2016
WO WO 2017/023753 A1 2/2017

OTHER PUBLICATIONS

Dronca et al., Immunotherapy, 2016; 8:12, 1351-1353, DOI: 10.2217/imt-2016-0100 (Year: 2016).*
Spanier et al., Nature Communications, 2016; 7: 11804 (Year: 2016).*
Lacombe et al., Leukemia (1997) 11, 1878-1886 (Year: 1997).*
International Search Report & Written Opinion, PCT. Application No. PCT/US19/14208, date May 24, 2019, 20 pages.
Adlard, et al., "Prediction of the response of colorectal cancer to systemic therapy," The Lancet Oncol. 2002, vol. 3, pp. 75-82.
Bodet, et al., "BH3-only protein Bik is involved in both apoptosis induction and sensitivity to oxidative stress in multiple myeloma," Br. J. Cancer, 2010, vol. 103, pp. 1808-1814.
Campbell, et al., "General properties and applications of monoclonal antibodies," Monoclonal Antibody Technology, 1984, pp. 1-32.
Certo, et al., "Mitochondria Primed by Death Signals Determine Cellular Addiction to Antiapoptotic BCL-2 Family Members," Cancel Cell, 2006, vol. 9, pp. 351-365.
Chonghaile, et al., "Mitochondrial Apoptotic Priming Measured by BH3 Profiling Regulates Clinical Response to chemotherapy in Myeloma and Acute Lymphoblastic Leukemia and Explains Therapeutic Index," Abstract 1142, 53rd 4SH Annual Meeting and Exposition, Dec. 10-13, 2011, American Society of Hematology. 2011, 2 pages.
Chonghaile, et al., "Pretreatment Mitochondrial Priming Correlates with Clinical Response to Cytotoxic chemotherapy," Science, 2011, Vo. 334, pp. 1129-1133, including supporting material (2011).
Cimmino, et al., "miR-15 and miR-16 induce apoptosis by targeting BCL2," PNAS, 2005, vol. 102, No. 39, p. 13944-13945.
Colman, "Effects of amino acid sequence changes on antibody-antigen interactions," Res. Immunol., 1994, vol. 145, pp. 33-36.
Davids, et al., "BH3 Profiling Demonstrates That Restoration of Apoptotic Priming Contributes to Increased Sensitivity o P13K Inhibition on Stroma-Exposed Chronic Lymphocytic Leukemia Cells," Blood, 2011, vol. 118, Abstract 974. 2 pages.
Del Gaizo Moore, et al., "BH3 profiling—measuring intergrated function of the mitochondrial apoptotic to predict mil fate decisions," Cancer Lett., 2013, vol. 332, vol. 2, pp. 202-205.
Del Gaizo Moore, et al., "Chronic lymphocytic leukemia requires BCL2 to sequester prodeath BIM, explaining sensitivity to BCL2 antagonist ABT-737," J. Clin. Invest., 2007, vol. 117, No. 1, pp. 112-121.
Deng, et al., "BH3 Profiling Identifies Three Distinct Classes of Apoptotic Blocks to Predict Response to ABT-737 and Conventional Chemotherapeutic Agents," Cancel Cell, 2007, vol. 12, pp. 171-185.
Foight, et al., "Designed BH3 Peptides with High Affinity and Specificity for Targeting Mcl-1 in Cells", ACS Chem Biol, 2014, vol. 9, pp. 1962-1968.
Hann, et al., "Therapeutic Efficacy of ABT-737, a Selective Inhibitor of BCL-2, in Small Cell Lung Cancer," Cancer Res., 2008, vol. 68, pp. 2321-2328.
International Search Report and Written Opinion, International Application No. PCT/US2016/013003, Mar. 28, 2016, 14 pages.
International Search Report and Written Opinion, International Application No. PCT/EP2008/056825, dated Oct. 1, 2008.
Karp, et al., "Sequenctial Flavopiridol, Cytosine Arabinoside, and Mitoxantrone: A Phase II Trial in Adults with Poor-Risk Acute Myelogenous Leukemia," Clin. Cancer Therapy, 2007, vol. 13, No. 15, pp. 4467-4473.
Kasper, et al., "Targeting MCL-1 sensitizes FLT3-ITD-positive leukemias to cytotoxic therapies," Blood Cancer J., 2012, vol. 2, 10 pages.
Kim, et al., "Alvocidib Potentiates the Acticitivity of Azacytidine in an MCL-1-Dependent Fashioin". Blood, 2015, vol. 126, vol. 23, 2 pages.
Letai, et al., "Antiapoptotic BCL-2 is required for maintenance of a model leukemia," Cancer Cell, 2004, vol. 6, pp. 241-249.
Letai, et al., "Diagnosing and exploiting cancer's addiction to blocks in apoptosis," Nat. Rev. Cancer, 2008, vol. 8, pp. 121-132.
Liu, et al. "The Structure of a Bcl-xLIBim Fragment Complex: Implications for Bim Function," Immunity, 2003, vol. 19, pp. 341-352.
Maccallum, et al., "Antibody-antigen Interactions: Contact Analysis and Binding Site Topography," J. Mol. Biol., 1996, vol. 262, pp. 732-745.
Miller, et al, "Therapeutic Strategies to Enhance the Anticancer Efficacy of Histone Deacetylase Inhibitors," J. of Biomed.and Biotech., 2011, vol. 2011, Article ID 514261, 17 pages.
Paoluzzi, et al., "The BH3-only mimetic ABT-737 synergizes the antineoplastic activity of proteasome inhibitors in ymphoid malignancies," Blood, 2008, vol. 112, pp. 2906-2916.
Paul, "Fundamental Immunology," 3rd Edition, Raven Press and New York, 1993, pp. 292-295.
Pode-Shakked, et al., "Developmental tumourigenesis: NCAM as a putative marker for the malignant renal stem/ progenitor cell population," J. Cell. Mol. Med., 2009, vol. 13, No. 88, pp. 1792-1808.
Pritzker, et al., "Cancer Biomarkers: Easier Said Than Done," Clin. Chem., 2002, vol. 48, No. 8, pp. 1147-1150.
Piercall, et al., "BH3 Profiling Discriminates Response to Cytarabine-Based Treatment of Acute Myelogenous Leukemia," Mol. Cancer Ther, 2013, vol. 12, No. 12, pp. 2940-2949.
Raychaudhuri, "Low probability Bid-Bax reaction generates heterogeneit in apoptosis resistance of cancer and cancer stem cells," Department of Biomed. 2011, 17 pages.
Rollins-Raval, et al., "The value of immunohistochemistry for CD14, CD123, CD33, myeloperoxidase and CD68R in the diagnosis of acute and chronic myelomonocytic leukaemias," Histopathology, 2012, vol. 60, pp. 933-942.
Rudikoff, et al., "Single amino acid substitution altering antigen-binding specificity," Proc. Natl. Acad. Sci. USA, 1982, vol. 19, pp. 1979-1983.
Sinicrope, et al., "Proapoptotic Bad and Bid Protein Expression Predict Survival in Stages II and III Colon Cancers," Clin. Canc. Res., 2008, vol. 14, No. 13, pp. 4128-4133.

(56) References Cited

OTHER PUBLICATIONS

Sinicrope, et al., "Prognostic Impact of Bim, Puma, and Noxa Expression in Human Colon Carcinomas," Clin. Canc. Res., 2008, vol. 14, No. 18, pp. 5810-5818.
Stewart, et al., "The MCL-1 BH3 Helix is an Exclusive MCL-1 inhibitor and Apoptosis Sensitizer," Nat. Chem. Biol., 2010, vol. 5, No. 8, pp. 595-601.
Taussig, et al., "Anti-CD38 antibody-mediated clearance of human repopulating cells masks the heterogeneity of eukemia-initiating cells," Blood, 2008, vol. 112, No. 3, pp. 568-575.
Thomenius, et al., "Using BH3 Profiling as a Predictive Indicator for Myeloma Patient Response to Bortezomib," Blood, 2011, vol. 118, No. 21, Abstract No. 3952. 3 pages.
Valencia, et al., "A new reliable fluorescence in situ hybridization method for identifying multiple specific cytogenetic abnormalities in acute myeloid leukemia," Leukemia & Lymphoma, 2010, vol. 51, No. 4, pp. 680-685.
Vo, "Mitchondrial Priming Determines Chemotherapeutic Response in Acute Myeloid Leukemia," Disseration, Harvard University, 2012, UMI No. 3514220, 119 pages.
Vo, et al., "Relative Mitochondrial Priming of Myeloblasts and Normal HCSs Detemines Chemotherapeutic Success in AML," Cell, 2012, Vo. 151, No. 2, pp. 344-355.
Weniger, et al., "Treatment-Induced Oxidative Stress and Cellular Antioxidant Capacity Determine Response to Bortezomib in Mantel Cell Lymphoma," Clin. Canc. Res., 2011, vol. 17, No. 15, pp. 5101-5112.
Zeng, et al., "Targeting of mTORC1/2 by the mTOR kinase inhibitor PP242 induces apoptosis in AML cells under conditions mimicking the bone marrow microenvironment", Blood, 2012, vol. 120, No. 13, pp. 2679-2689.

* cited by examiner

FIG. 1
Sequestered Epitope
Exposed Conformational Epitope
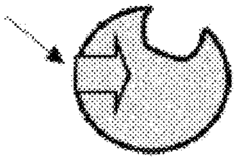
A. Multi-domain Anti-apoptotic Bcl-2 family protein
B. BH3 only Bcl-2 family protein
C. Bcl-2 family protein heterodimer Flow Cytometry Detection of HSBXB Antibody Staining Bcl-xL and HSBXB Sandwich ELISA (Capture with Bcl-xL)

FIG. 5

Step 1

Insert mAb32 L chain cDNA as an Xba I to Not I fragment into vector pdHLP-14.18-IL2, cut with the same enzymes, to create vector pdHLP-32 Vk.

Step 2

Insert mAb32 H chain cDNA as an Afl II to Xma I fragment into pdHLP-32 Vk, cut with the same enzymes, to create vector pdHLP-32g2a(D265A)

DNA sequences and peptide translation:

Light Chain (Xba I to Not I)

TCTAGAATGAAGTTGCCTGTTAGGCTGTTGGTGCTGATGTTCTGGATTCCTGCTTCCTTGAGCGACATCTTGCTGACTCAGT
CTCCAGCCATCCTGTCTGTGAGTCCAGGAGAAAGAGTCAGTTTCTCCTGCAGGGCCAGTCAGAGCATTGGCACAAGCATACA
CTGGTATCAGCAAAGAACAAATGGTTCTCCAAGGCTTCTCATAAAGTATGCTTCTGAGTCTATCTCTGGCATCCCTTCCAGG
TTTAGTGGCAGTGGATCAGGGACAGATTTTACTCTTAGCATCAACAGTGTGGAGTCTGAGGATATTGCAGATTATTACTGTC
AACAAAGTAATAGCTGGCCAACCACGTTCGGAGGGGGGACCAAGCTGGAAATAAAACGGGCTGATGCTGCACCAACTGTATC
CATCTTCCCACCATCCAGTGAGCAGTTAACATCTGGAGGTGCCTCAGTCGTGTGCTTCTTGAACAACTTCTACCCCAAAGACA
TCAATGTCAAGTGGAAGATTGATGGCAGTGAACGACAAAATGGCGTCCTGAACAGTTGGACCGATCAGGACAGCAAAGACA
GCACCTACAGCATGAGCAGCACCCTCACGTTGACTAAGGACGAGTATGAACGACATAACAGCTATACCTGTGAGGCCACTCA
CAAGACATCAACTTCAC CCATTGTCAAGAGCTTCAACAGGGGAGAGTGTTAGCAGCGGCCGC (SEQ ID NO: 9)

5'3' Frame 1

Met K L P V R L L V L Met F W I P A S L S D I L L T Q S P A I L S V S P G E R V S F S C R A S Q S I G T S I H W Y Q Q R T N
G S P R L L I K Y A S E S I S G I P S R F S G S G S G T D F T L S I N S V E S E D I A D Y Y C Q Q S N S W P T T F G G G T K L E
I K R A D A A P T V S I F P P S S E Q L T S G G A S V V C F L N N F Y P K D I N V K W K I D G S E R Q N G V L N S W T D Q
D S K D S T Y S Met S S T L T L T K D E Y E R H N S Y T C E A T H K T S T S P I V K S F N R G E C (SEQ ID NO: 10)

Heavy Chain D265A (Afl II to Xma I)

CTTAAGTCAGGTCCAGCTACAGCAGTCTGGACCTGAGCTGGTGAAGCCTGGGGCTTCAGTGAAGATATCCTGCAAGGCTTCTG
GCCACACCTTCACTGAACACTATATAAATTGGGTGAAGCAGAGGCCTGGACAGGGACTTGAGTGGATTGGATGGATTTTTCC
TGGAAGTGGTAGTACTTACTACAATGAGAAGTTCAAGGGCAAGGCCACACTTACTGTAGACAAATCCTCCAGCACAGCCTAC
ATGTTGCTCAGCAGCCTGACCTCTGAGGACTCTGCGGTCTATTTCTGTGCAAGAAGCTATAGTAACTTCTGGTTTGCTTACTG
GGGCCAAGGGACTCTGGTCACTGTCTCTGCCAAAACAACAGCCCCATCGGTCTATCCACTGGCCCCTGTGTGTGGAGATACAA
CTGGCTCCTCGGTGACTCTAGGATGCCTGGTCAAGGGTTATTTCCCTGAGCCAGTGACCTTGACCTGGAACTCTGGCTCCCTG
TCCAGTGGTGTGCACACCTTCCCAGCAGTCCTCCAGTCTGACCTCTACACCCTCAGCAGCTCAGTGACTGTAACCTCCAGCACC
TGGCCCAGCCAGTCCATCACCTGCAATGTGGCCCACCCGGCAAGCAGCACCAAGGTGGACAAGAAAATTGAGCCCAGAGGGCC
CACAATCAAGCCCTGTCCTCCATGCAAATGCCCAGCACCTAACCTCTTGGGTGGACCATCCGTCTTCATCTTCCCTCCAAAGA
TCAAGGATGTACTCATGATCTCCCTGAGCCCCATAGTCACATGTGTGGTGGTGGCTGTGAGCGAGGATGACCCAGATGTCCAG
ATCAGTTGGTTTGTGAACAACGTGGAAGTACACACAGCTCAGACACAAACCCATAGAGAGGATTACAACAGTACTCTCCGGG
TGGTCAGTGCCCTCCCCATCCAGCACCAGGACTGGATGAGTGGCAAGGAGTTCAAATGCAAGGTCAACAACAAAGACCTCCCA
GCGCCCATCGAGAGAACCATCTCAAAACCCAAAGGGTCAGTAAGAGTTCCACAGGTATATGTCTTGCCTCCACCAGAAGAAG
AGATGACTAAGAAACAGGTCACTCTGACCTGCATGGTCACAGACTTCATGCCTGAAGACATTTACGTGGAGTGGACCAACAA
CGGGAAAACAGAGCTAAACTACAAGAACACTGAACCAGTCCTGGACTCTGATGGTTCTTACTTCATGTACAGCAAGCTGAGA
GTGGAAAAGAAGAACTGGGTGGAAAGAAATAGCTACTCCTGTTCAGTGGTCCACGAGGGTCTGCACAATCACCACACGACTA
AGAGCTTCTCCCGGACCCCGGG (SEQ ID NO: 11)

Met L L S S L T S E D S A V Y F C A R S Y S N F W F A Y W G Q G T L V T V S A K T T A P S V Y P L A P V C G D T T G S S V
T L G C L V K G Y F P E P V T L T W N S G S L S S G V H T F P A V L Q S D L Y T L S S S V T V T S S T W P S Q S I T C N V A
H P A S S T K V D K K I E P R G P T I K P C P P C K C P A P N L L G G P S V F I F P P K I K D V L Met I S L S P I V T C V V V
A V S E D D P D V Q I S W F V N N V E V H T A Q T Q T H R E D Y N S T L R V V S A L P I Q H Q D W Met S G K E F K C K V
N N K D L P A P I E R T I S K P K G S V R V P Q V Y V L P P P E E E Met T K K Q V T L T C Met V T D F Met P E D I Y V E
W T N N G K T E L N Y K N T E P V L D S D G S Y F Met Y S K L R V E K K N W V E R N S Y S C S V V H E G L H N H H T T K
S F S R T P (SEQ ID NO: 12)

FIG. 5 (Continued)

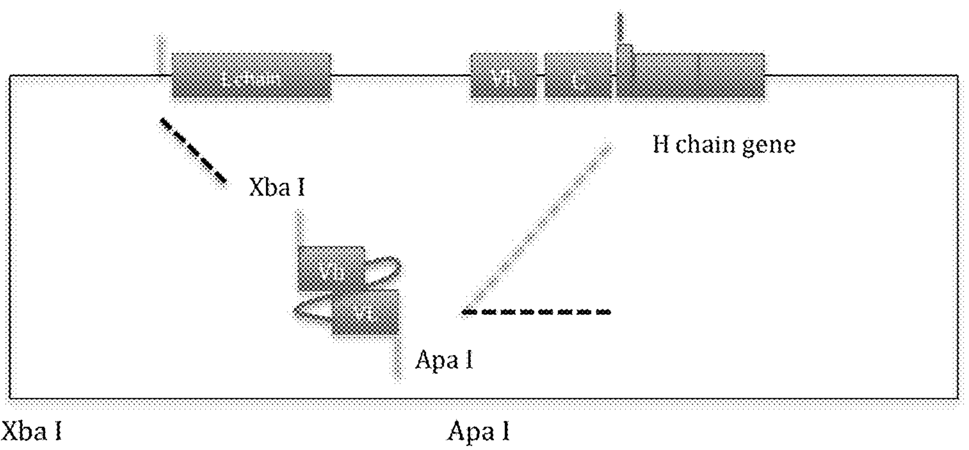

Light Chain Variable Region Amino Acid Sequence (SEQ ID NO:8):
DILLTQSPAILSVSPGERVSFSCRASQSIGTSIHWYQQRTNGSPRLLIKYASESISGIPSRFSG
SGSGTDFTLSINSVESEDIADYYCQQSNSWPTTFGGGTKLEIKRADAAPTVSIFPPSSEQLT
SGGASVVCFLNNFYPKDINVKWKIDGSERQNGVLNSWTDQDSKDSTYSMSSTLTLTKD
EYERHNSYTCEATHKTSTSPIVKSFNRGEC Heavy Chain Variable Region Amino Acid Sequence (SEQ ID NO: 7):
QVQLQQSGPELVKPGASVKISCKASGHTFTEHYINWVKQRPGQGLEWIGWIFPGSGSTY
YNEKFKGKATLTVDKSSSTAYMLLSSLTSEDSAVYFCARSYSNFWFAYWGQGTLVTVS
AKTTAPSVYPLAPVCGDTTGSSVTLGCLVKGYFPEPVTLTWNSGSLSSGVHTFPAVLQS
DLYT LSSSVTVTSSTWPSQSITCNVAHPASSTKVD FIG. 8
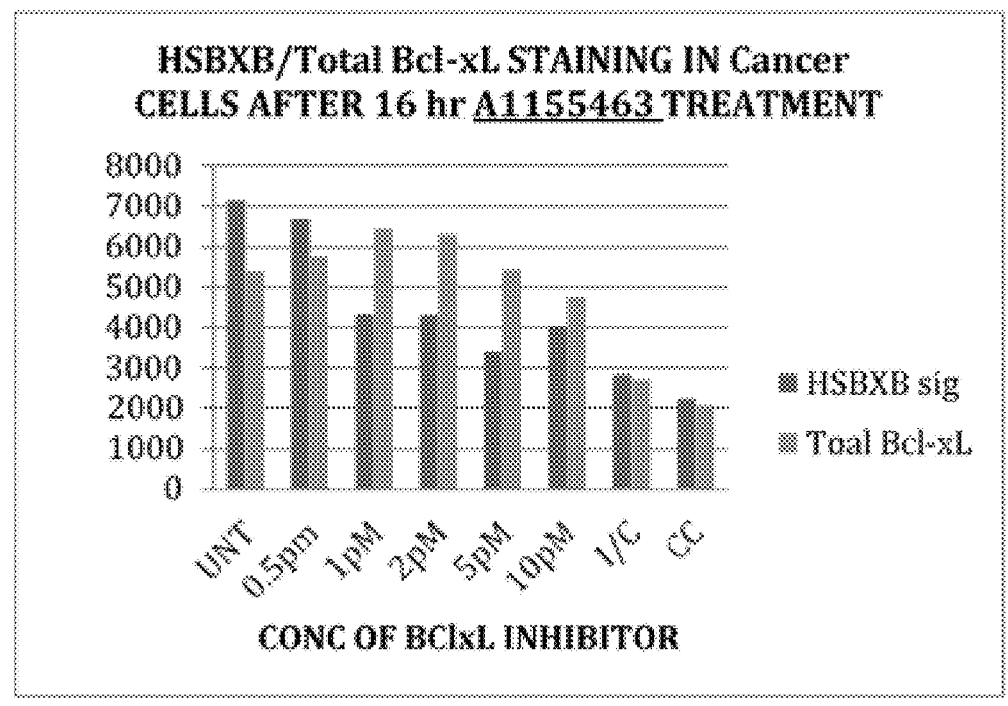
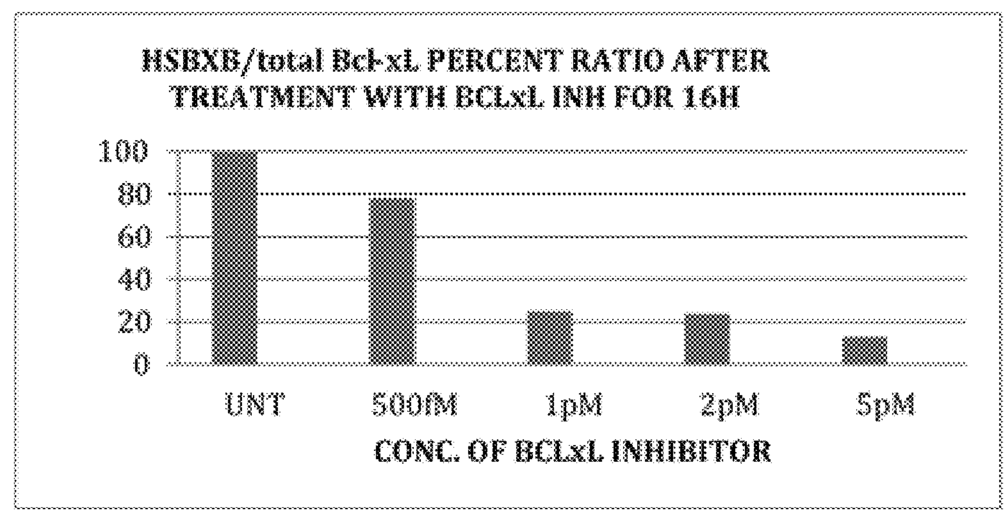

FIG. 9A

| AML patient | HRK PRIMING | HSBXB/ Total Bcl-xL |
|---|---|---|
| 1 | 0 | 30 |
| 2 | 5 | 5 |
| 3 | 16 | 37 |
| 4 | 17 | 34 |
| 5 | 46 | 40 |
| 6 | 61 | 100 |
| 7 | 74 | 80 |
| 8 | 82 | 100 |
| 9 | 84 | 96 |
| 10 | 99 | 100 |

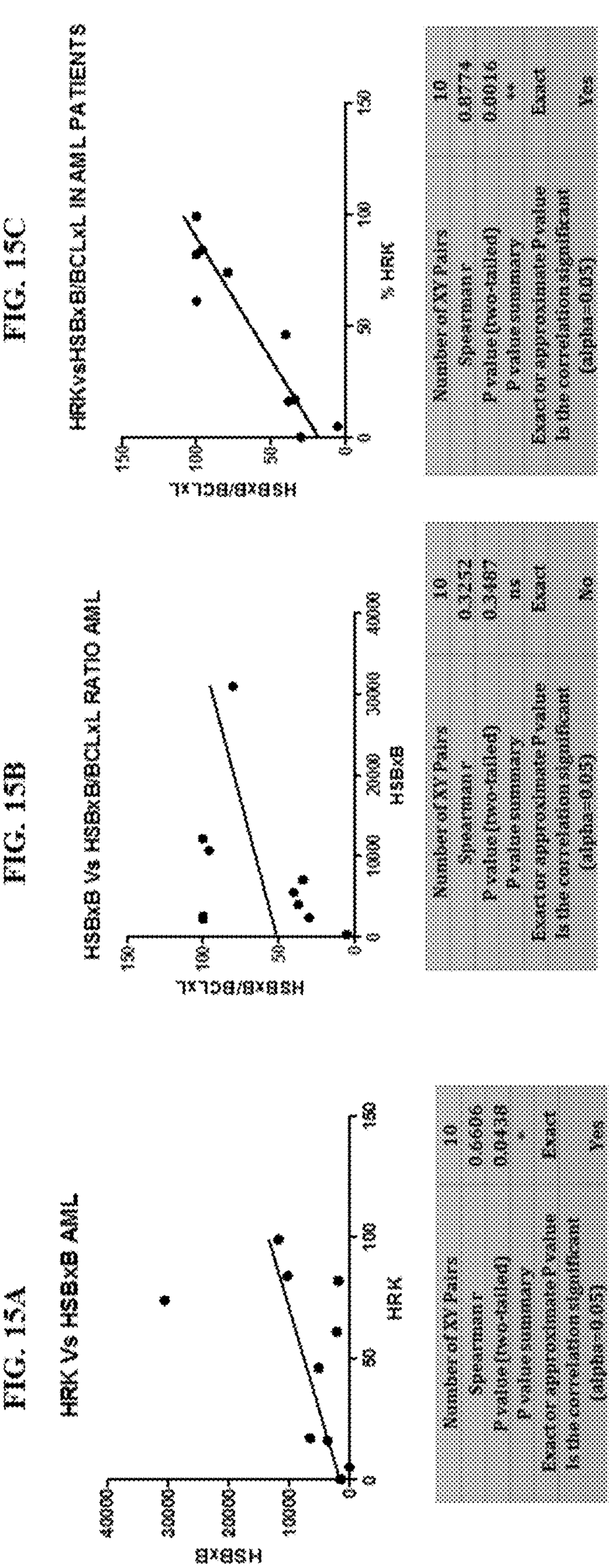
FIG. 15A
HRK Vs HSBxB AML
HSBxB
HRK
Number of XY Pairs 10
Spearman r 0.6606
P value (two-tailed) 0.0438
P value summary *
Exact or approximate P value Exact
Is the correlation significant (alpha=0.05) Yes
FIG. 15B
HSBxB Vs HSBxB/BCLxL RATIO AML
HSBxB/BCLxL
HSBxB
Number of XY Pairs 10
Spearman r 0.3252
P value (two-tailed) 0.3487
P value summary ns
Exact or approximate P value Exact
Is the correlation significant (alpha=0.05) No
FIG. 15C
HRKvsHSBxB/BCLxL IN AML PATIENTS
HSBxB/BCLxL
% HRK
Number of XY Pairs 10
Spearman r 0.8774
P value (two-tailed) 0.0016
P value summary **
Exact or approximate P value Exact
Is the correlation significant (alpha=0.05) Yes

HCC1937

| hcc1937 | EC50 (nM) |
|---|---|
| A1331852 | 46.97 |
| Selumetinib | 16310 |

BT-474

| bt474 | EC50 (nM) |
|---|---|
| A1331852 | 6539 |
| Selumetinib | NA |

FIG. 18
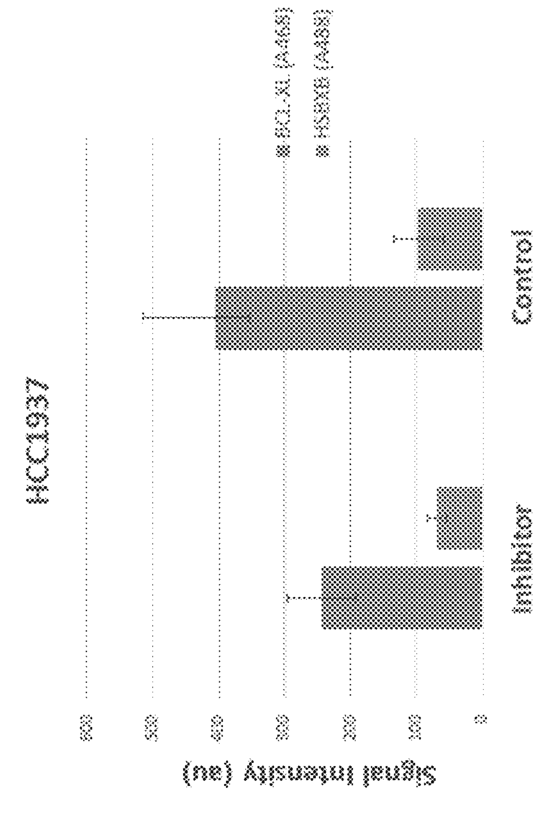
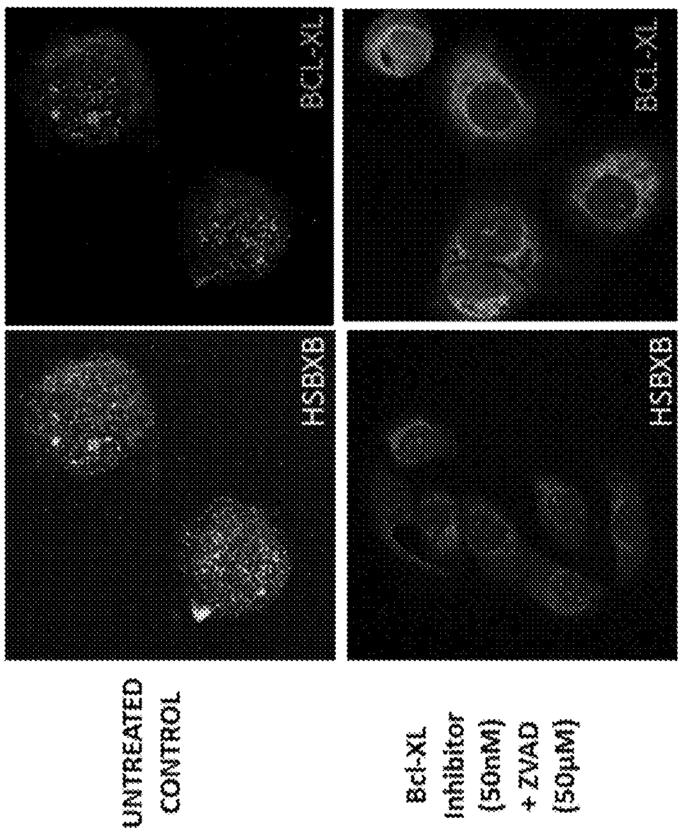

FIG. 27
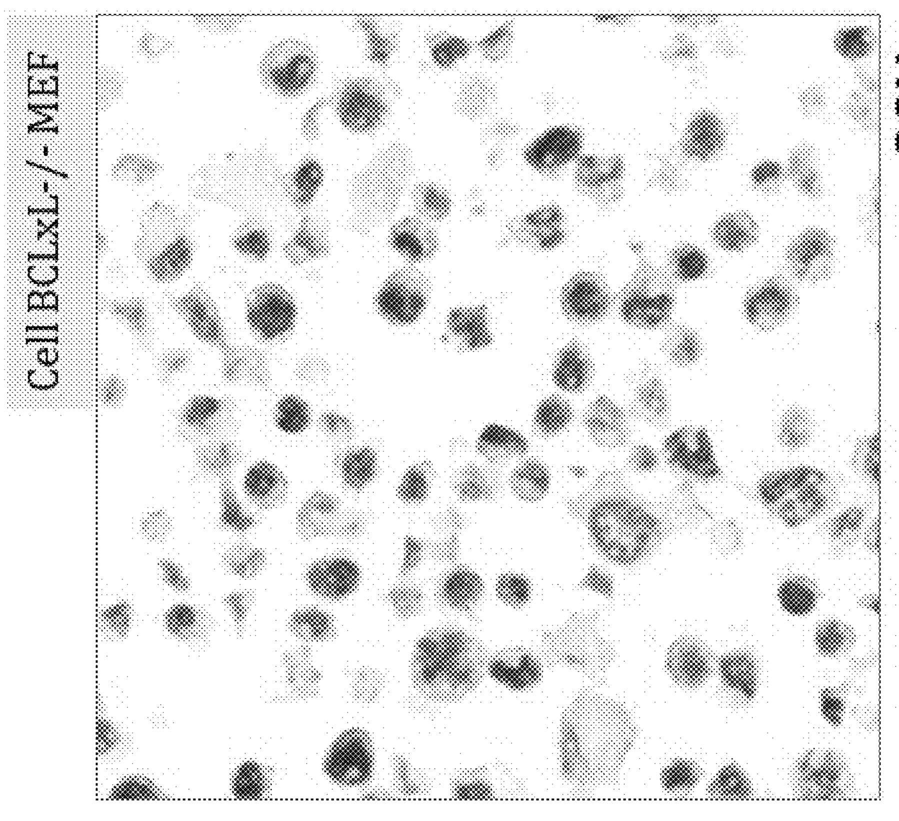
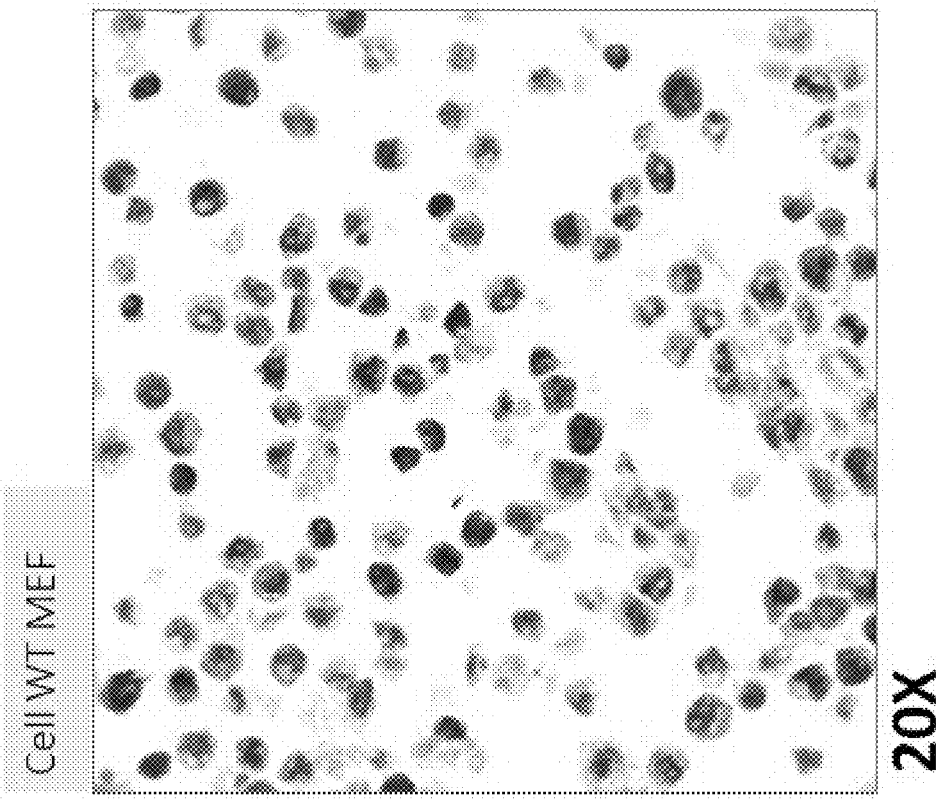

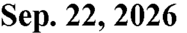
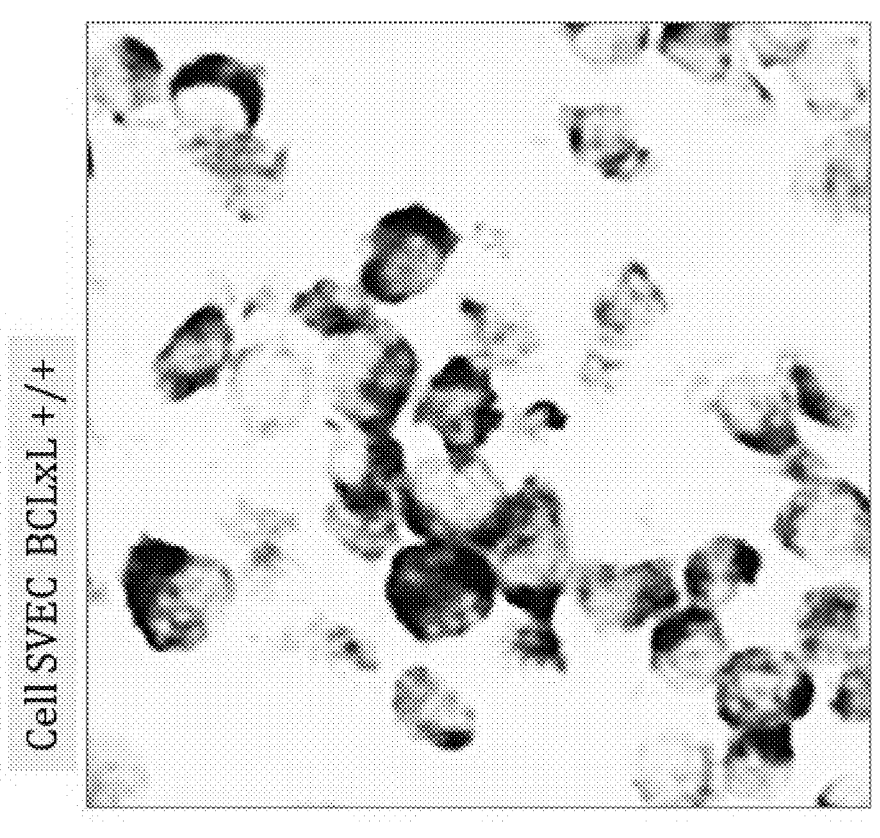
HSBxB: SG Dark Grey
BCLxL: DAB Brown
FIG. 32

FIG. 34

| CANCER TYPE | POS/NEG |
|---|---|
| Breast Ductal CA | 11/9 |
| Breast Medullary CA | 2/1 |
| Gastric Adenocarcinoma | 73/8 |
| Lung Oat Cell CA | 1/1 |
| Sarcomatoid CA of the Kidney | 1/1 |
| ARR-CS1 Human Breast CA Array | POS/NEG |
| Breast Ductal CA | 26/6 |
| Breast Medullary/Lobular CA | 3/1 |
| TOTAL BREAST CA from ARR: 91B & CS1 | POS/NEG |
| Breast Ductal CA | 37/15 |
| Breast Medullary/Lobular CA | 5/2 |

FIG. 35C

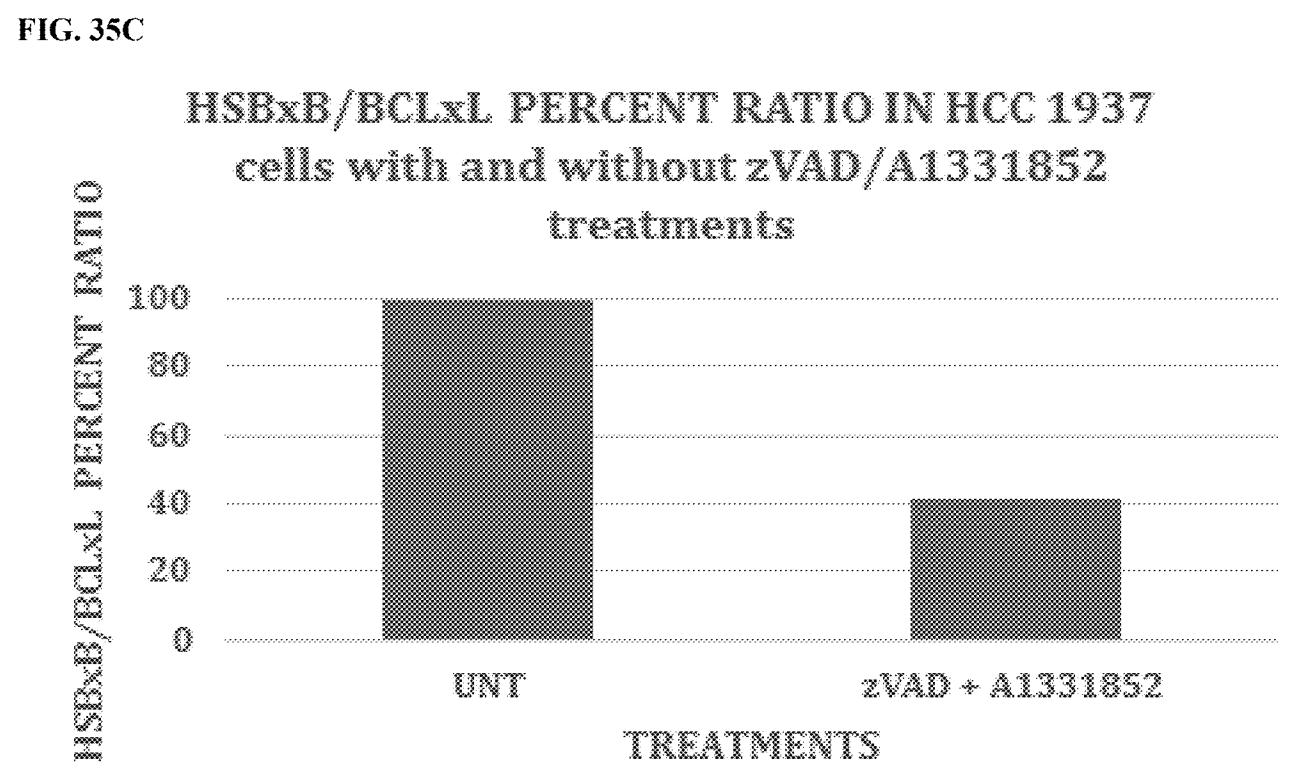

HSBxB/BCLxL PERCENT RATIO IN HCC 1937 cells with and without zVAD/A1331852 treatments HSBxB/BCLxL PERCENT RATIO 100
80
60
40
20
0

UNT zVAD + A1331852

TREATMENTS

METHODS FOR PREDICTING CANCER DRUG RESPONSIVENESS

FIELD OF THE DISCLOSURE

The present disclosure relates to compositions and methods of determining cancer cell sensitivity to treatment using antibodies that detect heterodimers comprising Bcl-2 proteins.

CROSS-REFERENCE TO RELATED APPLICATIONS

This application is a U.S. national stage application based on International Application No. PCT/US2019/014208, and claims priority to and the benefit of U.S. Provisional Application No. 62/772,368, filed Nov. 28, 2018, U.S. Provisional Application No. 62/719,789, filed Aug. 20, 2018, and U.S. Provisional Application No. 62/618,786, filed Jan. 18, 2018, the contents of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EUTR-018US_105444-5018_Sequence_Listing_ST25; date recorded: Mar. 27, 2024; 8,192 bytes in size).

BACKGROUND

Cancer continues to be a leading cause of death worldwide. There is a need in the field for more efficacious treatments of cancer. As numerous molecularly targeted agents are entering clinical trials, predictive testing is highly desirable. Specifically, selection of the proper patients for clinical trial enrollment and, upon approval, treatment, is a major driver for clinical development of new cancer therapies.

The intrinsic pathway of apoptosis is regulated at the level of the mitochondria where more than fifteen members of the B-cell lymphoma 2 (BCL-2) family of proteins interact. Many chemotherapeutic agents cause apoptosis, and the mechanism often involves changes in the levels and interactions of BCL-2 family members. The members of the Bcl-2 family share one or more of the four characteristic domains of homology entitled the Bcl-2 homology (BH) domains (BH1, BH2, BH3 and BH4).

BH3 profiling is a functional assay that measures tumor cell mitochondrial priming by measuring mitochondrial outer membrane permeabilization (MOMP) following exposure to a peptide-mimicking BH3 domains of BH3-only proteins. MOMP is measured indirectly by the fluorescent dye JC-1, which measures potential across the mitochondrial inner membrane. This potential rapidly degrades in response to MOMP. However, in practice, this sort of functional measurement based on JC-1 is hindered by difficulties in measuring a consistent fluorescent signal.

Further, direct measurement of the protein levels of individual BH3-only proteins, instead of a functional signal, is confounded by the fact that changes in these levels are not consistently correlated with sensitivity to the test anti-cancer agents being tested.

Additionally, combining the functional BH3 measurement with direct measurement of the protein levels of individual BH3-only proteins is complicated and not suited for solid tumor or fixed specimens.

Thus, there is a need for new compositions and methods that provide improved predictive testing for cancer treatment.

SUMMARY

Accordingly, the present disclosure is based, in part, on the discovery of several antibodies that each specifically bind to a Bcl-2 heterodimer (e.g., Bcl-xl/BIM-BH3 heterodimer). The disclosure further provides antibodies are useful for detecting a heterodimer comprising two B-cell lymphoma 2 (BCL-2) proteins in a solid tumor sample from a patient, and determining a ratio of the heterodimer to a reference value, the ratio being predictive of a patient's sensitivity to the cancer treatment. As such, the disclosed antibodies provide improved compositions and methods predictive testing for cancer treatment.

In some aspects, disclosed herein is a method for predicting a patient's sensitivity to a cancer treatment, comprising contacting a sample with an antibody or antibody format that recognizes a heterodimer comprising two B-cell lymphoma 2 (BCL-2) proteins, the sample being a specimen from a solid tumor of the patient; detecting a signal that indicates the amount of the heterodimer; and determining a ratio based on the amount of heterodimer present in the sample to a reference value, wherein the reference value comprises the amount of one of the BCL-2 protein monomers of the heterodimer in the sample, the ratio being predictive of a patient's sensitivity to the cancer treatment.

In another aspect, the present disclosure provides a method for predicting a patient's sensitivity to a cancer treatment, comprising: contacting a sample with an antibody or antibody format that recognizes a heterodimer comprising two B-cell lymphoma 2 (BCL-2) proteins and an antibody or antibody format that recognizes one of the BCL-2 protein monomers of the heterodimer, the sample being a specimen from a solid tumor of the patient; detecting a signal that indicates the amount of the heterodimer and the amount of the monomer; and determining a ratio based on the amount heterodimer to the amount of the monomer, the ratio being predictive of a solid tumor patient's sensitivity to the cancer treatment.

In some embodiments, the method further comprises administering a cancer treatment to the patient if the ratio is predictive of sensitivity to the cancer treatment.

In some embodiments, the method further comprises treating the patient with a reduced dose or less frequent and/or shortened regimen of the cancer treatment if the ratio is predictive of sensitivity to the cancer treatment.

In some embodiments, the method further comprises treating the patient with an increased dose or more frequent and/or prolonged regimen of the cancer treatment if the ratio is predictive of sensitivity to the cancer treatment.

In some embodiments, the method further comprises withholding cancer treatment to the patient if the ratio is predictive of a lack of sensitivity to the cancer treatment.

In some embodiments, the method further comprises treating the patient with a different cancer treatment if the ratio is predictive of a lack of sensitivity to the cancer treatment.

In some embodiments, the method further comprises comprising determining one or more clinical factors of the patient.

In some embodiments, the method further comprises classifying the patient for likelihood of clinical response to the cancer treatment based on one or more clinical factors of the patient.

In some embodiments, the method further comprises comparing the prediction of the patient's sensitivity to the cancer treatment with the likelihood of clinical response to the cancer treatment based on one or more clinical factors of the patient. The clinical factor can be one or more of age, cytogenetic status, performance, histological subclass, gender, and disease stage.

In some embodiments, the method further comprises measuring an additional biomarker selected from mutational status, single nucleotide polymorphisms, steady state protein levels, and dynamic protein levels.

In some embodiments, the method further comprises detecting the heterodimer by employing an immunohistochemistry (IHC), flow cytometry, or immunofluorescent method.

In some embodiments, the BCL-2 protein is an activator BH3 protein.

In some embodiments, the method further comprises an activator BH3 protein selected from BID and BIM.

In some embodiments, the BCL-2 protein is a sensitizer BH3 protein. In some embodiments, the sensitizer BH3 protein is selected from BAD, BIK, NOXA A, NOXA B, HRK, BMF, and PUMA.

In some embodiments, the BCL-2 protein is a multidomain pro-apoptotic protein. In some embodiments, multidomain pro-apoptotic protein is selected from BAX and BAK.

In some embodiments, the BCL-2 protein is a multidomain anti-apoptotic protein. In some embodiments, the multidomain anti-apoptotic protein is selected from BCL-2, BCL-XL, MCL-1, BCL-W, and BFL-1.

In some embodiments, the heterodimer comprises BCL2 and one of BID, BIM, BAD, BIK, PUMA, and BMF.

In some embodiments, the method provides a ratio of heterodimer to one of BCL2, BID, BIM, BAD, BIK, PUMA, and BMF monomer.

In some embodiments, the heterodimer comprises BCLXL and one of BID, BIM, BAD, BIK, HRK, PUMA, and BMF.

In some embodiments, the method provides a ratio of heterodimer to one of BCLXL, BID, BIM, BAD, BIK, HRK, PUMA, and BMF monomer.

In some embodiments, the heterodimer comprises BCLW and one of BID, BIM, BIK, PUMA, and BMF.

In some embodiments, the method provides a ratio of heterodimer to one of BCLW, BID, BIM, BIK, PUMA, and BMF monomer.

In some embodiments, the heterodimer comprises MCL1 and one of BID, BIM, BIK, NOXA A, NOXA B, PUMA, BAK, and BMF.

In some embodiments, the method provides a ratio of heterodimer to one of MCL1, BID, BIM, BIK, NOXA A, NOXA B, PUMA, and BMF monomer.

In some embodiments, the heterodimer comprises BFL1 and one of BID, BIM, NOXA A, NOXA B, and PUMA.

In some embodiments, the method provides a ratio of heterodimer to one of BFL1, BID, BIM, NOXA A, NOXA B, and PUMA monomer.

In some embodiments, the cancer treatment is a BH3 mimetic. The BH3 mimetic can be selected from BCL-2/BCL-XL specific ABT-737 and ABT-263 (navitoclax), Bcl-2 specific Venetoclax (Venclexta, ABT-199), MCL-1 specific S63845 and AMG176 and ADZ5991, BCL-XL specific A-1155463 and A1331852, BFL-1/MCL-1 specific EU5346 or combinations thereof.

In some embodiments, the cancer treatment is one or more of anti-cancer drugs, chemotherapy, antagonist of an anti-apoptotic protein, surgery, adjuvant therapy, and neoadjuvant therapy. The cancer treatment can be one or more of a SMAC mimetic, BH3 mimetic, proteasome inhibitor, histone deacetylase inhibitor, glucocorticoid, steroid, monoclonal antibody, antibody-drug conjugate, or thalidomide derivative.

In some embodiments, the cancer treatment blocks formation of the particular heterodimer detected.

In some embodiments, the cancer treatment perturbs formation of the particular heterodimer detected.

In some embodiments, the cancer treatment is a checkpoint inhibitor.

In some embodiments, the checkpoint inhibitor is an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2.

In some embodiments, the agent that targets PD-1 is an antibody or antibody format specific for PD-1, optionally selected from nivolumab, pembrolizumab, and pidilizumab.

In some embodiments, the agent that targets PD-L1 is an antibody or antibody format specific for PD-L1, optionally selected from atezolizumab, avelumab, durvalumab, and BMS-936559.

In some embodiments, the agent that targets CTLA-4 is an antibody or antibody format specific for CTLA-4, optionally selected from ipilimumab and tremelimumab.

In some embodiments, the sample is selected from a tumor biopsy, tissue biopsy, tumor resection, frozen tumor tissue specimen, lymph node, bone marrow, circulating tumor cells, cultured cells, a formalin-fixed paraffin embedded tumor tissue specimen, bronchoalveolar lavage, skin, hair, urine, and combinations thereof.

In some embodiments, the tumor biopsy is selected from a core biopsy, needle biopsy, surgical biopsy, and an excisional biopsy.

In some embodiments, the sample is an infiltrating lymphocyte of the patient.

In some embodiments, the solid tumor is selected from lung cancer, breast cancer, prostate cancer, melanoma, pancreatic cancer, kidney cancer, colon cancer, and ovarian cancer.

In some embodiments, the lung cancer is selected from non-small cell lung cancer (NSCLC) and small cell lung cancer (SCLC).

In some embodiments, the breast cancer is triple negative breast cancer.

In some embodiments, prostate cancer is androgen independent prostate cancer.

In some embodiments, the sensitivity is characterized by (a) the presence of apoptosis in the sample; (b) the presence of an anti-apoptotic Bcl-2 heterodimer in the sample, indicating the patient is sensitive to a drug that interferes with formation an anti-apoptotic Bcl-2 heterodimer; (c) genetic risk factors; family history; personal history; race and ethnicity; features of the certain tissues; various benign conditions (e.g. nonproliferative lesions); previous chest radiation; carcinogen exposure and the like.

In some embodiments, the method does not involve a functional readout of mitochondrial outer membrane permeabilization (MOMP).

In some embodiments, the method does not involve a dye-based detection of cell membrane potential.

In some embodiments, the antibody or antibody format is selected from one or more of a monoclonal antibody, polyclonal antibody, antibody fragment, Fab, Fab', Fab'-SH, F(ab')2, Fv, single chain Fv, diabody, linear antibody, bispecific antibody, multispecific antibody, chimeric antibody, humanized antibody, human antibody, and a fusion protein comprising the antigen-binding portion of an antibody.

In some embodiments, the antibody or antibody format recognizes a heterodimer of BCL2 and one of BID, BIM, BAD, BIK, PUMA, and BMF.

In some embodiments, the antibody or antibody format recognizes a heterodimer of BCLXL and one of BID, BIM, BAD, BIK, HRK, PUMA, and BMF.

In some embodiments, the antibody or antibody format recognizes a heterodimer of BCLW and one of BID, BIM, BIK, PUMA, and BMF.

In some embodiments, the antibody or antibody format recognizes a heterodimer of MCL1 and one of BID, BIM, BIK, NOXA A, NOXA B, PUMA, BAK, and BMF.

In some embodiments, the antibody or antibody format recognizes a heterodimer of BFL1 and one of BID, BIM, NOXA A, NOXA B, and PUMA.

In some embodiments, the antibody or antibody format comprises: (i) a heavy chain variable region comprising heavy chain CDR1, CDR2, and CDR3 sequences, wherein the heavy chain CDR1 sequence is GHTFTEHYIN (SEQ ID NO: 1), the heavy chain CDR2 sequence is WIFPGSGSTYYNEKFKG (SEQ ID NO: 2); and the heavy chain CDR3 sequence is SYSNFWFAY (SEQ ID NO: 3); and (ii) a light chain variable region comprising light chain CDR1, CDR2, and CDR3 sequences, wherein the light chain CDR1 sequence is RASQSIGTSIH (SEQ ID NO: 4), the light chain CDR2 sequence is KYASESIS (SEQ ID NO: 5), and the light chain CDR3 sequence is QQSNSWPTT (SEQ ID NO: 6).

In some embodiments, the antibody or antibody format further comprises variable region framework (FW) sequences juxtaposed between the CDRs according to the formula (FW1)-(CDR1)-(FW2)-(CDR2)-(FW3)-(CDR3)-(FW4), wherein the variable region FW sequences in the heavy chain variable region are heavy chain variable region FW sequences, and wherein the variable region FW sequences in the light chain variable region are light chain variable region FW sequences.

In some embodiments, the variable region FW sequences are human.

In some embodiments, the antibody or antibody format further comprises a human heavy chain and light chain constant regions.

In some embodiments, the constant regions are selected from the group consisting of human IgG1, IgG2, IgG3, and IgG4.

In some embodiments, the antibody or antibody format comprises: (i) a heavy chain variable region sequence comprising the amino acid sequence set forth in SEQ ID NO: 7 or the amino acid sequence of SEQ ID NO: 7 with no more than 10 total amino acid substitutions; and (ii) a light chain variable region sequence comprising the amino acid sequence of SEQ ID NO: 8 or the amino acid sequence of SEQ ID NO: 8 with no more than 10 total amino acid substitutions.

In some embodiments, the antibody or antibody format comprises an amino acid sequence having at least 90%, or 93%, or 95%, or 97%, or 98% identity with SEQ ID NO: 7 and/or SEQ ID NO. 8.

In some embodiments, the likelihood of clinical response is defined by the following equation:

$$\%\ \text{Priming} = \left[100 * \left(\frac{DMSO\ AUC - Peptide_1 AUC}{DMSO\ AUC - CCCP_{avg} AUC}\right)\right] Peptide_1 + \left[100 * \left(\frac{DMSO\ AUC - Peptide_2 AUC}{DMSO\ AUC - CCCP_{avg} AUC}\right)\right] Peptide_2 + \ldots / (n\ \text{peptides})$$

wherein:

the AUC (area under a curve) is a sum of fluorescence measurements established by homogenous time-resolved fluorescence (HTRF) or mean signal intensity from fluorescence activated cell sorting (FACS), wherein the signal intensity is a single time point measurement that occurs between about 5 min and about 300 min after the start of priming;

the DMSO (Dimethyl sulfoxide) comprises a baseline negative control for either an area under a curve or a signal intensity;

the CCCP (Carbonyl cyanide m-chlorophenyl hydrazone) is a chemical inhibitor of oxidative phosphorylation and comprises an effector of protein synthesis by serving as uncoupling agent of the proton gradient established during the normal activity of electron carriers in the electron transport chain in the mitochondria, and the CCCP comprises a baseline positive control; and the Peptide is one or more BH3 domain peptides, wherein (n) is normalized with the average number of replicates of the DMSO and CCCP controls.

In some embodiments, in combination with the preceding equation, the one or more clinical factors are selected to increase specificity and/or sensitivity of the BH3 profile for association with clinical response.

In some embodiments, the likelihood of clinical response is defined by a simplified form of the preceding equation, as shown here:

$$\%\ \text{Priming} = \left[100 * \left(\frac{DMSO_{avg} AUC - Peptide_n AUC}{DMSO_{avg} AUC - CCCP_{avg} AUC}\right)\right]$$

wherein:

the AUC (area under a curve) is a sum of fluorescence measurements established by homogenous time-resolved fluorescence (HTRF) or mean signal intensity from fluorescence activated cell sorting (FACS), wherein the signal intensity is a single time point measurement that occurs between about 5 min and about 300 min after the start of priming;

the DMSO (Dimethyl sulfoxide) comprises a baseline negative control for either an area under a curve or a signal intensity;

the CCCP (Carbonyl cyanide m-chlorophenyl hydrazone) is a chemical inhibitor of oxidative phosphorylation and comprises an effector of protein synthesis by serving as uncoupling agent of the proton gradient established during the normal activity of electron carriers in the electron transport chain in the mitochondria, and the CCCP comprises a baseline positive control; and the Peptide is one or more BH3 domain peptides, wherein (n) is normalized with the average number of replicates of the DMSO and CCCP controls.

In some embodiments, in combination with the preceding equation, the one or more clinical factors are selected to increase specificity and/or sensitivity of the BH3 profile for association with clinical response.

In one aspect, the present disclosure provides a method for predicting a patient's responsiveness to a checkpoint inhibitor in a sample, comprising measuring the amount of a Mcl-1/Bim or a BCLXL/Bim heterodimer, wherein the sample comprises an infiltrating lymphocyte population from a solid tumor.

In some embodiments, the checkpoint inhibitor is an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2.

In some embodiments, the agent that targets PD-1 is an antibody or antibody format specific for PD-1, optionally selected from nivolumab, pembrolizumab, and pidilizumab.

In some embodiments, the agent that targets PD-L1 is an antibody or antibody format specific for PD-L1, optionally selected from atezolizumab, avelumab, durvalumab, and BMS-936559.

In some embodiments, the agent that targets CTLA-4 is an antibody or antibody format specific for CTLA-4, optionally selected from ipilimumab and tremelimumab.

In one aspect, the present disclosure provides a composition comprising an antibody or antibody format comprising: (i) a heavy chain variable region comprising heavy chain CDR1, CDR2, and CDR3 sequences, wherein the heavy chain CDR1 sequence is GHTFTEHYIN (SEQ ID NO: 1), the heavy chain CDR2 sequence is WIFPGSGSTYYNEKFKG (SEQ ID NO: 2); and the heavy chain CDR3 sequence is SYSNFWFAY (SEQ ID NO: 3); and (ii) a light chain variable region comprising light chain CDR1, CDR2, and CDR3 sequences, wherein the light chain CDR1 sequence is RASQSIGTSIH (SEQ ID NO: 4), the light chain CDR2 sequence is KYASESIS (SEQ ID NO: 5), and the light chain CDR3 sequence is QQSNSWPTT (SEQ ID NO: 6).

In some embodiments, the present disclosure provides a composition comprising an antibody or antibody format having the sequence of SEQ ID NO: 1, but with four or fewer amino acid substitutions, or with three or fewer amino acid substitutions, or with two or fewer amino acid substitutions, or with one amino acid substitution.

In some embodiments, the present disclosure provides a composition comprising an antibody or antibody format having the sequence of SEQ ID NO: 2, but with four or fewer amino acid substitutions, or with three or fewer amino acid substitutions, or with two or fewer amino acid substitutions, or with one amino acid substitution.

In some embodiments, the present disclosure provides a composition having the sequence of an antibody or antibody format comprising SEQ ID NO: 3, but with four or fewer amino acid substitutions, or with three or fewer amino acid substitutions, or with two or fewer amino acid substitutions, or with one amino acid substitution.

In some embodiments, the present disclosure provides a composition comprising an antibody or antibody format having the sequence of SEQ ID NO: 4, but with four or fewer amino acid substitutions, or with three or fewer amino acid substitutions, or with two or fewer amino acid substitutions, or with one amino acid substitution.

In some embodiments, the present disclosure provides a composition comprising an antibody or antibody format having the sequence of SEQ ID NO: 5, but with four or fewer amino acid substitutions, or with three or fewer amino acid substitutions, or with two or fewer amino acid substitutions, or with one amino acid substitution.

In some embodiments, the present disclosure provides a composition comprising an antibody or antibody format having the sequence of SEQ ID NO: 6, but with four or fewer amino acid substitutions, or with three or fewer amino acid substitutions, or with two or fewer amino acid substitutions, or with one amino acid substitution.

In some embodiments, the antibody or antibody format further comprises variable region framework (FW) sequences juxtaposed between the CDRs according to the formula (FW1)-(CDR1)-(FW2)-(CDR2)-(FW3)-(CDR3)-(FW4), wherein the variable region FW sequences in the heavy chain variable region are heavy chain variable region FW sequences, and wherein the variable region FW sequences in the light chain variable region are light chain variable region FW sequences.

In some embodiments, the variable region FW sequences are human.

In some embodiments, the antibody or antibody format further comprises a human heavy chain and light chain constant regions.

In some embodiments, the constant regions are selected from the group consisting of human IgG1, IgG2, IgG3, and IgG4.

In some embodiments, the antibody or antibody format comprises: (i) a heavy chain variable region sequence comprising the amino acid sequence set forth in SEQ ID NO: 7, or the amino acid sequence set forth in SEQ ID NO: 7 with no more than 10 total amino acid mutations selected from one or more of amino acid substitutions, amino deletions, and amino acid additions; and (ii) a light chain variable region sequence comprising the amino acid sequence set forth in SEQ ID NO: 8, or the amino acid sequence set forth in SEQ ID NO: 8 with no more than 10 total amino acid mutations selected from one or more of amino acid substitutions, amino deletions, and amino acid additions.

In some embodiments, the antibody or antibody format comprises an amino acid sequence having at least 90%, or 93%, or 95%, or 97%, or 98% identity with SEQ ID NO: 7 and/or SEQ ID NO. 8.

In some embodiments, the present disclosure provides a polynucleotide comprising a nucleic acid sequence encoding the antibody or antibody fragment as disclosed herein. In some embodiments, a vector comprising the polynucleotide provided; in some embodiments, a host cell comprising the vector is provided.

In some aspects, the present disclosure provides a pharmaceutical composition comprising the antibody or antibody format of any of the antibodies disclosed herein and a pharmaceutically acceptable excipient.

In some aspects, the present disclosure provides a method of generating a heterodimer antibody, comprising: (a) immunizing a subject (e.g., a human, a monkey, a mouse, a rat, or hamster) with a heterodimer induced conformation antigen; (b) isolating from the subject a splenic B cell producing the IgG recognizing the heterodimer induced antigen; (c) passing the splenic B cell onto a magnetic column for negative selection, wherein the magnetic column for negative selection is coated with a recombinant fusion protein containing one monomer of the heterodimer; (d) collecting the flow through of the splenic B cells from the magnetic column for negative selection, and passing the flow through onto a magnetic column for positive selection; wherein the magnetic column for positive selection is coated with the heterodimer antigen; (e) eluting and collecting the splenic B cells bound to the magnetic column for positive selection; (f)

culturing the collected cells in a B-cell media; and (g) isolating the heterodimer specific antibody from the cultured cells, thereby generating a heterodimer antibody. In some embodiments, the heterodimer antigen is of BCL2 and one of BID, BIM, BAD, BIK, PUMA, and BMF. In some embodiments, the heterodimer antigen is of BCLXL and one of BID, BIM, BAD, BIK, HRK, PUMA, and BMF. In some embodiments, the heterodimer antigen is of BCLW and one of BID, BIM, BIK, PUMA, and BMF. In some embodiments, the heterodimer antigen is of MCL1 and one of BID, BIM, BIK, NOXA A, NOXA B, PUMA, BAK, and BMF. In some embodiments, the heterodimer antigen is of BFL1 and one of BID, BIM, NOXA A, NOXA B, and PUMA. In some embodiments, the one monomer of the heterodimer is selected from BCL2, BID, BIM, BAD, BIK, PUMA, BMF, BCLXL, BCLW, and MCL1. In some embodiments, the one monomer of the heterodimer is MCL1. In some embodiments, the one monomer of the heterodimer is BIM. In some embodiments, the heterodimer is selected from BCL2 and one of BID, BIM, BAD, BIK, PUMA, and BMF. In some embodiments, the heterodimer is selected from BCLXL and one of BID, BIM, BAD, BIK, HRK, PUMA, and BMF. In some embodiments, the heterodimer is selected from BCLW and one of BID, BIM, BIK, PUMA, and BMF. In some embodiments, the heterodimer is selected from MCL1 and one of BID, BIM, BIK, NOXA A, NOXA B, PUMA, BAK, and BMF. In some embodiments, the heterodimer is selected from BFL1 and one of BID, BIM, NOXA A, NOXA B, and PUMA. In some embodiments, the heterodimer is selected from BCL2, BID, BIM, BAD, BIK, PUMA, BMF, BCLXL, BCLW, and MCL1.

The details of one or more examples of the disclosure are set forth in the description below. Other features or advantages of the present disclosure will be apparent from the following drawings, detailed description of several examples, and also from the appended claims. The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

DESCRIPTION OF THE DRAWINGS

FIG. 1 is an image showing how an immunogen may be used to make the heterodimer selective monoclonal antibody. There is a conformational change of a multidomain Bcl-2 protein induced by dimerization with a BH3-only Bcl-2 protein that is the targeted epitope.

In FIG. 4A, cells were incubated on ice for three hours, and then washed and incubated with HSBXB antibody or Bcl-xL antibody at 10 ug/ml for 20 minutes, washed, and then stained with a secondary Alexa488-conjugated goat anti-mouse antibody. Signals were corrected to IgG-2A isotype or secondary alone control. For each series, the left bar is the HSBXB antibody, and the right bar is the isotype control. In FIG. 4B, Hrk-BH3 signal in mitochondrial profiling of three cell lines was plotted against normalized HSBXB FACS signal. FIG. 4C shows the anti-Bcl-xL capture of Bcl-xL-Bim complex from cells lysed with RIPA (Thermo Fisher Scientific). For each series, the left bar is AHR77 cell line, and the right bar is the Molm-13 cell line. The captured complex was then probed with HSBXB or Bcl-xL. In FIG. 4D, SKBR3 cells were fixed in 2% PFA and stained with HSBXB (magenta) and Bcl-xL (Alexa 488).

FIG. 5 is an image showing the monoclonal antibody cloning steps, the expression vector used to produce the HSBXB antibody, the cloning strategy, the amino acid sequences of the Heavy chain variable region (SEQ ID NO. 7) and Light chain variable region (SEQ ID NO: 8), as well as the complementarity determining regions (CDRs) of the Heavy chain variable region and Light chain variable region (highlighted grey).

FIG. 7A shows IHC staining on breast section 0040-3 of patient 21 using HBSXB clone 32 (40× magnification). FIG. 7B shows IHC staining on breast section 0040-3 of patient 21 using the control antibody (40× magnification). FIG. 7C shows IHC staining on breast section 0020-3 of patient 14 using HBSXB clone 32 (40× magnification). These data show that Bcl-xl-Bim heterodimer can be used to identify priming in adherent samples and direct therapeutic interventions based on results.

FIG. 8 consists of two graphs that show how the Bcl-xL selective BH3 mimetic (A1155463) shifts the HSBXB heterodimer signal detected in cancer cells. For each series, the left bar is HSBXB signal and the right bar is total Bcl-xL. The data also shows that cells treated with a sub-lethal dose of A1155463 lose signal after 16 hours (bottom graph). The term "I/C" on the x-axis of the graph refers to "isotype control," and the term "CC" on the x-axis of the graph refers to the non-stained or "clean control." The signal was detected using Flow Cytometry.

FIG. 9A and FIG. 9B show the benchmarking of HSBXB/total Bcl-xL signal to BH3 profiling with Bcl-xL specific Hrk peptide readout of biopsied AML Blast cells. In FIG. 9A, AML patient samples were BH3 profiled. The Blast cell population showed Hrk priming (response to the Hrk BH3 peptide that was selective for Bcl-xL). In parallel AML patient samples were fixed and stained with the FITC labeled HSBHB antibody and the Cy5 labeled Bcl-xL antibody. The Blast cell gated signal was resolved on Flow Cytometry (FACS). The ratio of the HSBXB/total Bcl-xL was calculated and compared to the Hrk readout from the BH3 profiled sample. In FIG. 9B, the HSBXB detected heterodimer/total Bcl-xL signal ratio was plotted against the Hrk peptide generated signal from the AML patient samples as described in FIG. 9A.

In FIG. 10A, FIG. 10B, and FIG. 10C, the NOXA % priming (y-axis) indicates Mcl-1 dependency. While bone marrow NOXA priming is highly associated with clinical response (CR), samples from the peripheral blood are not associated with CR. On the x-axis of each graph, NR indicates "non-responder".

In FIG. 11A, the FLAM tx response positively correlates to Noxa+Bad priming in BM (p-value=0.049). In FIG. 11B, the FLAM tx response negatively correlates to Noxa+Bad priming and revealed dependencies in PB (p-value=0.0005). In FIG. 11C, there was a higher correlation observed with the Noxa/Bad priming ratio in BM (6-fold differences, p-value=0.002).

In FIG. 12A, the ratio of HSBXB/Bcl-xL signal was correlated with HRK priming in AML patient samples (p-value=0.0105). In FIG. 12B, the ratio of HSBXB/Bcl-xL signal was correlated with HRK priming in CLL patient samples (p-value=0.0003). In FIG. 12C, pretreatment with HRK signals of this patient group correlated with alvocidib response. On the x-axis of FIG. 12C, "PR" refers "partial response," and "PD" refers to progressive disease.

In FIG. 13A, the Bcl-xL-protein was bound ELISA plates. Bim BH3 peptide was added or not, and the HSBXB antibody was used to detect the complex. In FIG. 13B, the Bcl-xL-GST/BIM BH3 heterodimer was bound to Glutathione-coated ELISA plates and treated with ABT-263 (navitoclax), and a HSBXB signal was detected.

In FIG. 14A, human seminal endothelial vesicle cells overexpressing ectopic Bcl-xL and Bim (SEV-Bcl-xL-Bim[ref]) were treated with A-1155463 at the indicated concentrations for 2 hours in semi-permeabilized cells, fixed, and then fixed with HSBXB or Bcl-xL antibody corrected to IgG-2A isotype. The ratio of the signals (y-axis) were collected flow cytometry. In FIG. 14B, intact SEV-Bcl-xL/Bim cells were treated with A-1155463 for 16 hours, fixed and stained as in FIG. 14A. The ratio of HSBXB and Bcl-xL signal was calculated as a percentage as shown below:

$$\%\ HSBXB \text{ determined } Bcl\text{-}xL/BIM \text{ priming} = \left[\frac{(\text{Normalized } HSBXB)}{(\text{Normalized } Bcl\text{-}xL)}\right] \times 100\%$$

Figures 14A, 14B, 14C:
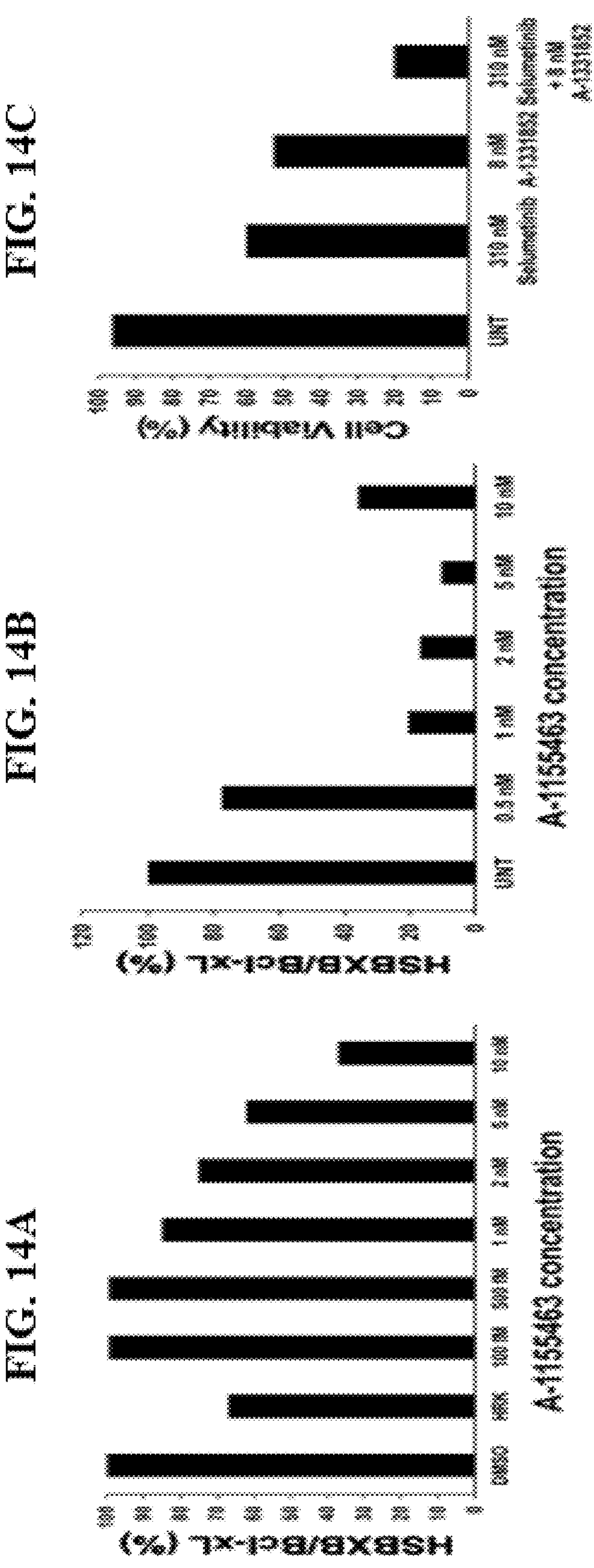
FIG. 14A, FIG. 14B, and FIG. 14C are graphs showing that the HSBXB signal shifts in response to a Bcl-xL selective BH3 mimetic when treated with A-1155463.

In FIG. 14C, SKBR3 cell treated with A-1155463, with or without MEK inhibitor, selumetenib.

FIG. 15A, FIG. 15B, and FIG. 15C are graphs showing the correlation of percent HRK versus HSBXB/BCLXL in AML patient samples.

Figure 16A:
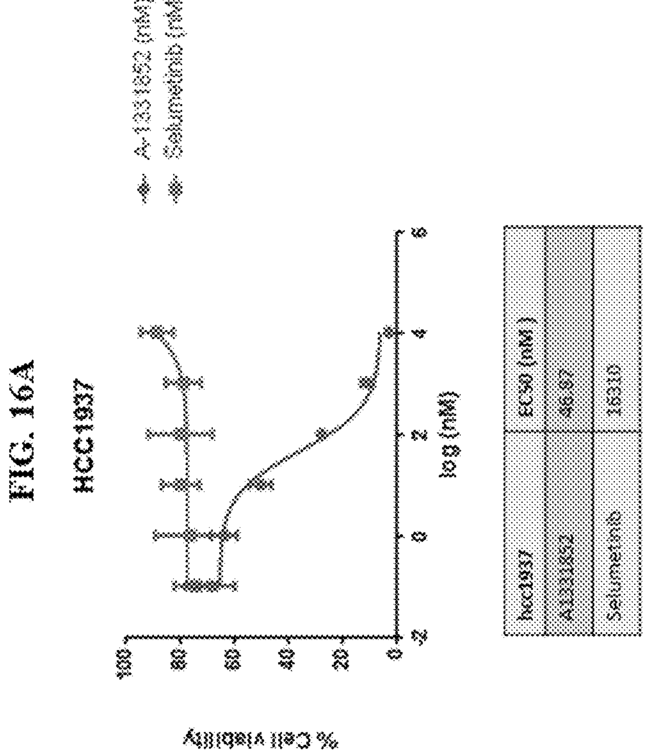
Figure 16B:
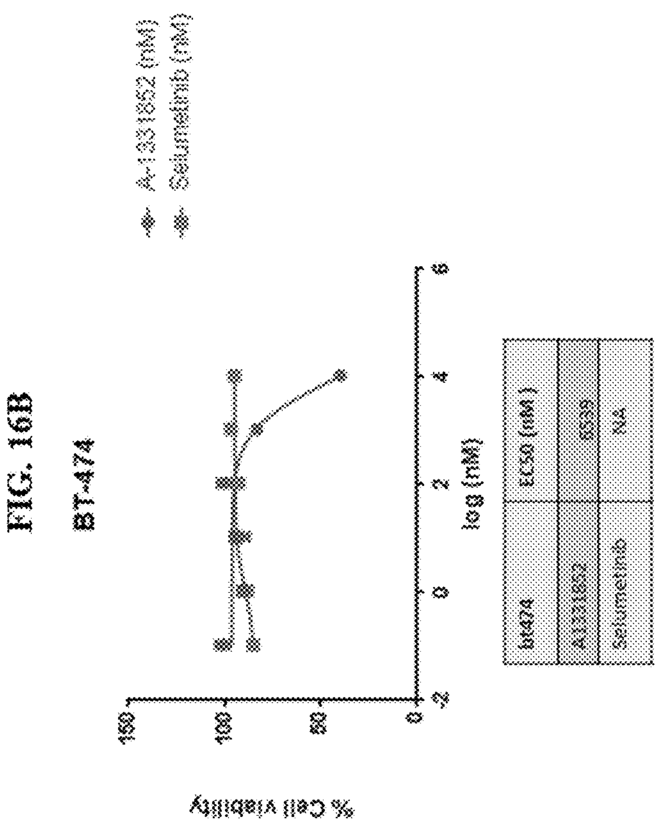

FIG. 16A, and FIG. 16B are graphs showing drug response to A1331852 in breast cancer (BC) cells.

Figure 17:
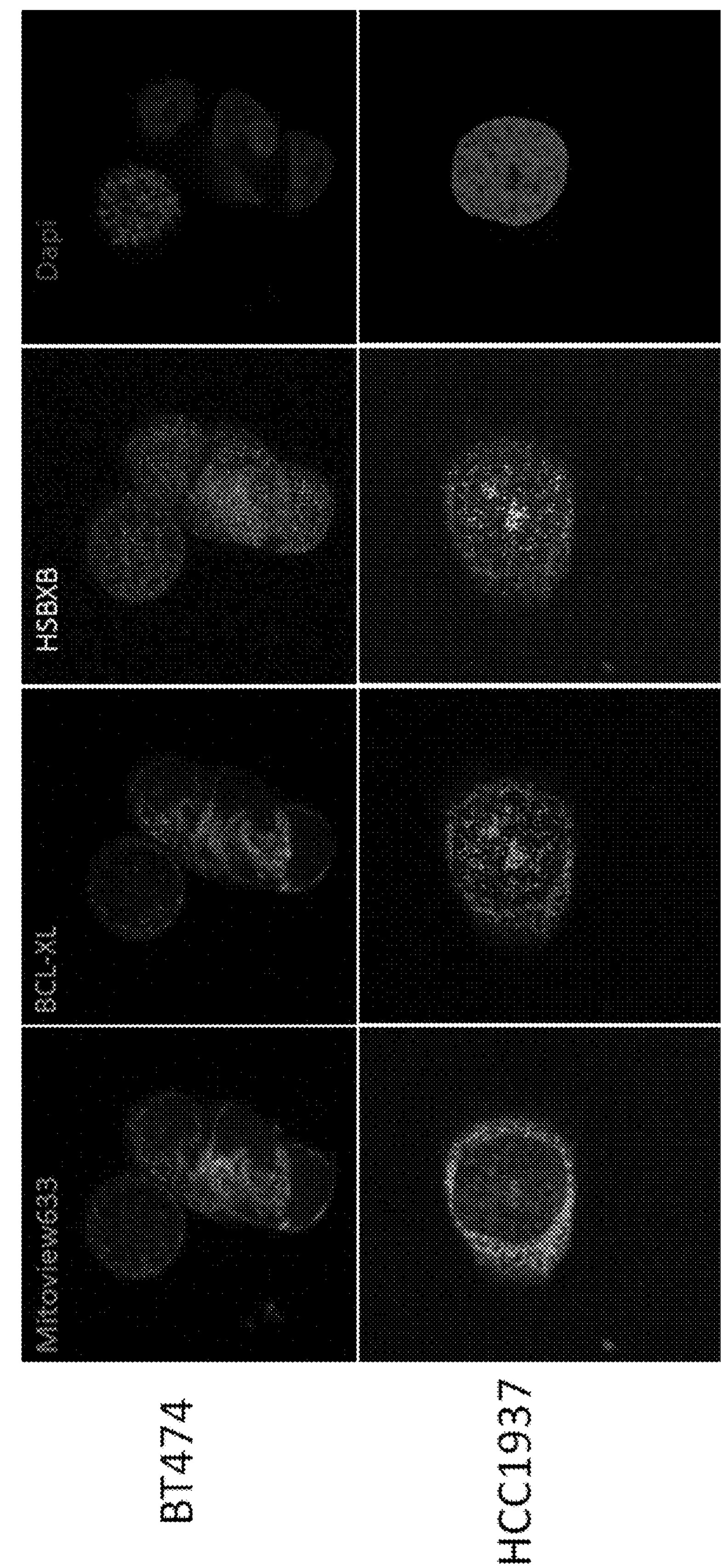

FIG. 17 shows IF staining of HSBXB vs BCL-XL in untreated breast cancer (BC) cells.

FIG. 18 consist of two panel, the panel on the left showing HSBXB and BCL-XL IF in HCC1937 cells+/−A1331852, and the panel on the right showing signal intensity of the inhibitor and control in HCC1937 cells. In the right panel, for each series, the left bar is BCL-XL (A468), and the right bar is HSBXB (A468).

Figure 19:
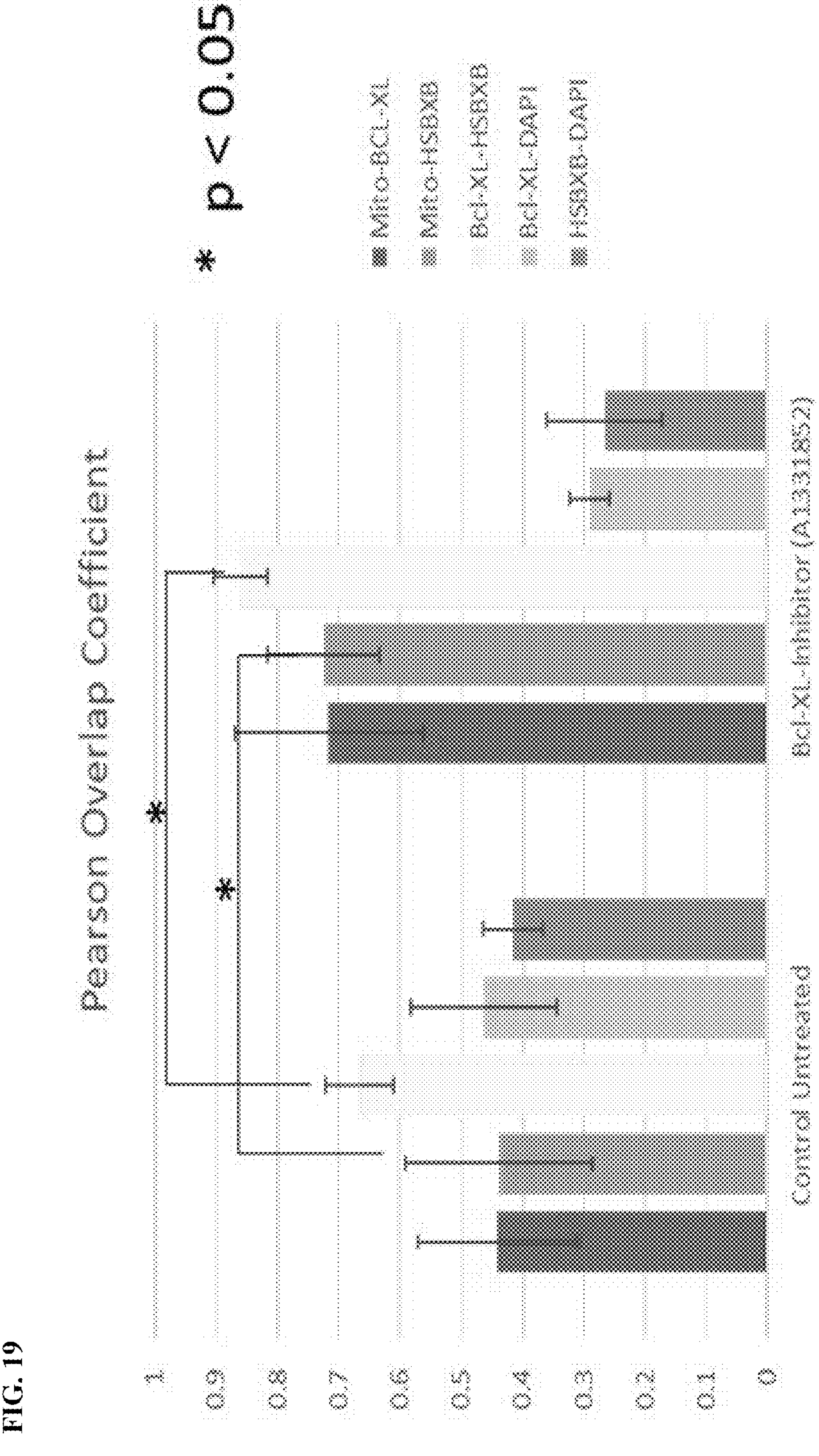

FIG. 19 is a graph showing Bcl-xL localization changes in response to A1331852 in HCC1937 cells. A quantitative analysis was performed using the software Zen 2011 (Blue edition, Carl Zeiss). For each panel, the bar at the far left is Mito-BCL-XL, the next bar is Mito-HSBXB, the next bar is Bcl-XL-HSBXB, the next bar is Bcl-XL-DAPI, and the bar on the far right is HSBXB-DAPI.

Figure 20:
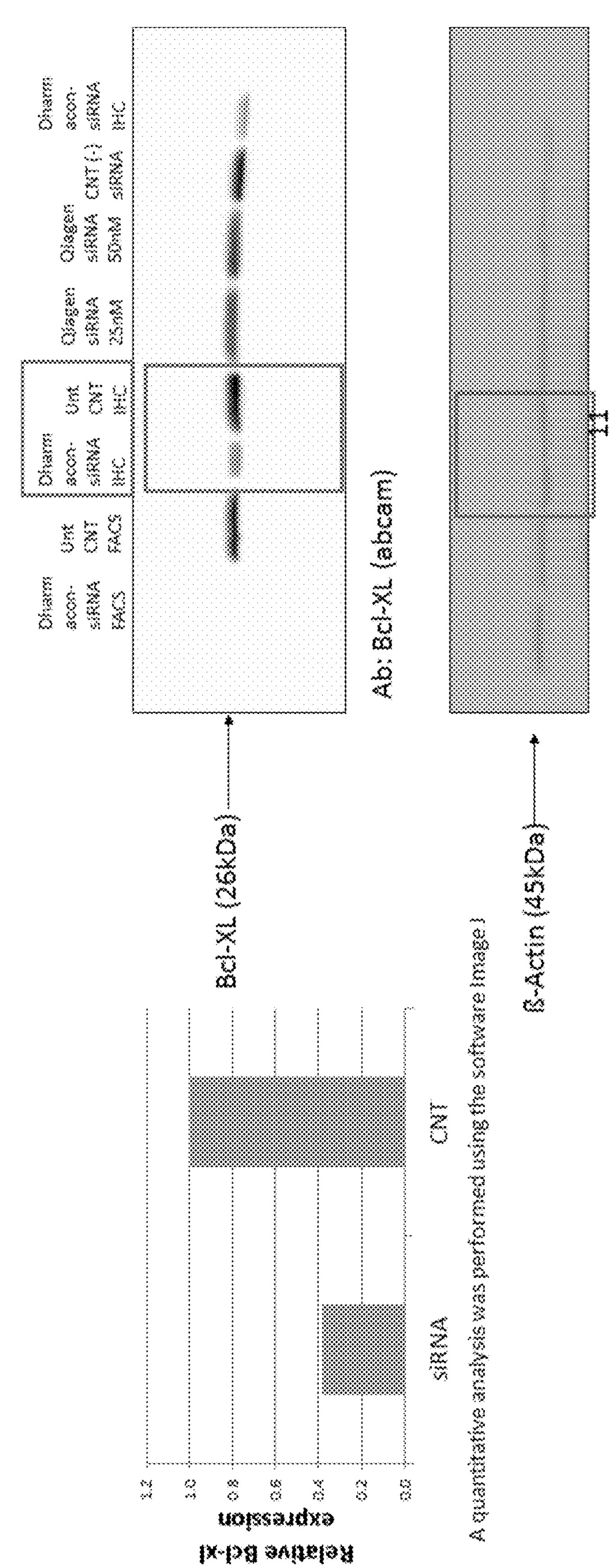

FIG. 20 is a graph and gel image showing knock down of siRNA-BCL-XL in HCC1937 cells. A quantitative analysis was performed using the software Image J.

Figure 21:
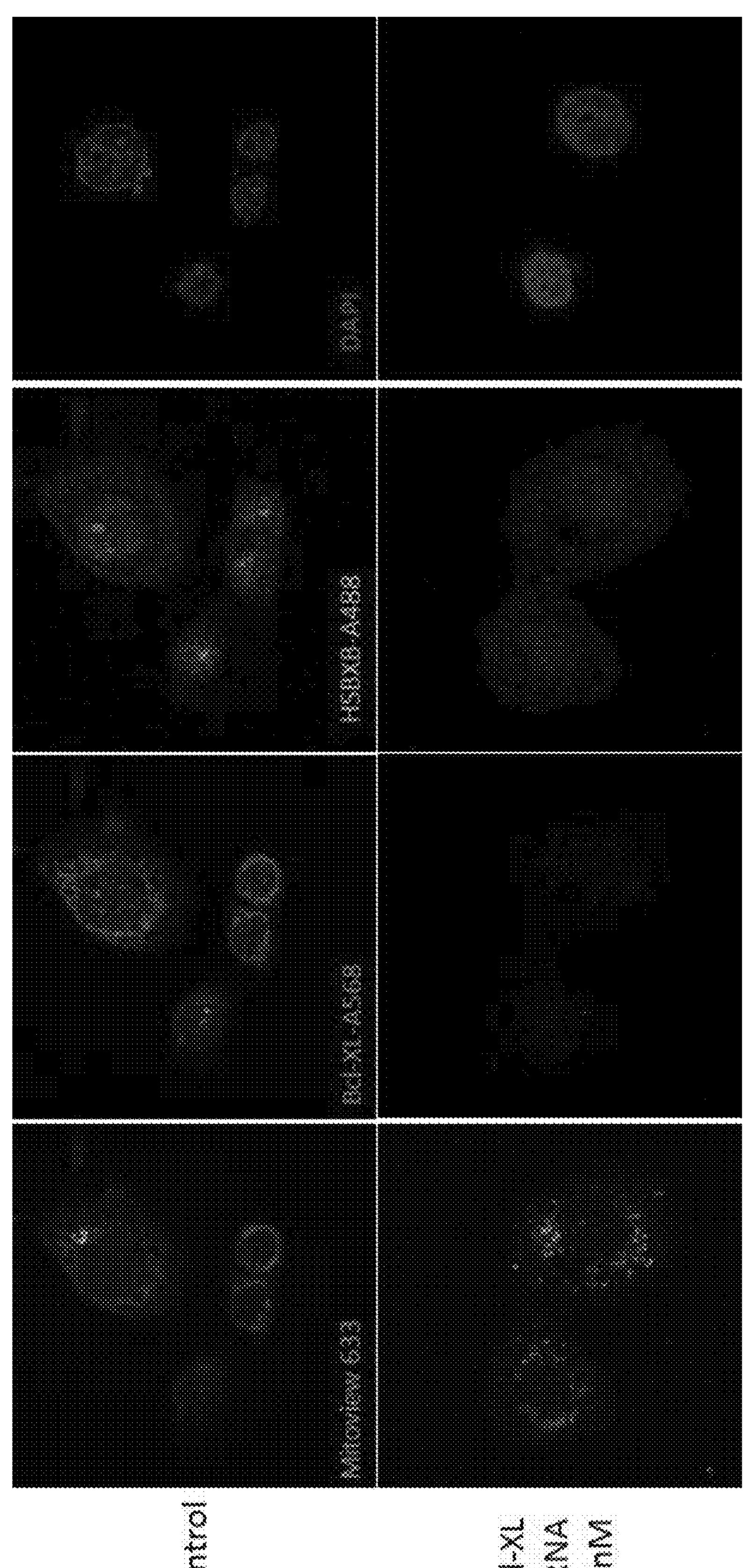

FIG. 21 is an IF image showing Bcl-xL knock down of HCC1937 in breast cancer cells.

Figure 22:
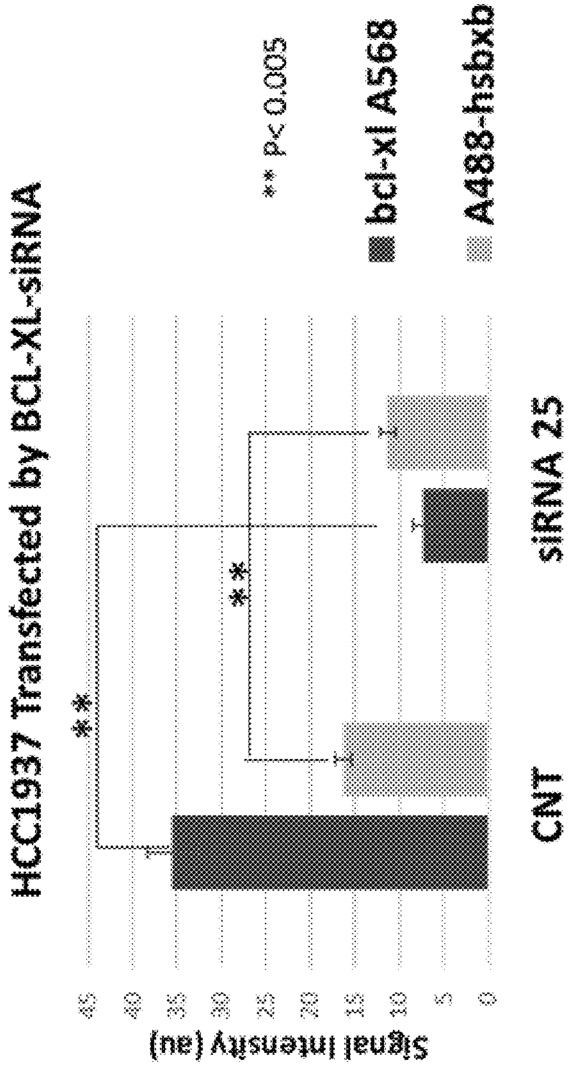

FIG. 22 is a graph showing signal reduction in siRNA BCL-XL HCC1937 cells. A quantitative analysis was performed using the software Zen 2011 (Blue edition, Carl Zeiss). For each series, the bar on the left is BCL-XL (A568), and the bar on the right is A488-HSBXB.

Figure 23:
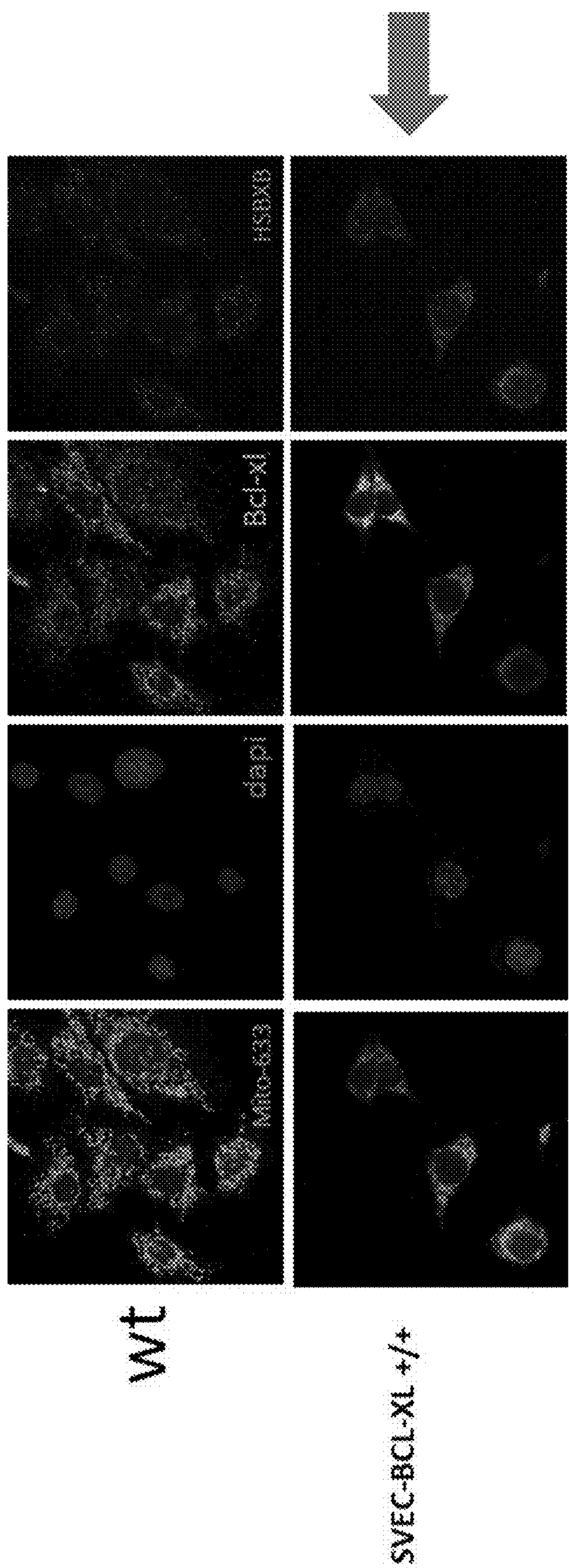

FIG. 23 is an IF image showing SVEC wild type vs. Mito-primed SVEC.

Figures 24A, 24B, 24C:
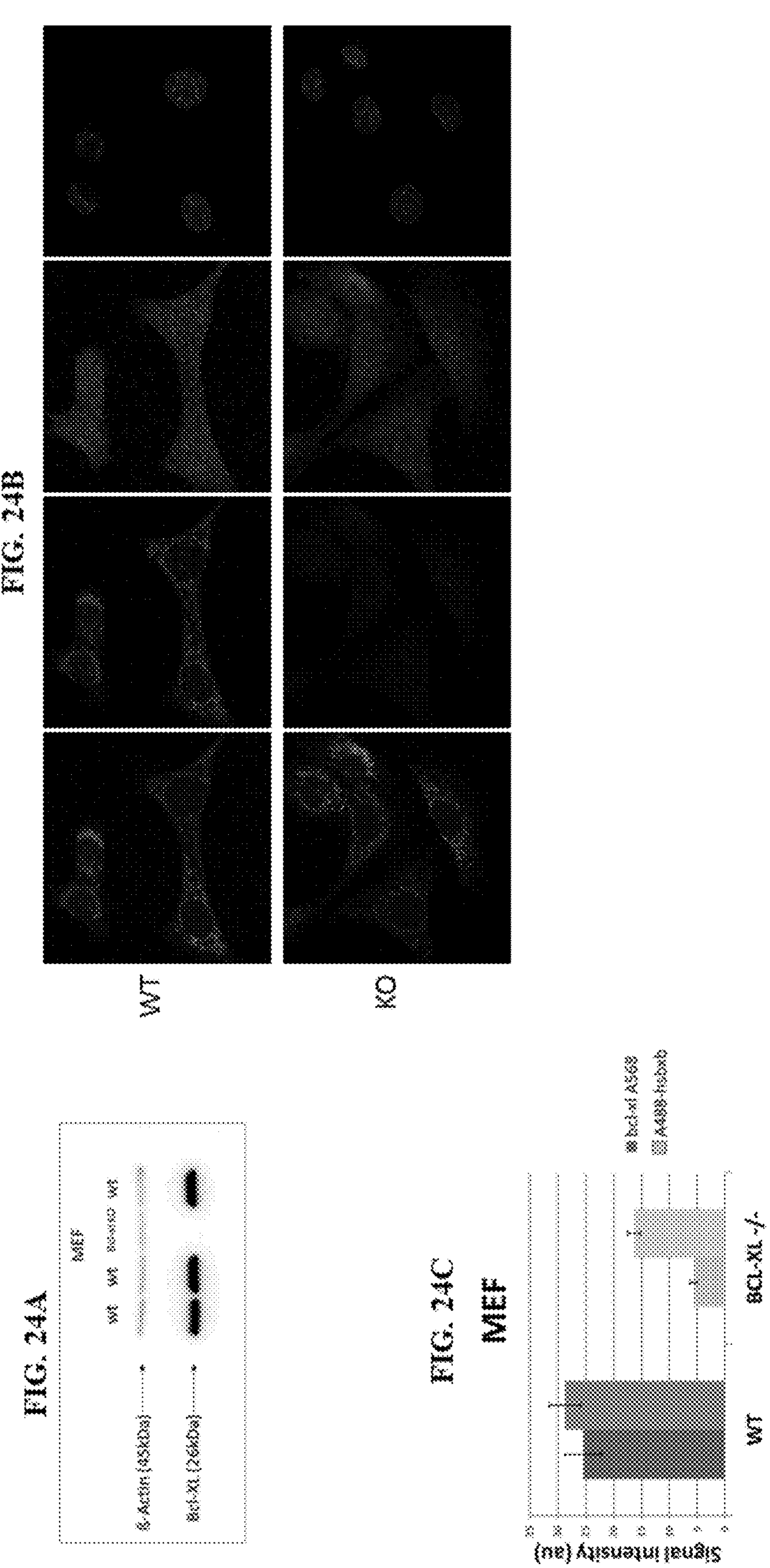

FIG. 24A is an immunoblot of BCL-XL expression in wt vs BCL-xl−/− MEF cells. FIG. 24B is an IF staining of BCL-XL (red) and HSBXB (green) in MEF cells. FIG. 24C is a graph showing signal Intensity of IF staining in MEF cells. For each series, the bar on the left is BCL-XL (A568), and the bar on the right is A488-HSBXB.

Figure 25:
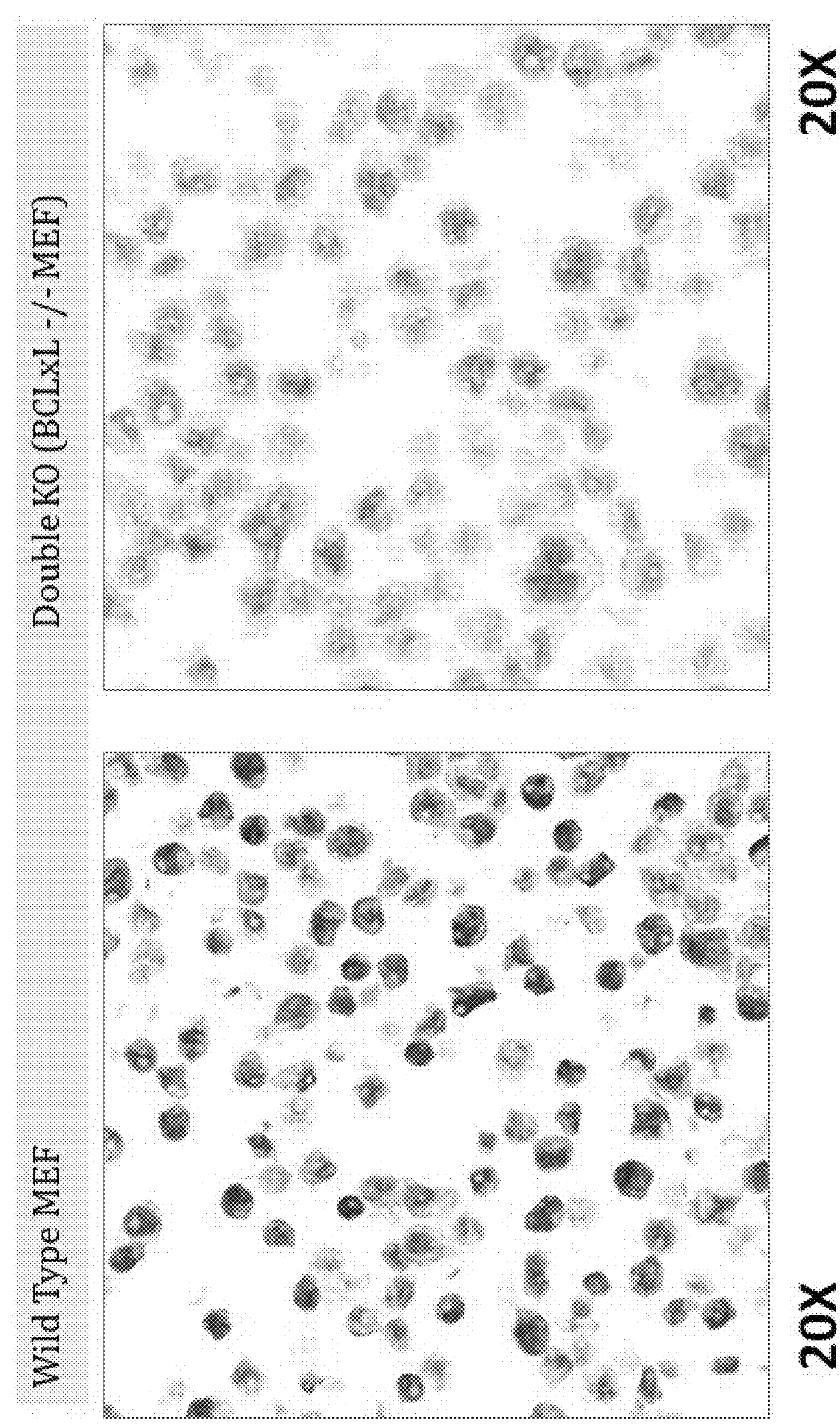

FIG. 25 is an immunohistochemistry (IHC) of HSBxB in MEF wt and BCLxL−/− cells.

Figure 26:
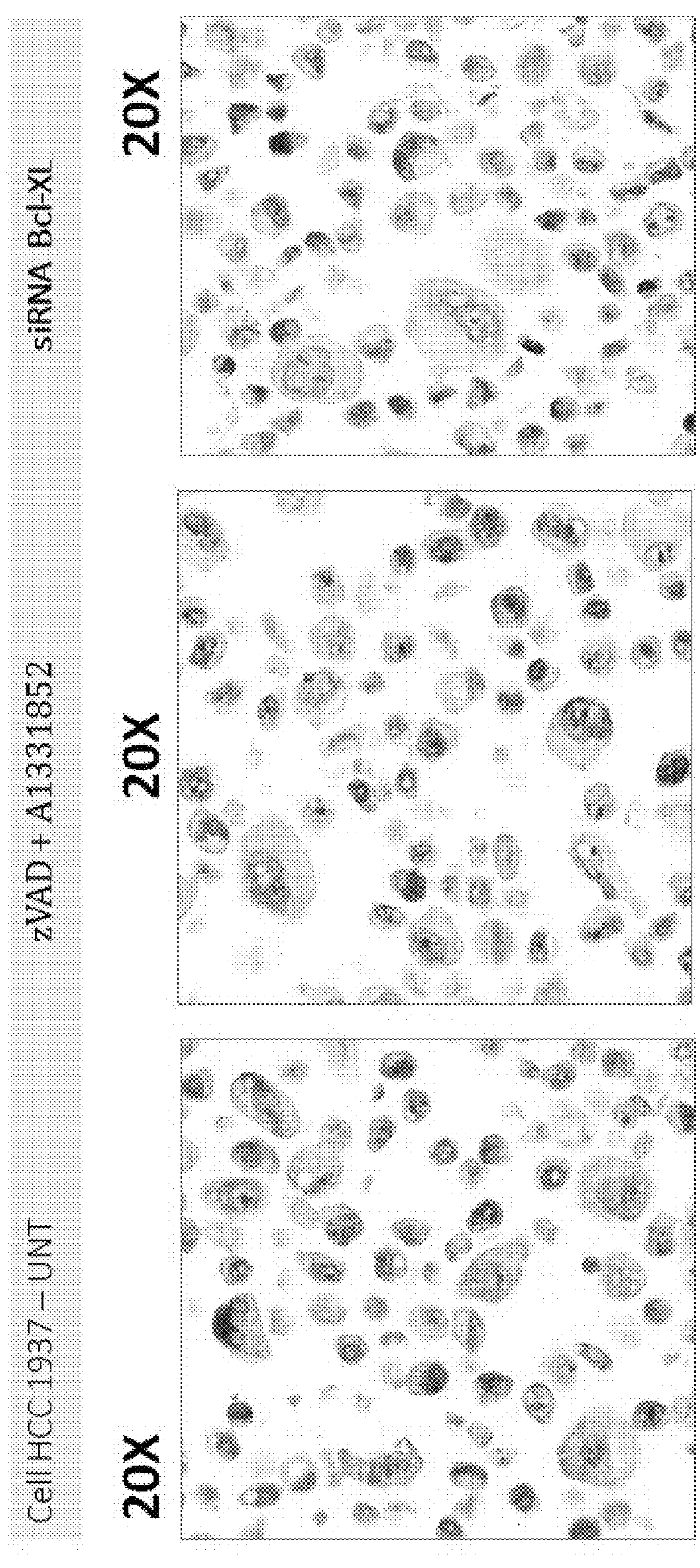

FIG. 26 is an IHC assay of HSBxB in HCC1937 breast cancer cells.

FIG. 27 is an IHC assay of BcLxL in MEFwt and BCLxL−/− MEF cells.

Figure 28:
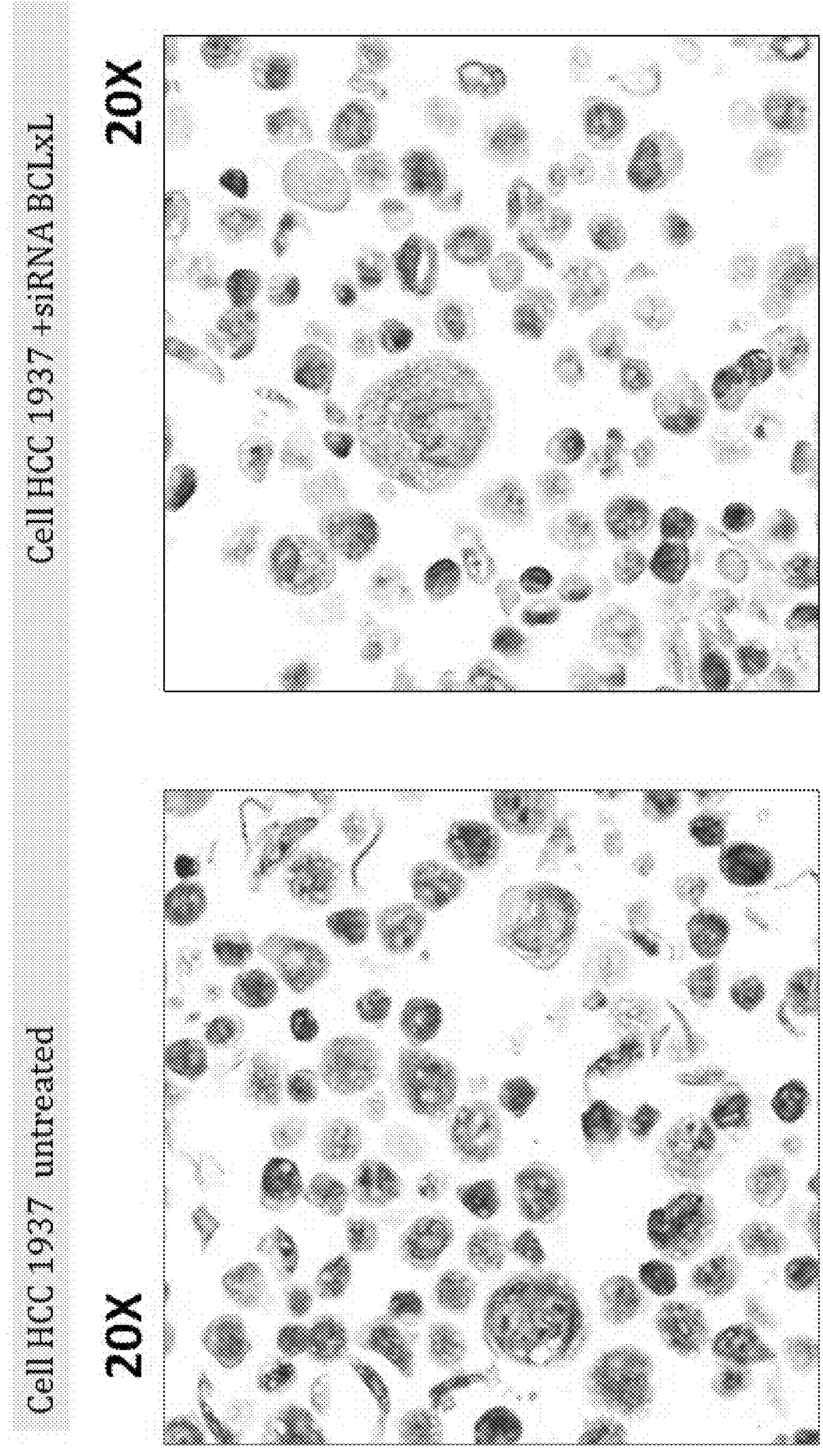

FIG. 28 is an IHC assay of BclxL in HCC1937 treated breast cancer cells.

Figure 29A:
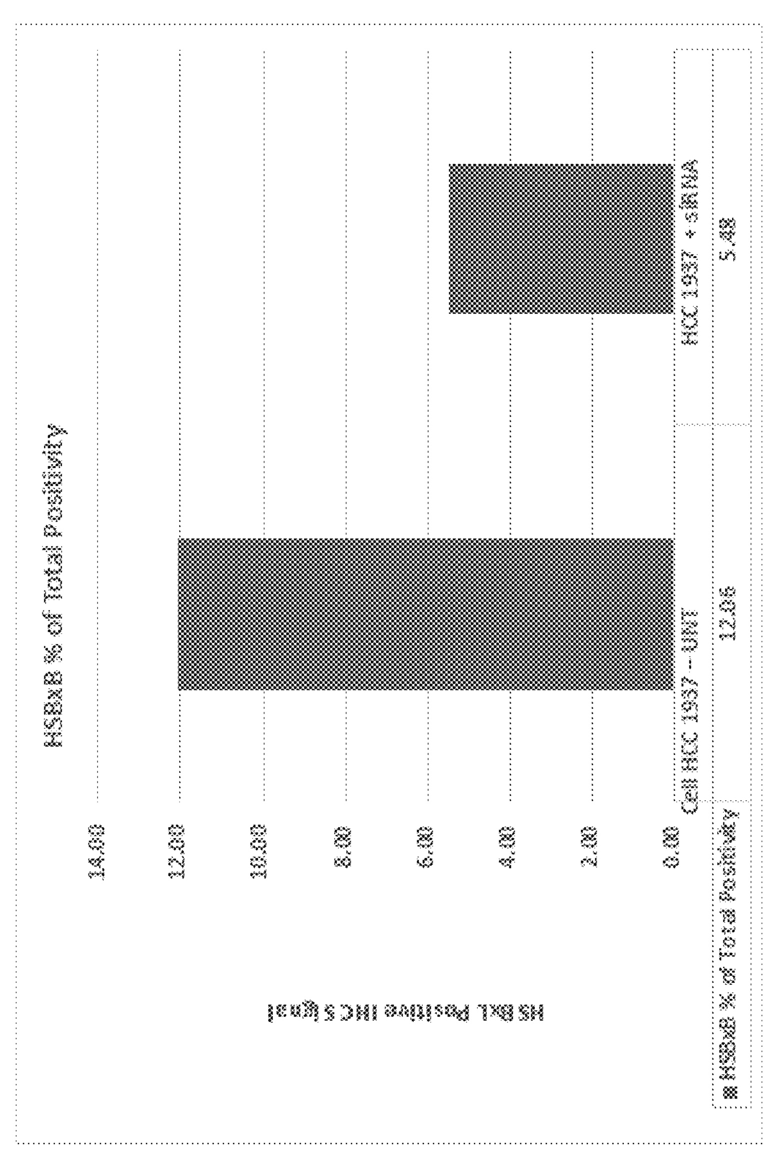
Figure 29B:
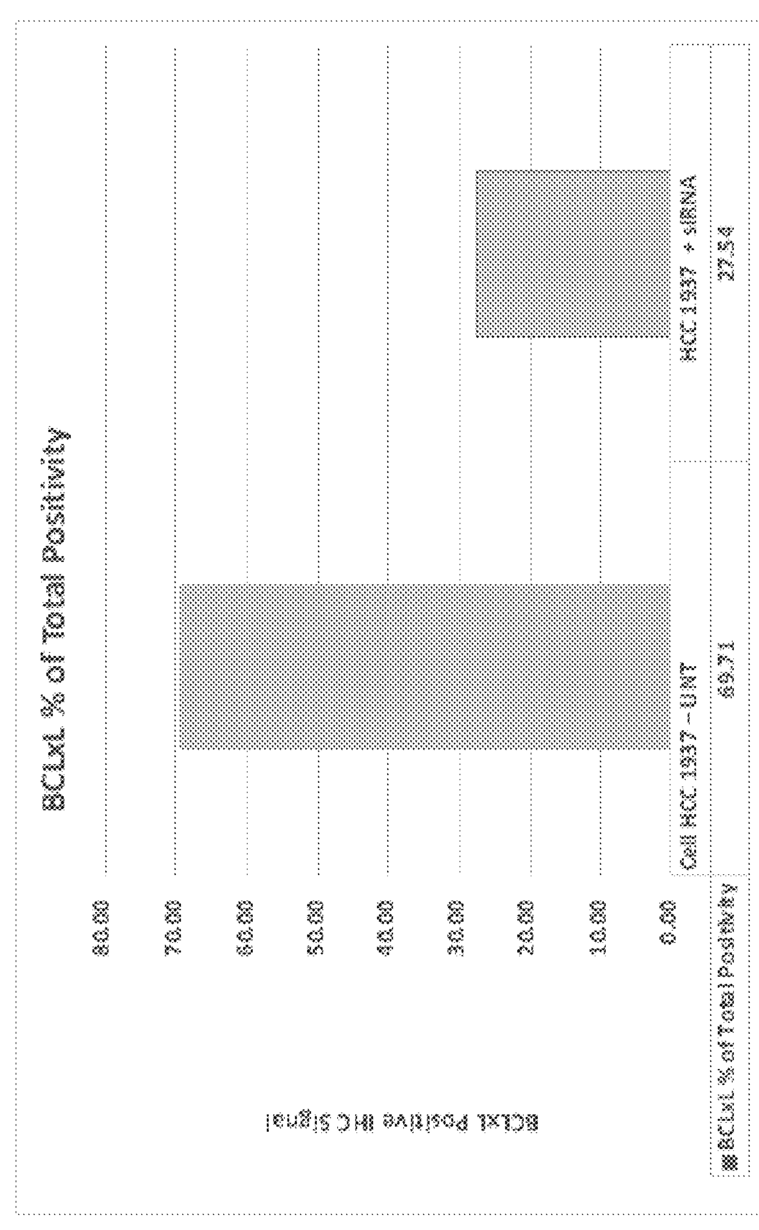

FIG. 29A and FIG. 29B are graphs showing reduced HSBXB (FIG. 29A) and BCL-XL IHC (FIG. 29B) signal intensity in Bcl-XL-siRNA transfected HCC1937 cells. A quantitative analysis was performed using the software Aperio software.

Figure 30:
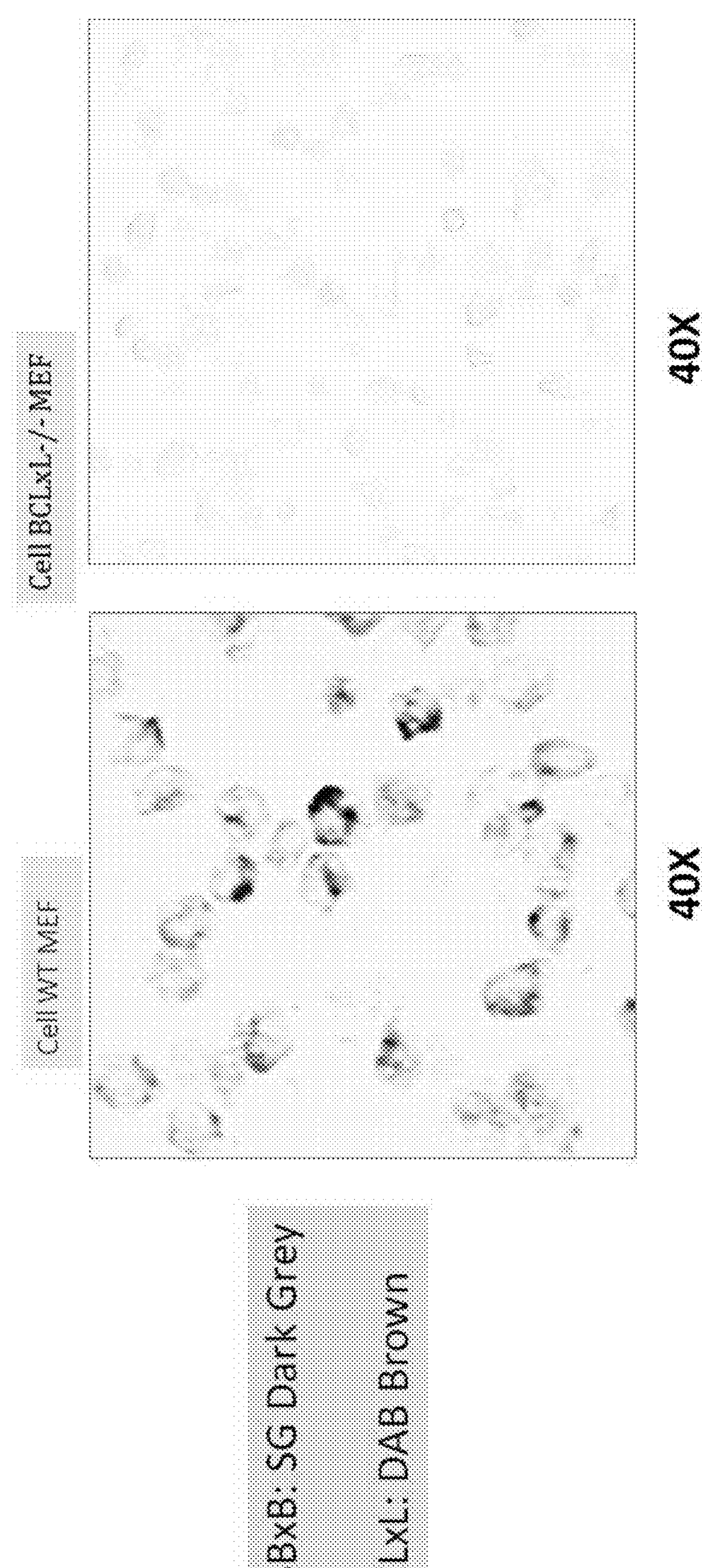

FIG. 30 is an IHC assay showing HSBxB/BclxL in WT MEF and BCL-XL−/− cells.

Figure 31:
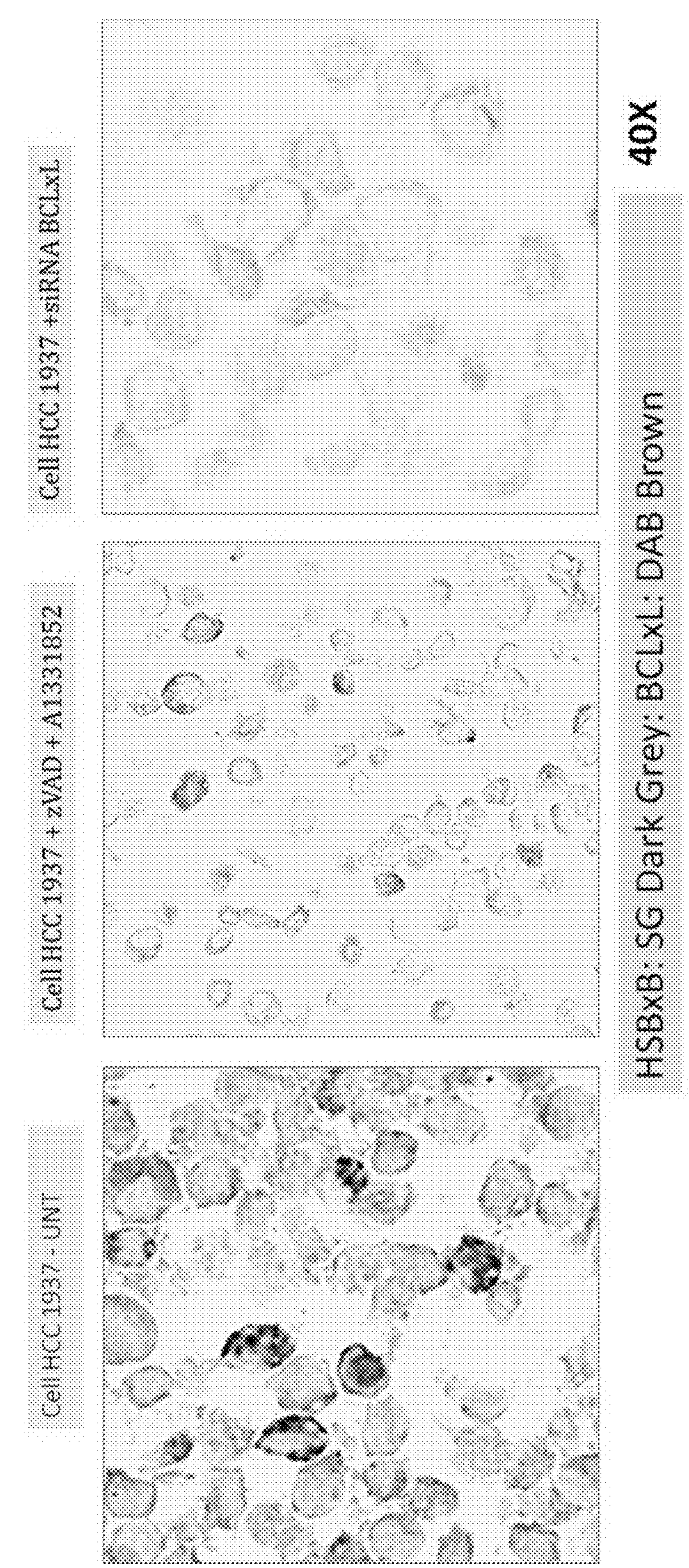

FIG. 31 is an IHC assay showing HSBxB/BCLxL using HCC1937 human breast cancer cells for untreated (left), A-1331852 treated (middle), and siRNA-Bcl-xL treated (right). The digital images were acquired by Aperio Scanscope XT and images were analyzed using the Spectrum Analysis algorithm package and ImageScope analysis software (Aperio Technologies, Inc.) were applied to quantify IHC signals (brown and blue grey). These algorithms make use of a color deconvolution method to separate stains, each stain was individually calibrated by analyzing single-stained sections and recording the hue value and intensity threshold values. The algorithms calculate the percentage of weak (1+), medium (2+), and strong (3+) positive staining. The total positivity signal represents the total number of weak, medium and strong positive staining in each sample.

FIG. 32 is an IHC assay showing HSBxB/BCLxL duplex in SVEC BCL-xL:BIM cells.

Figures 33A, 33B, 33C:
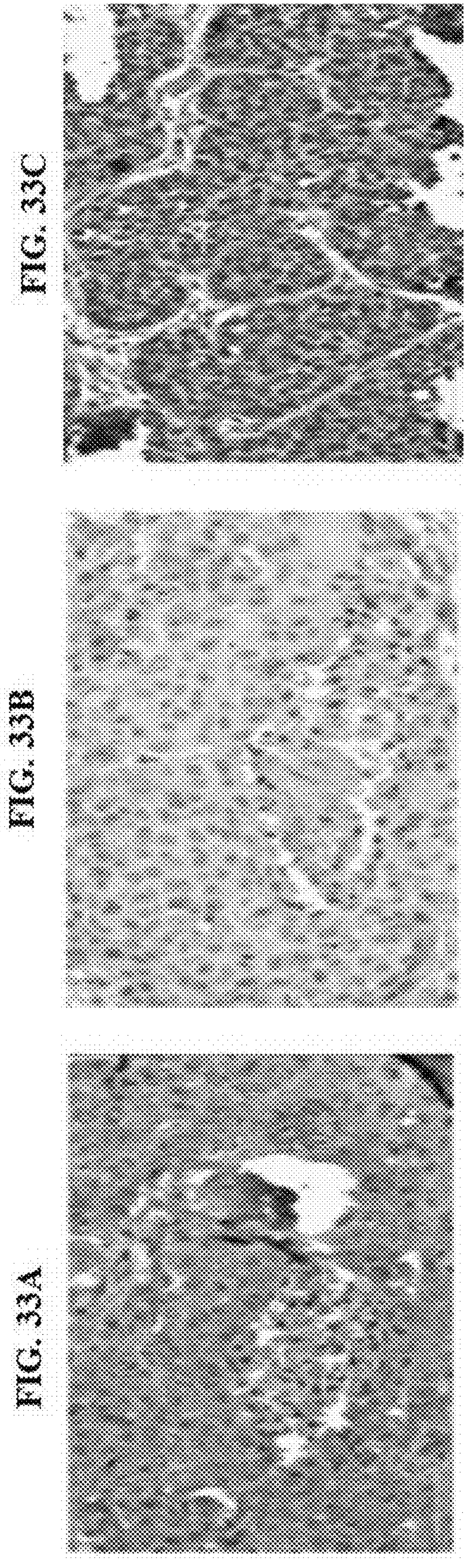

FIG. 33A, FIG. 33B, and FIG. 33C are IHC assays showing the application of HSBXB to FFPE triple negative breast cancer sections using IHC. In FIG. 33A, Patient 21 HBSXB 40× magnification. In FIG. 33B, Patient 21, Control Antibody, 40× magnification. In FIG. 33C, Patient 14, HBSXB 40× magnification.

FIG. 34 is a table showing a broad spectrum application of the IHC assay as HSBXB binding is demonstrated across several tissue derived cancers.

Figure 35A:
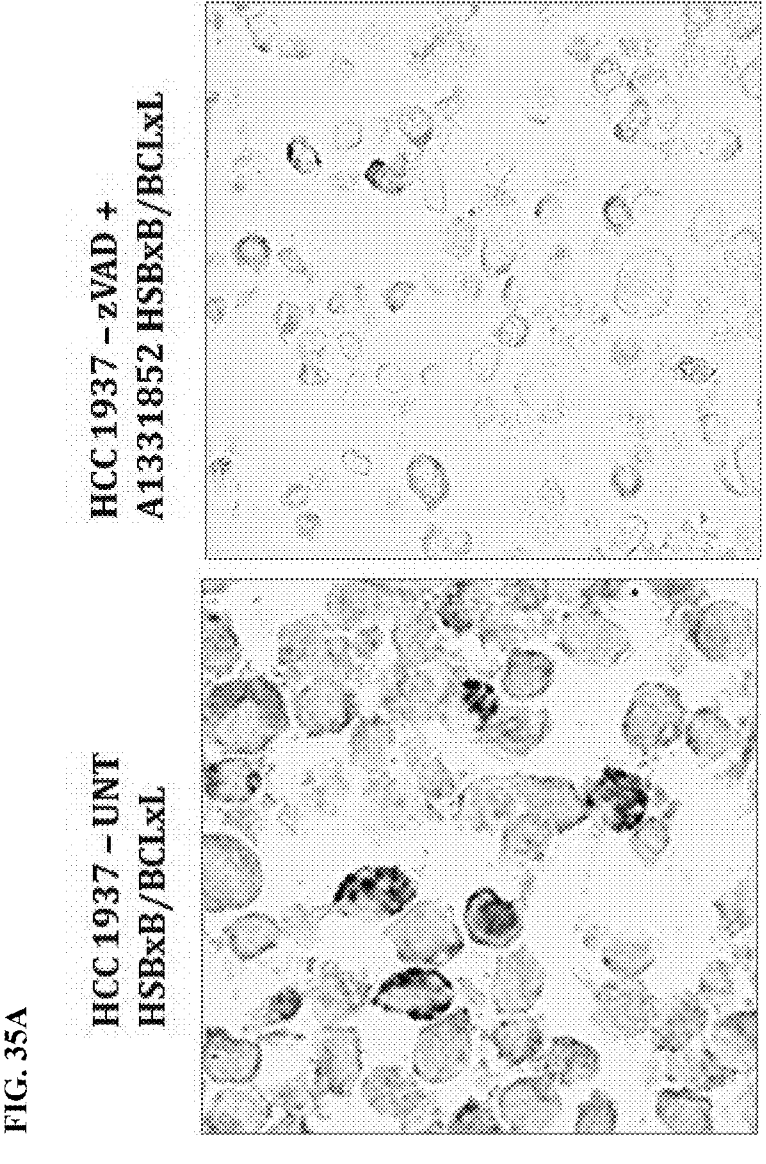
Figure 35B:
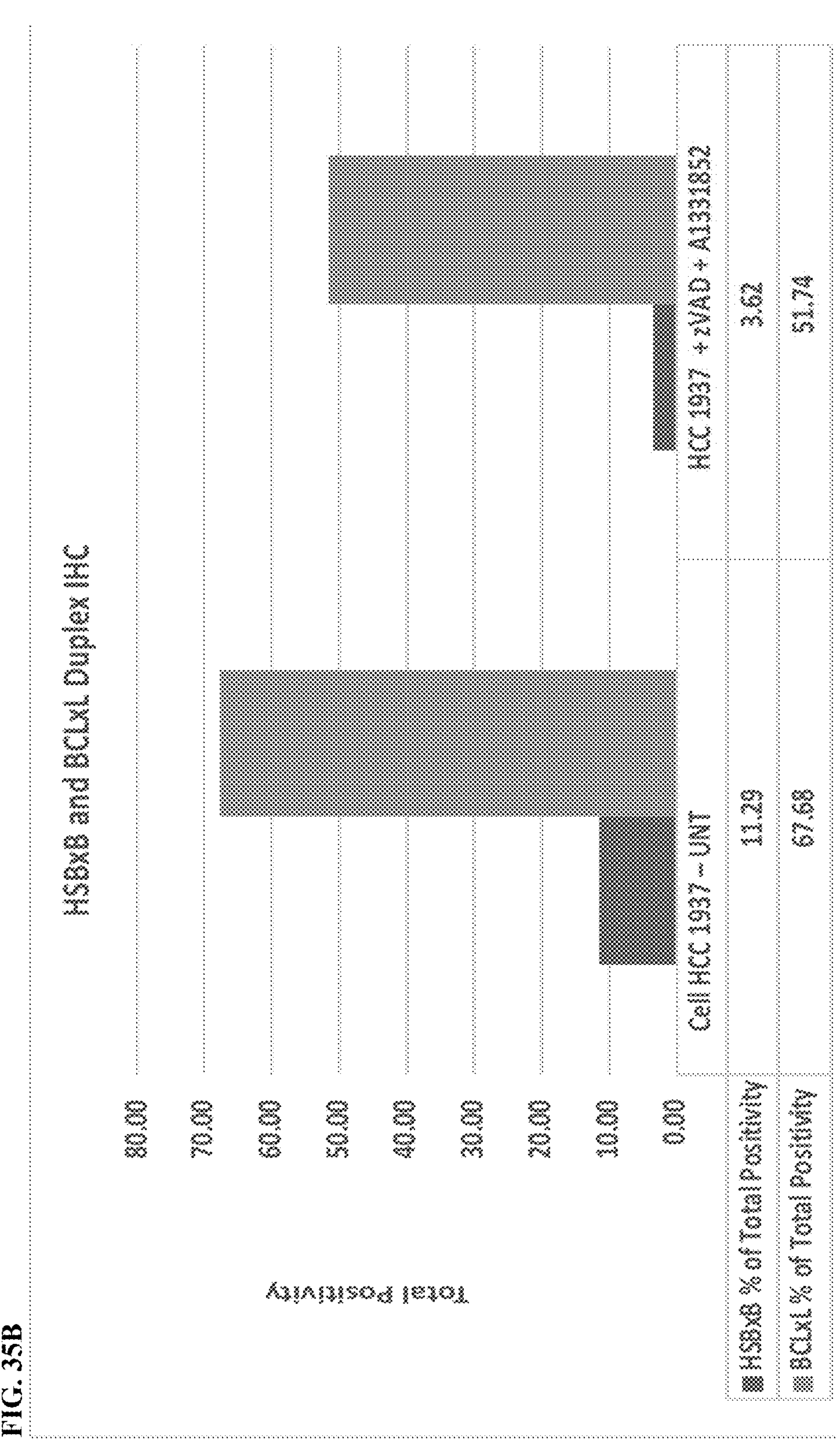

FIG. 35A, FIG. 35B, and FIG. 35C show the results of an IHC of HSBxB/BCLxL duplex staining in the triple-negative breast cancer cell line HCCC 1937 for tissue microarrays (TMA) with and without treatment of zVAD+ A1331852 for 16 hours. For each series, the left bar is HSBXB % of Total Positivity, and the right bar is BCL-xL % of Total Positivity.

Figure 36:
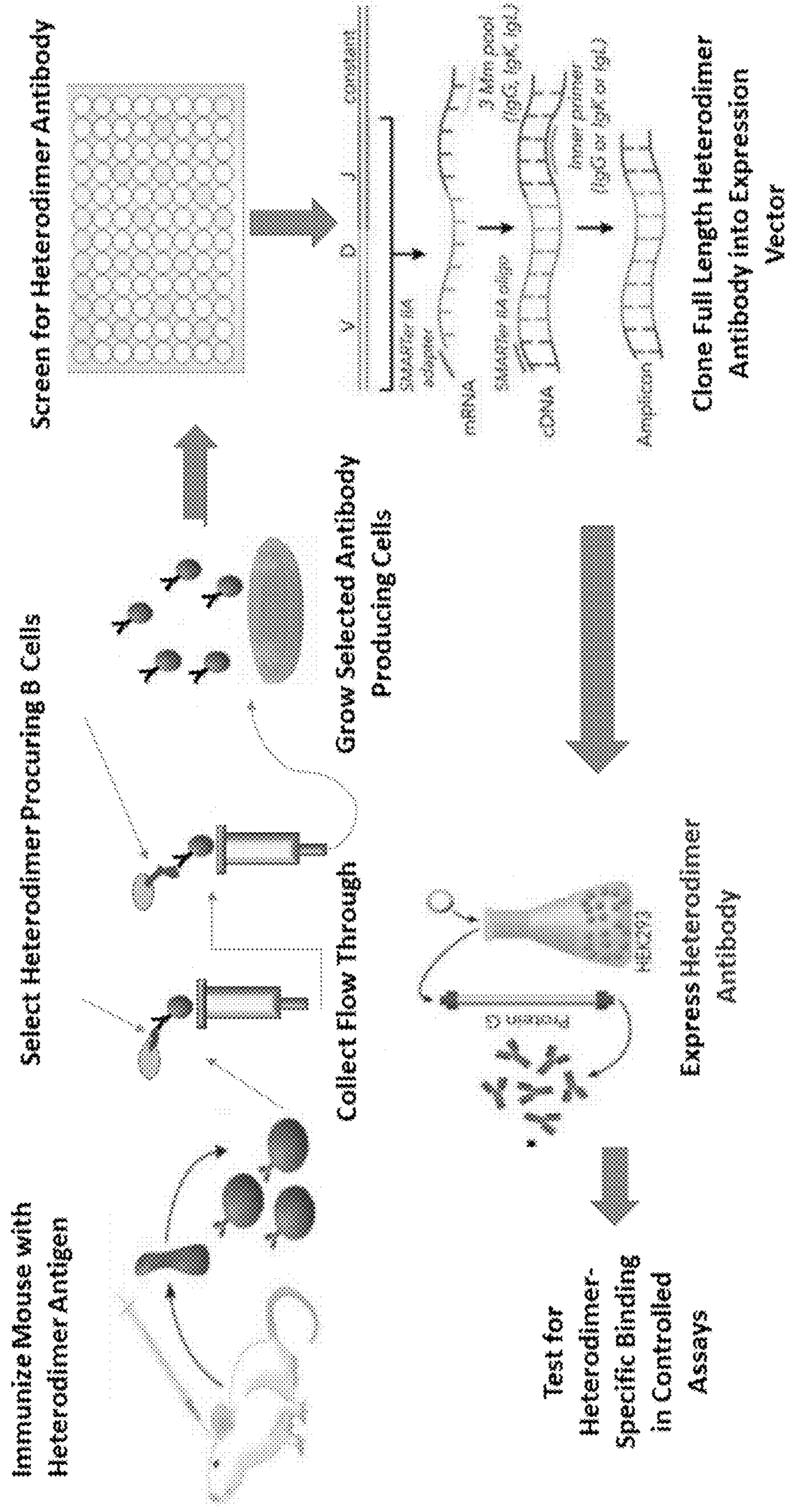

FIG. 36 is a schematic overview showing the experimental steps of a method for selecting, isolating and purifying a heterodimer antibody.

Figure 37:
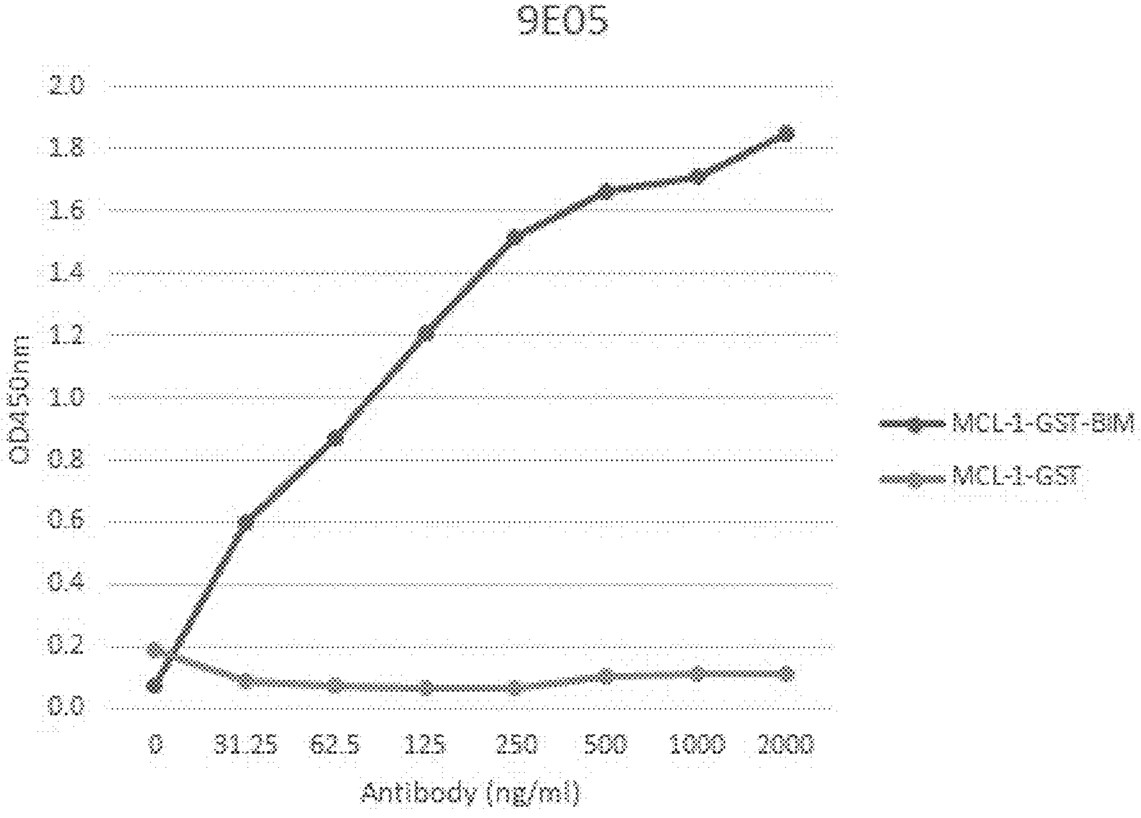

FIG. 37 is a graph showing the selective binding of an IgG clone to a Mcl-1/Bim heterodimer. The line that increases across the graph is MCL-1-GST BIM, and the line that is near the bottom throughout the graph is MCL-1-GST.

Figure 38:
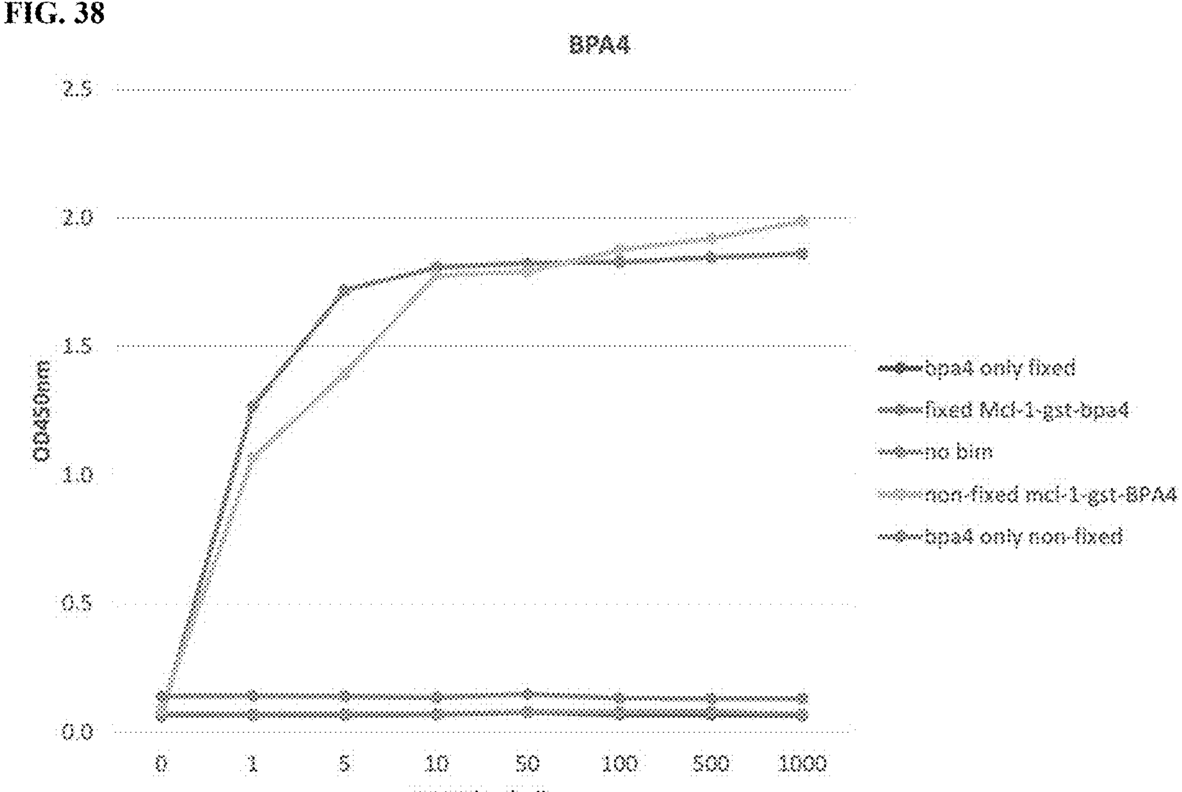

FIG. 38 is a graph showing selective binding of an IgG clone to the modified BPA4 peptide, which is present in the formation of the Mcl-1/Bim heterodimer. Plates were coated with either the Mcl-1/Bim heterodimer, Mcl-1 monomer, or BPA4 peptide alone. Starting at the top of the graph, the line closest to the 2.0 value is the non-fixed Mcl-1-GST-BPA4 sample, and the next line below is the fixed Mcl-1-GST-BPA4 sample, and the next line is the BPA4 only non-fixed sample, and the next two lines merge, which refer to the no-BIM sample and the BPA4 only fixed sample.

Figure 39:
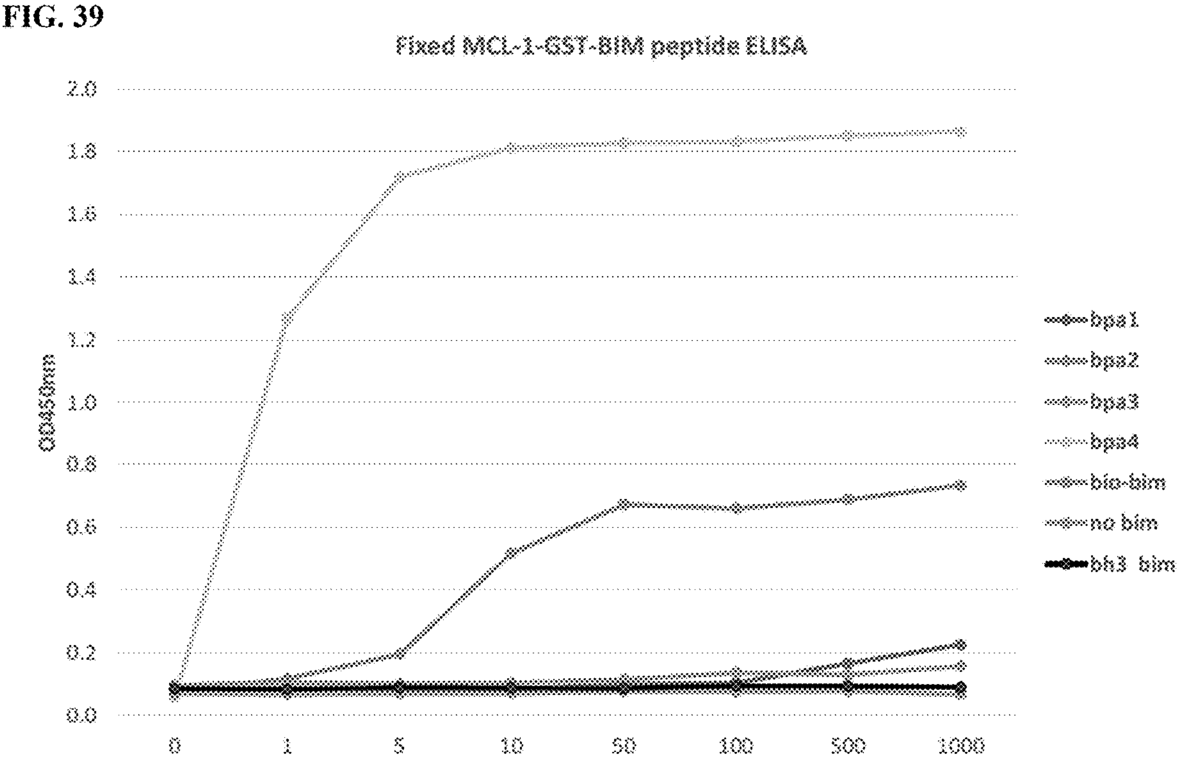

FIG. 39 is a graph showing selective binding of an IgG clone to the modified BPA4 peptide, which is present in the formation of the Mcl-1/Bim heterodimer. Plates were coated with either the Mcl-1/Bim heterodimer with modified BPA peptides, native Bim biotin, or truncated Bim peptide. Starting from the top of the graph, the lines appear in the following order: bpa4, bio-bim, bpa1, and bpa 2; the lines associated with bh3 bim, no-bim, and bpa3 are each at the bottom of the graph.

Figure 40:
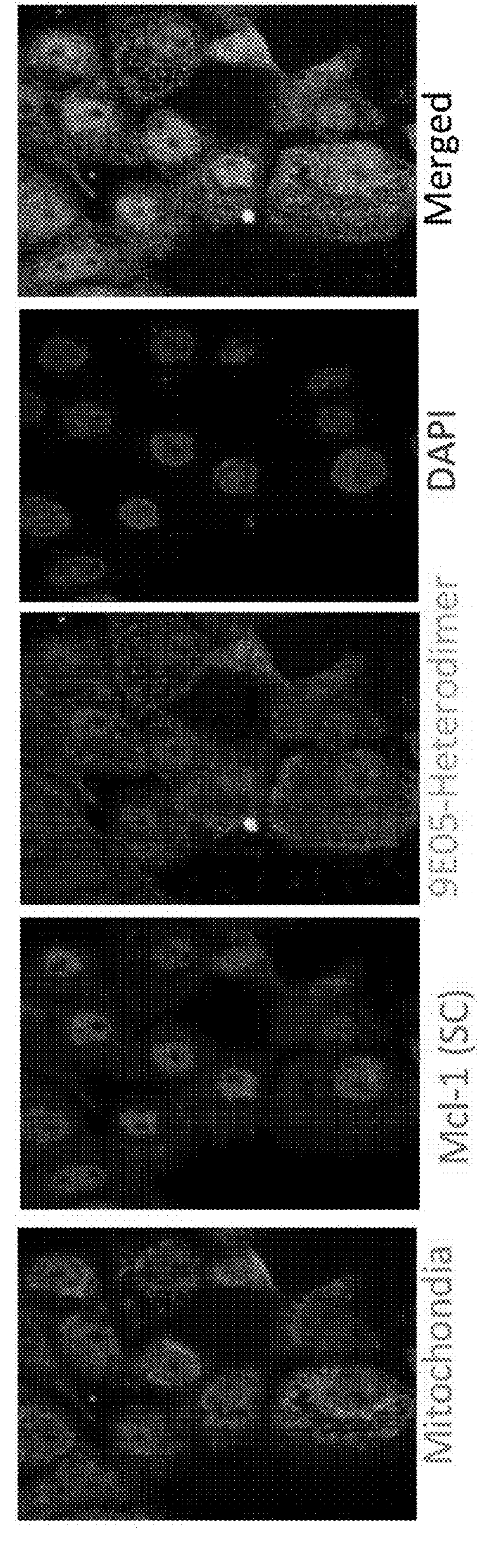

FIG. 40 is an IF image showing Mcl-1/Bim heterodimer specific for clone E905 and Mcl-1 polyclonal rabbit antibody.

Figure 41:
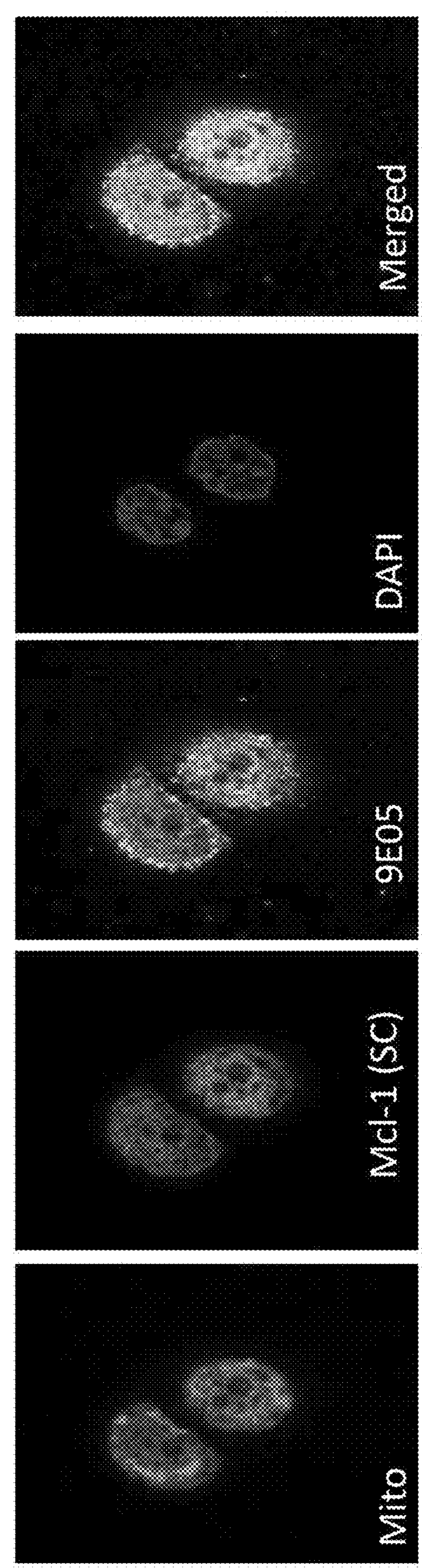

FIG. 41 is an IF image showing Mcl-1/Bim heterodimer specific for clone E905 and Mcl-1 polyclonal rabbit antibody.

Figure 42:
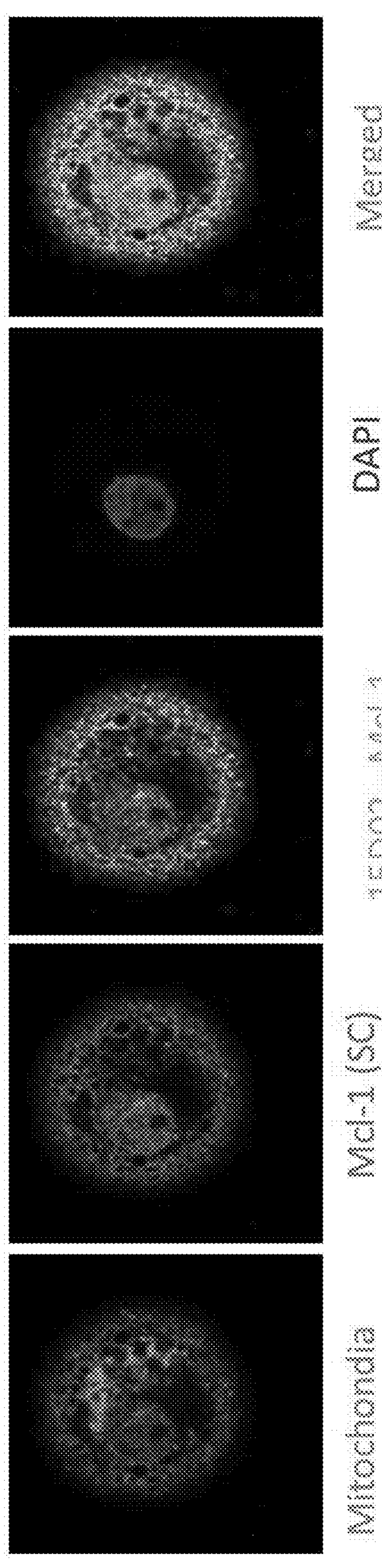

FIG. 42 is an IF image showing Mcl-1 monomer specific for clone 15D02 and Mcl-1 polyclonal rabbit antibody.

Figure 43:
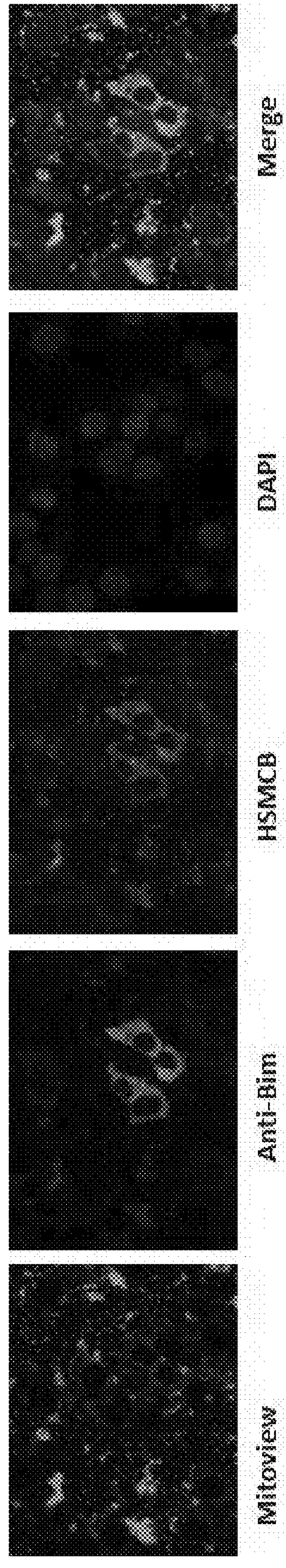

FIG. 43 is an IF image showing that the Mcl-1/Bim heterodimer antibody (HSMCB), requires Bim to bind in situ. Bim siRNA was used on MCF-7 (breast cancer cells), and the cells were then fixed and stained with anti-Bim and HSMCB (Mcl-1/Bim heterodimer specific mAb). Cells not expressing Bim are indicated by lack of red staining (second from left image), but positive for DAPI and mitoview, which do not stain with HSMCB. Otherwise, Bim and Mcl-1/Bim complex colocalize, as expected in the merged view (far right image) in Mcl-1 primed cells.

DETAILED DESCRIPTION

The present disclosure is based, in part, on the discovery of compositions and methods for detecting whether a patient is sensitive to a cancer treatment for instance, by several antibodies that each specifically bind to a Bcl-2 heterodimer (e.g., Bcl-xl/BIM-BH3 heterodimer). The disclosure further provides compositions and methods that are useful for detecting a heterodimer comprising two B-cell lymphoma 2 (BCL-2) proteins in a solid tumor sample from a patient, and determining a ratio of the heterodimer to a reference value, the ratio being predictive of a patient's sensitivity to the cancer treatment. Importantly, the present methods give information about a cancer patient response based on a direct signal, as opposed to a functional one.

Apoptosis is a process of programmed cell death mediated by a number of signaling pathways that converge at the mitochondria. A group of mitochondrial proteins, i.e., the B cell leukemia/lymphoma-2 (BCL-2) family of proteins, regulates this process. More specifically, pro-apoptotic and anti-apoptotic BCL-2 proteins form heterodimers with their cognate regulating BCL-2 proteins (i.e., the BH3-only BCL-2 proteins), thereby effecting cell death or survival signals.

One of the hallmarks of apoptosis is mitochondrial outer membrane permeabilization (MOMP), a process regulated by the Bcl-2 family of proteins. The activity of this family of proteins is linked to the onset of lymphoid and several solid tumor cancers and is believed in many cancers to be a key mediator of resistance to chemotherapy. Bcl-2 proteins are regulated by distinct protein-protein interactions between pro-survival (anti-apoptotic) and pro-apoptotic members. These interactions occur primarily through BH3 (Bcl-2 homology domain-3) mediated binding. Apoptosis-initiating signaling occurs for the most part upstream of the mitochondria and causes the translocation of short, BH3-only, Bcl-2 family members to the mitochondria where they either activate or sensitize MOMP. The activator BH3 only proteins, Bim and Bid, bind to and directly activate the effector, pro-apoptotic proteins Bax and Bak, and also bind to and inhibit the anti-apoptotic Bcl-2 family proteins, Bcl-2, Mcl-1, Bfl-1, Bcl-w and Bcl-xL. The sensitizer BH3 proteins, Bad, Bik, Noxa, Hrk, Bmf and Puma, bind only to the anti-apoptotic Bcl-2 family proteins, Bcl-2, Mcl-1, Bfl-1, Bcl-w and Bcl-xL, blocking their anti-apoptotic functions.

Without wishing to be bound by theory, each sensitizer protein has a unique specificity profile. For example, Noxa (A and B) bind with high affinity to Mcl-1, Bad binds to Bcl-xL and Bcl-2 but only weakly to Mcl-1, and Puma binds well to all three targets. An anti-apoptotic function of these proteins is the sequestering of the activator BH3 protein Bim and Bid by binding to form heterodimers. Displacement of these activators by sensitizer peptides or treatments results in Bax/Bak-mediated apoptotic commitment. These interactions can have various outcomes, including, without limitation, homeostasis, cell death, sensitization to apoptosis, and blockade of apoptosis.

Most effective cancer drugs induce apoptosis in target cancer cells. However, one significant shortfall in current cancer treatment is that different cancer cells can respond to an apoptosis-inducing drug in a variety of manners. This is due, in part, to the presence of different heterodimers between the pro/anti-apoptotic BCL-2 proteins and the regulatory BH3-only BCL-2 proteins in those cancer cells.

In some aspects, the present disclosure provides a method for predicting a patient's sensitivity to a cancer treatment, comprising contacting a sample with an antibody or antibody format that recognizes a heterodimer comprising two B-cell lymphoma 2 (BCL-2) proteins, the sample being a specimen from a solid tumor of the patient; detecting a signal that indicates the amount of the heterodimer; and determining a ratio based on the amount of heterodimer present in the sample to a reference value, wherein the reference value comprises the amount of one of the BCL-2 protein monomers of the heterodimer in the sample, the ratio being predictive of a patient's sensitivity to the cancer treatment.

In another aspect, the present disclosure provides a method for predicting a patient's sensitivity to a cancer treatment, comprising: contacting a sample with an antibody or antibody format that recognizes a heterodimer comprising two B-cell lymphoma 2 (BCL-2) proteins and an antibody or antibody format that recognizes one of the BCL-2 protein monomers of the heterodimer, the sample being a specimen from a solid tumor of the patient; detecting a signal that indicates the amount of the heterodimer and the amount of the monomer; and determining a ratio based on the amount heterodimer to the amount of the monomer, the ratio being predictive of a solid tumor patient's sensitivity to the cancer treatment.

Cancer, Antibodies that Bind Bcl-2 Heterodimers, Bcl-2 Proteins, and Bcl-2 Heterodimers The present disclosure can use the determination of a cancer cell's predisposition to undergo apoptosis to elucidate the cancer's susceptibility to a particular treatment. One way this can be done is by using the disclosed antibodies that bind to Bcl-2 heterodimers which regulate apoptosis. Formation of a heterodimer induces conformational changes in both members of the heterodimer, resulting in exposure of antigenic epitopes that are sequestered in both members before dimerization. The isolated antibodies of the present disclosure specifically recognize such an epitope and only bind to a heterodimer of the Bcl-2 family, not to either non-dimerized member.

One aspect of this disclosure features an isolated antibody that specifically binds to a heterodimer of the Bcl-2 family (i.e., a Bcl-2 heterodimer). The Bcl-2 family includes both Bcl-2 proteins (monomers) and naturally-occurring heterodimers formed between two Bcl-2 proteins. The heterodimer contains a first Bcl-2 protein (e.g., Bim, Bid, Bad, Puma, Noxa, Bak, Hrk, Bax, or Mule) and a second Bcl-2 protein (e.g., Mcl-1, Bcl-2, Bcl-XL, Bfl-1 or Bcl-w). In some embodiments, the BCL-2 protein is an activator BH3 protein, and the activator BH3 protein is selected from BID and BIM. In some embodiments, the BCL-2 protein is a sensitizer BH3 protein. The sensitizer BH3 protein is selected from BAD, BIK, NOXA A, NOXA B, HRK, BMF, and PUMA. In some embodiments, the BCL-2 protein is a multidomain pro-apoptotic protein, and the multidomain pro-apoptotic protein is selected from BAX and BAK. In some embodiments, the BCL-2 protein is a multidomain anti-apoptotic protein and the multidomain anti-apoptotic protein is selected from BCL-2, BCL-XL, MCL-1, BCL-W, and BFL-1. In some embodiments, the heterodimer comprises BCL2 and one of BID, BIM, BAD, BIK, PUMA, and BMF.

The methods of the present disclosure also provide a ratio of heterodimer to one of BCL2, BID, BIM, BAD, BIK, PUMA, and BMF monomer. The heterodimer can comprise BCLXL and one of BID, BIM, BAD, BIK, HRK, PUMA, and BMF. The method can also provide a ratio of heterodimer to one of BCLXL, BID, BIM, BAD, BIK, HRK, PUMA, and BMF monomer. The heterodimer may comprise BCLW and one of BID, BIM, BIK, PUMA, and BMF. In some embodiments, the method provides a ratio of heterodimer to one of BCLW, BID, BIM, BIK, PUMA, and BMF monomer. The heterodimer can comprise MCL1 and one of BID, BIM, BIK, NOXA A, NOXA B, PUMA, BAK, and BMF. In some embodiments, the method provides a ratio of heterodimer to one of MCL1, BID, BIM, BIK, NOXA A, NOXA B, PUMA, and BMF monomer. In some embodiments, the heterodimer comprises BFL1 and one of BID, BIM, NOXA A, NOXA B, and PUMA. In some embodiments, the method provides a ratio of heterodimer to one of BFL1, BID, BIM, NOXA A, NOXA B, and PUMA monomer.

The methods of the present disclosure also provide an antibody or antibody format that recognizes a heterodimer of BCL2 and one of BID, BIM, BAD, BIK, PUMA, and BMF. In some embodiments, the antibody or antibody format recognizes a heterodimer of BCLXL and one of BID, BIM, BAD, BIK, HRK, PUMA, and BMF. In some embodiments, the antibody or antibody format recognizes a heterodimer of BCLW and one of BID, BIM, BIK, PUMA, and BMF. In some embodiments, antibody or antibody format recognizes a heterodimer of MCL1 and one of BID, BIM, BIK, NOXA A, NOXA B, PUMA, BAK, and BMF. In some embodiments, the antibody or antibody format recognizes a heterodimer of BFL1 and one of BID, BIM, NOXA A, NOXA B, and PUMA.

The compositions of the present disclosure include an antibody or antibody format comprising: (i) a heavy chain variable region comprising heavy chain CDR1, CDR2, and CDR3 sequences, wherein the heavy chain CDR1 sequence is GHTFTEHYIN (SEQ ID NO: 1), the heavy chain CDR2 sequence is WIFPGSGSTYYNEKFKG (SEQ ID NO: 2); and the heavy chain CDR3 sequence is SYSNFWFAY (SEQ ID NO: 3); and (ii) a light chain variable region comprising light chain CDR1, CDR2, and CDR3 sequences, wherein the light chain CDR1 sequence is RASQSIGTSIH (SEQ ID NO: 4), the light chain CDR2 sequence is KYASESIS (SEQ ID NO: 5), and the light chain CDR3 sequence is QQSNSWPTT (SEQ ID NO: 6). The antibody or antibody format can comprise: (i) a heavy chain variable region sequence comprising the amino acid sequence set forth in SEQ ID NO: 7 or the amino acid sequence of SEQ ID NO: 7 with no more than 10 total amino acid substitutions; and (ii) a light chain variable region sequence comprising the amino acid sequence of SEQ ID NO: 8 or the amino acid sequence of SEQ ID NO: 8 with no more than 10 total amino acid substitutions. The antibody or antibody format can comprise an amino acid sequence having at least 90%, or 93%, or 95%, or 97%, or 98% identity with SEQ ID NO: 7 and/or SEQ ID NO. 8.

Bcl-2 proteins, which are present in mitochondria, are major regulators of the commitment to programmed cell death and executioners of death/survival signals. (See, e.g., Reed, Natural Clinical Practice Oncology, 3:388-398 (2006), Green et al., Cancer Cell 1:19-30 (2002), and Adams et al., Cold Spring Harb. Symp. Quant. Biol. 70:469-477 (2005)) There are four sub-groups of Bcl-2 proteins: (i) multi-domain anti-apoptotic Bcl-2 proteins, (ii) multi-domain pro-apoptotic Bcl-2 proteins, (iii) activator BH3-only Bcl-2 proteins, and (iv) sensitizer BH3-only Bcl-2 proteins. Table 1 below lists major human Bcl-2 proteins and their GenBank accession numbers:

TABLE 1

Human Bcl-2 Proteins

| Bcl-2 Proteins Class | Bcl-2 proteins | Gene Bank Accession numbers |
|---|---|---|
| Multi Domain | Bcl-2 | AAH27258 (Jul. 15, 2006) |
| Anti-Apoptotic | Mcl-1 | AAF64255 (Jul. 15, 2000) |
| | BCL-XL | AAH19307 (Jul. 15, 2015) |
| | BFL-1 | Q16548 (Mar. 3, 2009) |
| | BFL-W | AAB09055 (Sep. 29, 1996) |
| Multi Domain | BAX | Q07812 (Apr. 14, 2009) |
| Pro-Apoptotic | BAK | Q16611 (Apr. 14, 2009) |
| Activator | BID | P55957 (Mar. 3, 2009) |
| BH3 only class | BIM | O43521 (Apr. 14, 2009) |
| Sensitisor | BAD | CAG30276 (Jun. 29, 2004) |
| BH3 only class | NOXA | Q13794 (Mar. 3, 2009) |
| | PUMA. | Q9BXH1 (Apr. 14, 2009) |
| | HRK, | AAC34931 (Sep. 9, 1998) |
| | Mule | Q7Z67Z (Apr. 14, 2009) |
| | BIK | CAG30276 (Oct. 16, 2008) |
| | BMF | AAH63928 (Aug. 19$^{th}$, 2004) |

Other Bcl-2 proteins, if any, can be identified by a homologous search using the amino acid sequence of a known Bcl-2 protein as a query.

Polypeptides can be identified based on homology to the BH3 domain, and polypeptides can possess at least about 50%, about 60%, about 70%, about 80%, about 90%, about 95%, about 96%, about 97%, about 98%, about 99% sequence homology to the amino acid sequences of the polypeptides disclosed in Table 1. Preferred variants are those that have conservative amino acid substitutions made at one or more predicted non-essential amino acid residues. For example, a "conservative amino acid substitution" is one in which the amino acid residue is replaced with an amino acid residue having a similar side chain. In a further embodiment, the BH3 domain peptide is an activator or a sensitizer of apoptosis. In a preferred embodiment, the BH3 domain peptide is a sensitizer.

In one embodiment, the heterodimer comprises different members of the Bcl-2 family. In another embodiment, the heterodimer of Bcl-2 family contains a first member of the Bcl-2 family selected from the group consisting of Bim, Bid, Bad, Puma, Noxa, Bak, Hrk, Bax, Bmf, and Mule, and a second member of the Bcl-2 family selected from the group consisting of Mcl-1, Bcl-2, Bcl-XL, Bfl-1, and Bcl-w. In another embodiment, the first member of the Bcl-2 family is Bim and the second member of the Bcl-2 family is Mcl-1, Bcl-XL, or Bcl-2. In one embodiment, the heterodimer comprises Bcl-XL and Bim. In another embodiment, the heterodimer comprises Bim and Mcl-1. In another embodiment, the heterodimer comprises Bim and Bcl-2. In another embodiment, the heterodimer comprises Bid and Bcl-2.

If a cell is pre-set to undergo drug-induced apoptosis (e.g. the cell is dependent on Bcl-2 polypeptide activity for survival), the antibodies of the disclosure can be used to identify the specific Bcl-2 proteins that are responsible for apoptotic block.

It is known that members in one subgroup of Bcl-2 proteins form heterodimers with members in a different subgroup to regulate apoptosis. As shown in FIG. 1, formation of a heterodimer induces conformational changes in both members of the heterodimer, resulting in exposure of antigenic epitopes that are sequestered in both members before dimerization. The isolated antibodies of the present disclosure specifically recognize such an epitope (e.g., the arrow epitope shown in FIG. 1). In other words, the antibodies disclosed herein can specifically bind to a heterodimer of the Bcl-2 family.

Briefly, without wishing to be bound by theory, as a result of aberrant phenotypes, cancer cells develop blocks in apoptosis pathways. These blocks make cancer cells both resistant to some therapies, and, surprisingly, make some cancer cells sensitive to other therapies. The concept of "oncogene addiction" describes the phenomena of the acquired dependence of cancer cells on, or addiction to, particular proteins for survival. Cancer cells can be, but are not always, pre-set to undergo apoptosis and this is a function of these cells being dependent on any, or all of the anti-apoptotic Bcl-2 family proteins for their otherwise unintended survival. This provides insight into the likelihood of a cancer cell to respond to treatment.

Cancer cells, without wishing to be bound by theory, exhibit abnormalities, such as DNA damage, genetic instability, abnormal growth factor signaling, and abnormal or missing matrix interactions, any of which should typically induce apoptosis through the intrinsic (mitochondrial) apoptosis pathway. However, rather than respond to these apoptosis signals cancer cells survive. Often, in doing so, these cells become highly dependent on selected blocks to chronic apoptosis signals. This adaptation provides a survival mechanism for the cancer cells; however, these adaptations can also make cancer cells susceptible to particular apoptosis inducing therapies. A crucial event that commits a cell to die by intrinsic apoptosis is the permeabilization of the mitochondrial outer membrane (MOMP) and the release of molecules that activate the effector caspases. In many cases, MOMP is the point of no return in the intrinsic apoptosis pathway. The Bcl-2 family proteins are the key regulators of MOMP, and their activity is linked to the onset of lymphoid and several solid tumor cancers and is believed in many cancers to be the key mediator of resistance to chemotherapy.

Bcl-2 proteins are regulated by distinct protein-protein interactions between pro-survival (anti-apoptotic) and pro-apoptotic members. These interactions occur primarily through BH3 (Bcl-2 homology domain-3) mediated binding. Apoptosis-initiating signaling occurs for the most part upstream of the mitochondria and causes the translocation of short, BH3-only, Bcl-2 family members to the mitochondria where they either activate or sensitize MOMP. The activator BH3 only proteins, Bim and Bid, bind to and directly activate the effector, pro-apoptotic proteins Bax and Bak, and also bind to and inhibit the anti-apoptotic Bcl-2 family proteins, Bcl-2, Mcl-1, Bfl-1, Bcl-w and Bcl-xL. The sensitizer BH3 proteins, Bad, Bik, Noxa, Hrk, Bmf and Puma, bind only to the anti-apoptotic Bcl-2 family proteins, Bcl-2, Mcl-1, Bfl-1, Bcl-w and Bcl-xL, blocking their anti-apoptotic functions. Without wishing to be bound by theory, each sensitizer protein has a unique specificity profile. For example, Noxa (A and B) bind with high affinity to Mcl-1, Bad binds to Bcl-xL and Bcl-2 but only weakly to Mcl-1, and Puma binds well to all three targets. An anti-apoptotic function of these proteins is the sequestering of the activator BH3 protein Bim and Bid. Displacement of these activators by sensitizer peptides results in Bax/Bak-mediated apoptotic commitment. These interactions can have various outcomes, including, without limitation, homeostasis, cell death, sensitization to apoptosis, and blockade of apoptosis.

A defining feature of cancer cells in which apoptotic signaling is blocked is an accumulation of the BH3 only activator proteins at the mitochondrial surface, a result of these proteins being sequestered by the anti-apoptotic proteins. This accumulation and proximity to their effector target proteins accounts for increased sensitivity to antagonism of Bcl-2 family proteins in the "BH3 primed" state.

In some embodiments, a cell yielding a high apoptotic response to Noxa (A or B) is Mcl-1 primed, while a high response to the peptide Bad indicates that Bcl-xL or Bcl-2 provides the apoptotic block. In some embodiments, Puma reflects pan-Bcl-2 family priming. In this way, cells that are dependent on either Mcl-1 or Bcl-xL, on both proteins, or on several Bcl-2 family members are readily distinguished so that appropriate treatment may be tailored accordingly. The distinctions in mitochondrial response to these peptides guides the use of therapies that are known to work through pathways that funnel into either Mcl-1 or Bcl-xL affected intrinsic signaling. The use of a Bcl-2 inhibiting or a Mcl-1 inhibiting compound may be indicated in such cases. In some embodiments, the present methods also indicate or contraindicate therapies that target entities upstream of Mcl-1 or Bcl-xL.

Generation and Production of Antibodies

The antibodies of the present disclosure can be a whole immunoglobulin or a fragment thereof that retains antigen-binding activity. In some embodiments, the antibodies of the present disclosure can be a genetically modified immunoglobulin, including scFv antibody, chimeric antibody, or a humanized antibody. In some embodiments, the antibody or antibody format is selected from one or more of a monoclonal antibody, polyclonal antibody, antibody fragment, Fab, Fab', Fab'-SH, F(ab')2, Fv, single chain Fv, diabody, linear antibody, bispecific antibody, multispecific antibody, chimeric antibody, humanized antibody, human antibody, and a fusion protein comprising the antigen-binding portion of an antibody. In some embodiments, the antibody or antibody format further comprises variable region framework (FW) sequences juxtaposed between the CDRs according to the formula (FW1)-(CDR1)-(FW2)-(CDR2)-(FW3)-(CDR3)-(FW4), wherein the variable region FW sequences in the heavy chain variable region are heavy chain variable region FW sequences, and wherein the variable region FW sequences in the light chain variable region are light chain variable region FW sequences. In some embodiments, the variable region FW sequences are human. The antibody or antibody format can further comprise a human heavy chain and light chain constant regions. In some embodiments, the constant regions are selected from the group consisting of human IgG1, IgG2, IgG3, and IgG4. The term "isolated antibody," as used herein, refers to an antibody substantially free from naturally associated molecules, i.e., the naturally associated molecules constituting at most 20% by dry weight of a preparation containing the antibody.

The antibodies of the present disclosure may be prepared by conventional methods. (See, e.g., Harlow and Lane, (1988) Antibodies: A Laboratory Manual, Cold Spring Harbor Laboratory, New York) For example, a synthetic heterodimer of the Bcl-2 family may be prepared by producing two members of the heterodimer protein separately using a section of a key binding motif, followed by synthesizing the key epitope and inducing a portion of one member of the heterodimer, the ligand, and the full-length protein of the other member of the heterodimer, the receptor. The functionality of the synthetic heterodimer can be checked using in vitro binding assays. Once determined, the binding fidelity is maintained in the synthetic heterodimer, and then the ligand portion can be modified to contain a benzoyl phenylalanine (Anaspec, Fremont, CA, USA) in place of one of several potential aromatic amino acids. (FIG. 1, FIG. 2) Each protein fragment can be further tested for binding fidelity as detailed above. Once selected, the binding ligand can be covalently attached by exposure to activating exposure to UV light at 450 nM for up to 8 hours. The synthetic heterodimer can then be purified by FPLC and be used as an immunogen for injection into a mouse host.

To produce antibodies that bind to the heterodimer, the heterodimer may be optionally coupled to a carrier protein (e.g., KLH) and mixed with an adjuvant, followed by injection into a host animal. Antibodies produced in the animal can then be purified by heterodimer affinity chromatography. Commonly employed host animals include rabbits, mice, guinea pigs, and rats. Various adjuvants may be used to increase the immunological response, which depends on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, are prepared using standard hybridoma technology. (See, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.)) In particular, monoclonal antibodies may be obtained by any technique that provides for the production of antibody molecules by continuous cell lines in culture. (See, Kohler et al. (1975) Nature 256, 495; Kosbor et al. (1983) Immunol Today 4, 72; Cole et al. (1983) Proc. Natl. Acad. Sci. USA 80, 2026, and the EBV-hybridoma technique (Cole et al. (1983); see also Monoclonal Antibodies and Cancer Therapy, Alan R. Liss, Inc., pp. 77-96)) Such antibodies can be of any immunoglobulin class including IgG, IgM, IgE, IgA, IgD, and any subclass thereof. The hybridoma producing the monoclonal antibodies of the present disclosure may be cultivated in vitro or in vivo. The ability to produce high titers of monoclonal antibodies in vivo makes it a particularly useful method of production.

In addition, techniques developed for the production of "chimeric antibodies" can be used. (See, e.g., Morrison et al. (1984) Proc. Natl. Acad. Sci. USA 81, 6851; Neuberger et al. (1984) Nature 312, 604; and Takeda et al. (1984) Nature 314:452) A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946, 778 and 4,704,692) can be adapted to produce a phage or yeast library of scFv antibodies. scFv antibodies are formed by linking the heavy and light chain fragments of the Fv region via an amino acid bridge.

Moreover, antibody fragments can be generated by known techniques. For example, such fragments include, but are not limited to, F(ab') sub.2 fragments that can be produced by pepsin digestion of an antibody molecule, and Fab fragments that can be generated by reducing the disulfide bridges of F(ab') sub.2 fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the present disclosure (see, e.g., Green et al. (1994) Nature Genetics 7, 13; and U.S. Pat. Nos. 5,545,806 and 5,569,825).

Figure 2:
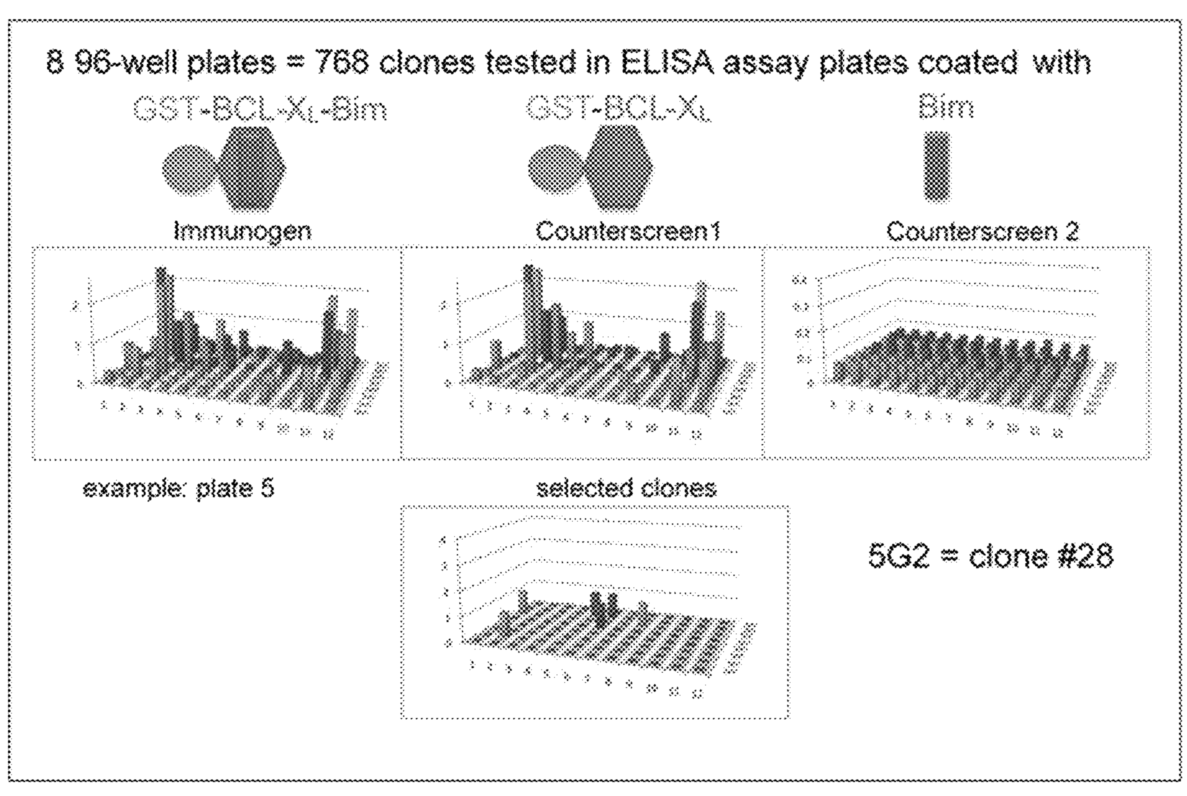
FIG. 2 is a schematic illustration depicting the process of screening and selecting antibodies specific to Bcl-2 heterodimers via an immunoassay. ELISA screening and counter screening of hybridoma supernatants were performed to select a Bcl-xL/Bim heterodimer that binds to a monoclonal antibody (Mab). The left panel shows antibodies binding to a Bcl-2 heterodimer being positively selected. From this screen, 39 selectively binding clones were advanced. The middle panel shows selective binding of mAb-HSBXB to the heterodimer Bcl-xL/Bim BH3: Bcl-xL-GST, which was bound to glutathione-coated ELISA plates. Bim BH3 peptides were added or not (right panel), and HSBXB antibody was used to detect complexes. In these experiments, antibodies binding to non-dimerized members of the heterodimer were negatively selected.
Figure 3:
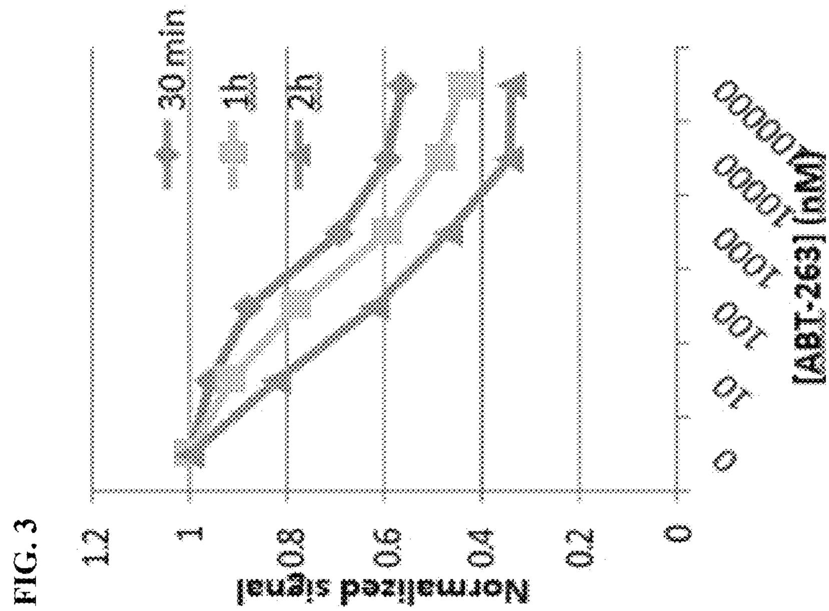
FIG. 3 is a graph showing a non-covalent heterodimer comprising Bcl-xL-GST/Full length BIM protein was bound to Glutathione-coated ELISA plates and treated with ABT-263 (Navitoclax), a BCL2/Bcl-xL targeted compound. The compound was added to the ELISA plates after addition of peptides and before adding the monoclonal antibody. The full length Bim protein was used to form the heterodimer.

The antibodies prepared by any of the methods described above were confirmed for their binding to a Bcl-2 heterodimer. (i.e., see FIG. 3, FIG. 13A, FIG. 13B) They were further subjected to a negative selection to exclude those that also were bound to a non-dimerized member of the heterodimer. (FIG. 2) For example, each of the two members, i.e., monomer A and monomer B, may be labeled with a distinct fluorescent dye, i.e., dye x and dye y, respectively. Dyes x and y have different optimal emission wavelengths. The antibody was first incubated with labeled monomer A, labeled monomer B, or the A/B heterodimer (double labeled) for a suitable period and then captured by Gama-Bind Sepharose beads. Whether the antibody was capable of binding to either monomer or to the heterodimer was determined based on the fluorescent signal released from the captured antibody. Antibodies that bound to the heterodimer and not to either non-dimerized member were selected. (FIG. 2)

Figure 6:
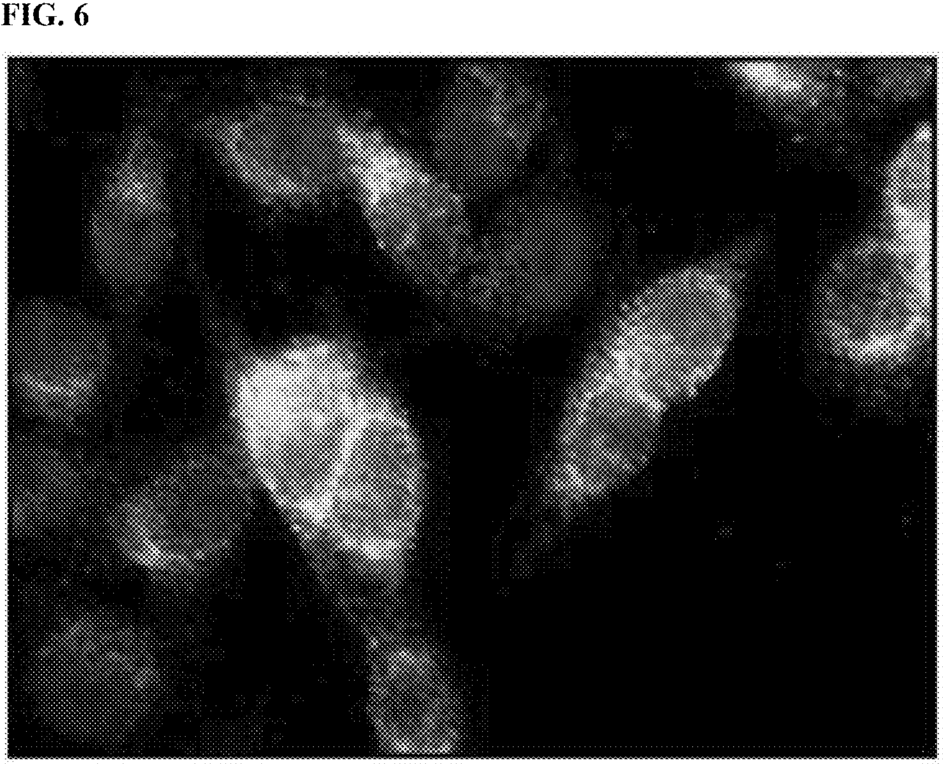
FIG. 6 shows the immunofluorescence signal generated using the antibodies as described in the present disclosure on fixed cells. Immunofluorescence microscopy was used to confirm the utility of HSBXB (e.g., HSBXB clone 32) as a biomarker that could be used in fixed and/or archived tumor samples. Melanoma AUCC903N cells were fixed and permeabilized and incubated with a HSBXB antibody. Bcl-xl-Bim heterodimer (shown in green) and nuclei (DAPI; shown in blue) were then stained in melanoma cells. Fixations were performed using 4% paraformaldehyde and permeabilization with 0.2% TritonX100 buffer. These data show that Bcl-xl-Bim heterodimer was present at the mitochondria, as expected. Importantly, the data establish that the heterodimer antibody can be used to identify priming in adherent samples and direct therapeutic interventions based on results.
Figure 7A:
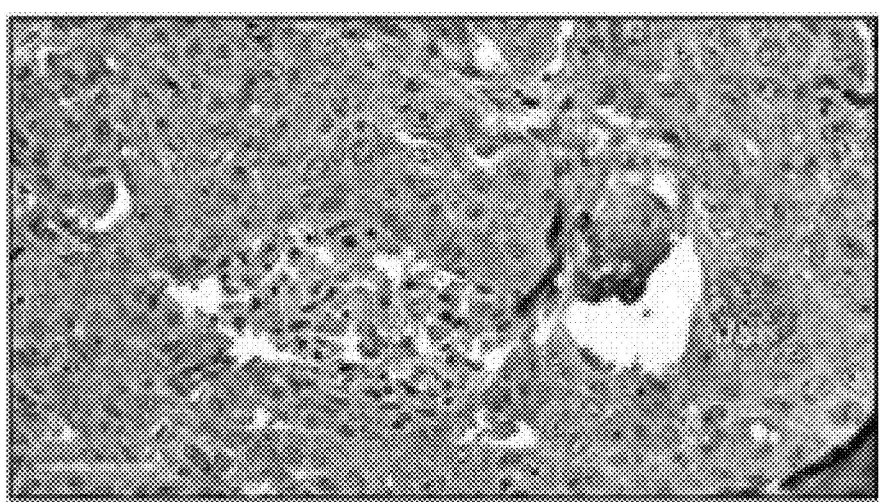
FIG. 7A, FIG. 7B, and FIG. 7C show immunohistochemical (IHC) staining of human tumor biopsies signal generated by using antibodies described in the present disclosure on fixed cells. Fixations were performed using 4% paraformaldehyde, and permeabilization with 0.2% TritonX100 buffer. Immunofluorescence microscopy was used to confirm the utility of HSBXB as a biomarker that could be used in fixed archived tumor samples. Melanoma AUCC903N cells were fixed, permeabilized, and incubated with an HSBXB antibody (FIG. 7A).
Figure 7B:
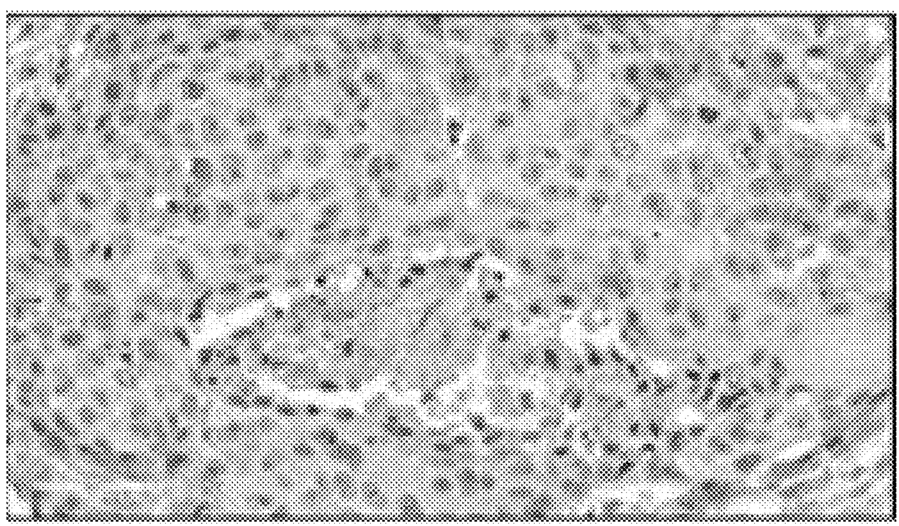
Figure 7C:
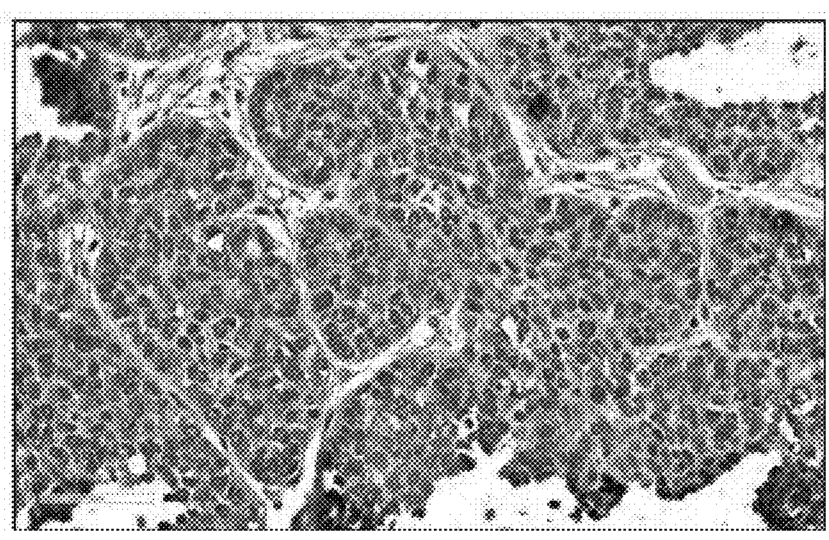

The antibodies disclosed herein can be used in a method of detecting the presence or absence of a Bcl-2 heterodimer in a sample obtained from a subject (e.g., a patient), particularly, a fixed tissue sample or a mitochondrial fraction, by conventional methods, e.g., immunohistochemistry (IHC) staining (FIG. 6). For example, a plurality of antibodies specific to various Bcl-2 heterodimers may be used to profile the presence of particular Bcl-2 heterodimers on the outer membranes of mitochondria in multiple tissue samples from a patient. Tissues at various disease stages (e.g., malignancy stages) can be collected from the same patient. Mitochondrial fractions can be prepared from these tissues and, using a plurality of the antibodies of the present disclosure, the fractions can be profiled for the presence/absence of Bcl-2 heterodimers.

Also disclosed herein is a method of predicting a human patient's responsiveness to a drug that interferes with formation of a particular Bcl-2 heterodimer, directly or indirectly, based on the presence of that Bcl-2 heterodimer in the patient.

It is well known that Bcl-2 proteins play an essential role in regulating apoptosis via formation of heterodimers between members in different Bcl-2 sub-groups. See Table 1 above. An activator BH3-only Bcl-2 protein (i.e., BID or BIM) binds to a multi-domain pro-apoptotic Bcl-2 protein (i.e., BAX or BAK), triggering mitochondrial outer membrane permeabilization (MOMP), which leads to cell death. A multi-domain anti-apoptotic Bcl-2 protein (e.g., Bcl-2 or Mcl-1) can bind to BAX and BAK, and also sequester an activator BH3-only protein from binding to BAX or BAK. Consequently, it blocks the MOMP process, resulting in cell survival. The activity of a multi-domain anti-apoptotic Bcl-2 protein is regulated by the sensitizer BH3-only proteins. This subgroup of Bcl-2 proteins promotes apoptosis by binding to the anti-apoptotic Bcl-2 protein, displacing the activator BH3-only Bcl-2 proteins so that they are released to bind to the pro-apoptotic Bcl-2 proteins, thereby triggering the MOMP process. In short, there are two types of Bcl-2 heterodimers: (1) pro-apoptotic Bcl-2 heterodimers, formed between an activator BH3-only Bcl-2 protein and a multi-domain pro-apoptotic Bcl-2 protein or between a sensitizer BH3-only Bcl-2 protein and a multi-domain anti-apoptotic Bcl-2 protein; and (2) anti-apoptotic Bcl-2 heterodimers, formed between a multi-domain anti-apoptotic Bcl-2 protein and an activator BH3-only Bcl-2 protein or between a multi-domain anti-apoptotic Bcl-2 protein and a multi-domain pro-apoptotic Bcl-2 protein. Formation of pro-apoptotic Bcl-2 heterodimers promotes apoptosis while formation of anti-apoptotic heterodimers promotes cell survival.

The presence of a particular pro- or anti-apoptotic Bcl-2 heterodimer in a subject (e.g., a patient) is known to indicate that patient's responsiveness to a drug that blocks formation of the particular heterodimer and inhibits its function. (See, e.g., Delbridge and Strasser A. Cell Death Differ. 2015 July; 22(7):1071-80. doi: 10.1038/cdd.2015.50)

In some embodiments of the present disclosure, the drug is a mimetic of a BH3-only protein that competes against the BH3-only protein for binding to its cognate partner. In other embodiments, the drug targets an upstream apoptotic factor and ultimately blocks formation of a Bcl-2 heterodimer.

Many cancer drugs induce apoptosis in cancer cells by blocking formation of anti-apoptotic Bcl-2 heterodimers. The presence of a particular anti-apoptotic Bcl-2 heterodimer in a cancer patient indicates that this patient is sensitive to a drug that interferes with formation of this anti-apoptotic Bcl-2 heterodimer. (See Robert et al., Clinical Pharmacology and Therapeutics 101; 1, January 2017). On the other hand, apoptosis inhibitors can be used for treating neurodegenerative disease or cardiovascular disease, both of which involve apoptosis. In this context, the presence of a particular pro-apoptotic Bcl-2 heterodimer in a neurodegenerative disease patient or a cardiovascular disease patient, for example, indicates that such a patient is sensitive to an apoptosis inhibitor that blocks formation of the particular pro-apoptotic Bcl-2 heterodimer.

In some embodiments, the sensitivity is characterized by (a) the presence of apoptosis in the sample; (b) the presence of an anti-apoptotic Bcl-2 heterodimer in the sample, indicating the patient is sensitive to a drug that interferes with formation an anti-apoptotic Bcl-2 heterodimer; (c) genetic risk factors; family history; personal history; race and ethnicity; features of the certain tissues; various benign conditions (e.g. nonproliferative lesions); previous chest radiation; carcinogen exposure and the like.

In some embodiments, the method does not involve a functional readout of mitochondrial outer membrane permeabilization (MOMP). In some embodiments, the method does not involve a dye-based detection of cell membrane potential.

Illustrative Clinical Decisions

In some embodiments, the methods described herein are useful in the evaluation of a solid tumor sample from a patient, for example, for evaluating diagnosis, prognosis, and response to treatment. In various aspects, the present disclosure comprises evaluating a solid tumor. In various embodiments, the evaluation may be selected from diagnosis, prognosis, and response to treatment.

In various aspects, the methods of the present disclosure may be used to treat a cancer patient. For example, the methods may further comprise administering a cancer treatment to the patient if the ratio is predictive of sensitivity to the cancer treatment. In some embodiments, the methods may further comprise treating the patient with a reduced dose or less frequent and/or shortened regimen of the cancer treatment if the ratio is predictive of sensitivity to the cancer treatment. In some embodiments, the methods may further comprise treating the patient with an increased dose or more frequent and/or prolonged regimen of the cancer treatment if the ratio is predictive of sensitivity to the cancer treatment. In some embodiments, the methods may further comprise withholding cancer treatment to the patient if the ratio is predictive of a lack of sensitivity to the cancer treatment. In some embodiments, the methods may further comprise treating the patient with a different cancer treatment if the ratio is predictive of a lack of sensitivity to the cancer treatment.

For instance, in various embodiments, the sample presents a ratio of more dimer than monomer. For instance, the ratio of dimer to monomer may be about 20:1 or about 15:1, or about 10:1, or about 9:1, or about 8:1, or about 7:1, or about 6:1, or about 5:1, or about 4:1, or about 3:1, or about 2:1. In various embodiments, the sample presents a ratio of more monomer than dimer. For instance, the ratio of monomer to dimer may be about 20:1 or about 15:1, or about 10:1, or about 9:1, or about 8:1, or about 7:1, or about 6:1, or about 5:1, or about 4:1, or about 3:1, or about 2:1. In various embodiments, the ratio of dimer to monomer is equivalent (i.e. about 1:1).

Diagnosis refers to the process of attempting to determine or identify a possible disease or disorder, such as, for example, cancer. Prognosis refers to predicting a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and progression free survival, time to progression, and probability of recurrence.

In various embodiments, the present methods direct a clinical decision regarding whether a patient is to receive a specific treatment. In one embodiment, the present methods are predictive of a positive response to neoadjuvant and/or adjuvant chemotherapy or a non-responsiveness to neoadjuvant and/or adjuvant chemotherapy. In one embodiment, the present methods are predictive of a positive response to a pro-apoptotic agent or an agent that operates via apoptosis and/or an agent that does not operate via apoptosis or a non-responsiveness to apoptotic effector agent and/or an agent that does not operate via apoptosis. In various embodiments, the present disclosure directs the treatment of a cancer patient, including, for example, what type of treatment should be administered or withheld.

In some embodiments, the present methods direct a cancer treatment regarding one or more of anti-cancer drugs, chemotherapy, antagonist of an anti-apoptotic protein, surgery, adjuvant therapy, and neoadjuvant therapy.

In one embodiment, the present methods direct a clinical decision regarding whether a patient is to receive adjuvant therapy after primary, main or initial treatment, including, without limitation, a single sole adjuvant therapy. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease.

In some embodiments, the present methods direct a patient's treatment to include adjuvant therapy. For example, a patient that is scored to be responsive to a specific treatment may receive such treatment as adjuvant therapy. Further, the present methods may direct the identity of an adjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as adjuvant therapy. Accordingly, in some embodiments, the present methods provide for providing or withholding adjuvant therapy according to a patient's likely response. In this way, a patient's quality of life, and the cost of care, may be improved.

In various embodiments, the present methods direct a clinical decision regarding whether a patient is to receive neoadjuvant therapy, e.g. therapy to shrink and/or downgrade the tumor prior to surgery. In some embodiments, neoadjuvant therapy means chemotherapy administered to cancer patients prior to surgery. In some embodiments, neoadjuvant therapy means an agent, including those described herein, administered to cancer patients prior to surgery. Types of cancers for which neoadjuvant chemotherapy is commonly considered include, for example, breast, colorectal, ovarian, cervical, bladder, and lung.

In some embodiments, the present methods direct a patient's treatment to include neoadjuvant therapy. For example, a patient that is scored to be responsive to a specific treatment may receive such treatment as neoadjuvant therapy. Further, the present methods may direct the identity of a neoadjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as neoadjuvant therapy. Accordingly, in some embodiments, the present methods provide for providing or withholding neoadjuvant therapy according to a patient's likely response. In this way, a patient's quality of life, and the cost of case, may be improved.

In some embodiments, the present methods direct a clinical decision regarding whether a patient is to receive a specific type of treatment (e.g., one or more of anti-cancer drugs, chemotherapy, antagonist of an anti-apoptotic protein, surgery, adjuvant therapy, and neoadjuvant therapy). In some embodiments, the cancer treatment is one or more of a SMAC mimetic, BH3 mimetic, proteasome inhibitor, histone deacetylase inhibitor, glucocorticoid, steroid, monoclonal antibody, antibody-drug conjugate, or thalidomide derivative. In some embodiments, the present methods are a guiding test for patient treatment.

In some embodiments, the present methods comprise a cancer treatment and the cancer treatment is a checkpoint inhibitor. The checkpoint inhibitor can be an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2. The agent that targets PD-1 can be an antibody or antibody format specific for PD-1, optionally selected from nivolumab, pembrolizumab, and pidilizumab. The agent that targets PD-L1 can be an antibody or antibody format specific for PD-L1, optionally selected from atezolizumab, avelumab, durvalumab, and BMS-936559. The agent that targets CTLA-4 can be an antibody or antibody format specific for CTLA-4, optionally selected from ipilimumab and tremelimumab.

In some embodiments, the present methods provide information about the likely response that a patient is to have to a particular treatment. In some embodiments, the present methods provide a high likelihood of response and may direct treatment, including aggressive treatment. In some embodiments, the present methods provide a low likelihood of response and may direct cessation of treatment, including aggressive treatment, and the use of palliative care, to avoid unnecessary toxicity from ineffective chemotherapies for a better quality of life.

In an illustrative embodiment, the present method will indicate a likelihood of response to a specific treatment. For example, in some embodiments, the present methods indicate a high or low likelihood of response to a pro-apoptotic agent and/or an agent that operates via apoptosis and/or an agent that operates via apoptosis driven by direct protein modulation. In various embodiments, illustrative pro-apoptotic agents and/or agents that operate via apoptosis and/or an agent that operates via apoptosis driven by direct protein modulation include ABT-263 (Navitoclax), and obatoclax, WEP, bortezomib, and carfilzomib. In some embodiments, the present methods indicate a high or low likelihood of response to an agent that does not operate via apoptosis and/or an agent that does not operate via apoptosis driven by direct protein modulation. In various embodiments, illustrative agents that do not operate via apoptosis include kinesin spindle protein inhibitors, cyclin-dependent kinase inhibitor, Arsenic Trioxide (TRISENOX), MEK inhibitors, pomolidomide, azacytidine, decitibine, vorinostat, entinostat, dinaciclib, gemtuzumab, BTK inhibitors, PI3 kinase delta inhibitors, lenolidimide, anthracyclines, cytarabine, melphalam, Aky inhibitors, mTOR inhibitors.

In an illustrative embodiment, the present method will indicate whether a patient is to receive a pro-apoptotic agent or an agent that operates via apoptosis for cancer treatment. In another illustrative embodiment, the present method will indicate whether a patient is to receive an agent that does not operate via apoptosis.

In a specific embodiment, the present methods are useful in predicting a cancer patient's response to any of the treatments (including agents) described herein.

In various embodiments, a cancer treatment is administered or withheld based on the methods described herein. Illustrative treatments include surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics).

Illustrative Treatments

In illustrative embodiments, the disclosure selects a treatment agent. Examples of such agents include, but are not limited to, one or more of anti-cancer drugs, chemotherapy, surgery, adjuvant therapy, and neoadjuvant therapy. In one embodiment, the cancer treatment is one or more of a BH3 mimetic, epigenetic modifying agent, topoisomerase inhibitor, cyclin-dependent kinase inhibitor, and kinesin-spindle protein stabilizing agent. In some embodiments, the BH3 mimetic is selected from ABT-737 and ABT-263 (navitoclax), Bcl-2 specific Venetoclax (Venclexta, ABT-199), MCL-1 specific S63845 and AMG176 and ADZ5991, BCL-XL specific A-1155463 and A1331852, BFL-1/MCL-1 specific EU5346 or combinations thereof. In another embodiment, the cancer treatment is a proteasome inhibitor; and/or a modulator of cell cycle regulation (by way of non-limiting example, a cyclin dependent kinase inhibitor); and/or a modulator of cellular epigenetic mechanistic (by way of non-limiting example, one or more of a histone deacetylase (HDAC) (e.g. one or more of vorinostat or entinostat), azacytidine, decitabine); and/or an anthracycline or anthracenedione (by way of non-limiting example, one or more of epirubicin, doxorubicin, mitoxantrone, daunorubicin, idarubicin); and/or a platinum-based therapeutic (by way of non-limiting example, one or more of carboplatin, cisplatin, and oxaliplatin); cytarabine or a cytarabine-based chemotherapy; a BH3 mimetic (by way of non-limiting example, one or more of BCL2, BCLXL, or MCL1); and an inhibitor of MCL1. In some embodiments, the cancer treatment blocks formation of the particular heterodimer detected. In some embodiments, the cancer treatment perturbs formation of the particular heterodimer detected.

In various embodiments, the disclosure pertains to cancer treatments including, without limitation, one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation, dacogen, velcade, and pharmaceutically acceptable salts, acids or derivatives of any of the above.

Illustrative Detection Methods

In various embodiments, the present methods comprise predicting a patient's sensitivity to a cancer treatment. In some embodiments, the detection of the heterodimer employs an immunohistochemistry (IHC), flow cytometry, or immunofluorescent method.

In various embodiments, the methods involve evaluating a presence, absence, or level of a protein and/or a nucleic acid. In various embodiments, the present methods comprise evaluating a presence, absence, or level of a protein and/or a nucleic acid which can enhance the specificity and/or sensitivity of BH3 heterodimer ratio. In some embodiments, the evaluating is of a marker for patient response. In some embodiments, the present methods comprise measurement using one or more of immunohistochemical staining (i.e., IHC), western blotting, in cell western, immunofluorescent staining, ELISA, and fluorescent activating cell sorting (FACS), or any other method described herein or known in the art. The present methods may comprise contacting an antibody with a tumor specimen (e.g. biopsy or tissue or body fluid) to identify an epitope that is specific to the tissue or body fluid and that is indicative of a state of a cancer.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, CA).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a $F(ab)_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

Illustrative Cancers and Patients

In some embodiments the disclosure provides a method for determining a cancer treatment and/or comprises a patient's tumor or cancer cell specimen. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this disclosure are benign and malignant cancers, as well as dormant tumors or micrometastases. Cancers which migrate from their original location and seed vital organs can eventually lead to the death of the subject through the functional deterioration of the affected organs.

In various embodiments, the disclosure is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods described herein are directed toward the prognosis of cancer, diagnosis of cancer, treatment of cancer, and/or the diagnosis, prognosis, treatment, prevention or amelioration of growth, progression, and/or metastases of malignancies and proliferative disorders associated with increased cell survival, or the inhibition of apoptosis. In some embodiments, the cancer is a solid tumor, including, but not limited to, non-small lung cell carcinoma, ovarian cancer, and melanoma.

In some embodiments, the sample is an infiltrating lymphocyte of the patient.

In some embodiments, the solid tumor is selected from lung cancer, breast cancer, prostate cancer, melanoma, pancreatic cancer, kidney cancer, colon cancer, and ovarian cancer. In some embodiments, the lung cancer is selected from non-small cell lung cancer (NSCLC) and small cell lung cancer (SCLC). In some embodiments, the breast cancer is triple negative breast cancer. In some embodiments, the prostate cancer is androgen independent prostate cancer.

In some embodiments, the disclosure relates to one or more of the following cancers: adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumors, cerebellar astrocytoma, cervical cancer, chronic myeloproliferative disorders, colon cancer, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, lip and oral cavity cancer, liposarcoma, liver cancer, lung cancer (e.g. non-small cell, small cell), medulloblastoma, melanoma, Merkel cell carcinoma, mesothelioma, metastatic squamous neck cancer, mouth cancer, multiple endocrine neoplasia syndrome, mycosis fungoides, myelodysplastic syndromes, myelodysplastic/myeloproliferative diseases, myeloproliferative disorders, chronic, nasal cavity and paranasal sinus cancer, nasopharyngeal carcinoma, neuroblastoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, pleuropulmonary blastoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sezary syndrome, skin cancer (e.g. non-melanoma, melanoma, merkel cell), small cell lung cancer, small intestine cancer, soft tissue sarcoma, squamous cell carcinoma, squamous neck cancer, stomach cancer, supratentorial primitive neuroectodermal tumor, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenstrom macroglobulinemia, and Wilms tumor.

The term subject, as used herein unless otherwise defined, is a mammal, e.g., a human, mouse, rat, hamster, guinea pig, dog, cat, horse, cow, goat, sheep, pig, or non-human primate, such as a monkey, chimpanzee, or baboon. The terms "subject" and "patient" are used interchangeably.

Illustrative Specimens

In some embodiments, the present disclosure includes the measurement of a tumor specimen, including biopsy or surgical specimen samples. In some embodiments, the specimen is selected from a frozen tumor tissue specimen, cultured cells, circulating tumor cells, and a formalin-fixed paraffin-embedded tumor tissue specimen. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen.

In some embodiments, the sample is selected from a tumor biopsy, tissue biopsy, tumor resection, frozen tumor tissue specimen, lymph node, bone marrow, circulating tumor cells, cultured cells, a formalin-fixed paraffin embedded tumor tissue specimen, bronchoalveolar lavage, skin, hair, urine, and combinations thereof. In some embodiments, the tumor biopsy is selected from a core biopsy, needle biopsy, surgical biopsy, and an excisional biopsy.

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen (or biopsy) contains less than 100 mg of tissue, or in certain embodiments, contains about 50 mg of tissue or less. The tumor specimen (or biopsy) may contain from about 20 mg to about 50 mg of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In certain embodiments, the specimen is a human tumor-derived cell line. In certain embodiments, the specimen is a cancer stem cell. In other embodiments, the specimen is derived from the biopsy of a solid tumor, such as, for example, a biopsy of a colorectal, breast, prostate, lung, pancreatic, renal, or ovarian primary tumor.

In certain embodiments, the specimen is of epithelial origin. In some embodiments, the epithelial specimen is enriched by selection from a biopsy sample with an anti-epithelial cell adhesion molecule (EpCAM) or other epithelial cell binding antibody bound to solid matrix or bead.

In certain embodiments, the specimen is of mesenchymal origin. In some embodiments, the mesenchymal specimen is enriched by selection from a biopsy sample with a neural cell adhesion molecule (N-CAM) or neuropilin or other mesenchymal cell binding antibody bound to a solid matrix or bead.

In some embodiments, the specimen is derived from a circulating tumor cell.

Illustrative Clinical Factors and Additional Biomarkers

In some embodiments, the disclosure comprises determining one or more clinical factors of the patient. The disclosure can comprise detecting a heterodimer comprising two B-cell lymphoma 2 (BCL-2) proteins in a solid tumor sample from a patient, and determining a ratio of the heterodimer and/or clinical factors to assess a patient response or predict a patient's sensitivity to cancer treatment. In some embodiments, the clinical factor comprises further classifying the patient for likelihood of clinical response to the cancer treatment based on one or more clinical factors of the patient. In some embodiments, the clinical factor comprises comparing the prediction of the patient's sensitivity to the cancer treatment with the likelihood of clinical response to the cancer treatment based on one or more clinical factors of the patient. In some embodiments, a clinical factor that provides patient response information in combination with the ratio study may not be linked to apoptosis. In some embodiments, a clinical factor is non-apoptosis affecting.

In some embodiments, the clinical factor is one or more of age, cytogenetic status, performance, histological subclass, gender, and disease stage. In some embodiments, the clinical factor further comprises measuring an additional biomarker selected from mutational status, single nucleotide polymorphisms, steady state protein levels, and dynamic protein levels.

In one embodiment, the clinical factor is age. In one embodiment, the patient age profile is classified as over about 10, or over about 20, or over about 30, or over about 40, or over about 50, or over about 60, or over about 70, or over about 80 years old.

In one embodiment, the clinical factor is cytogenetic status. In some cancers, such as Wilms tumor and retinoblastoma, for example, gene deletion or inactivation are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemia's, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the ERBB2 gene, which codes for human epidermal growth factor receptor 2. Also, gains in chromosomal number, such as chromosomes 1q and 3q, are also associated with increased cancer risk.

Cytogenetic status can be measured in a variety of manners known in the art. For example, FISH, traditional karyotyping, and virtual karyotyping (e.g. comparative genomic hybridization arrays, CGH and single nucleotide polymorphism arrays) may be used. For example, FISH may be used to assess chromosome rearrangement at specific loci and these phenomena are associated with disease risk status. In some embodiments, the cytogenetic status is favorable, intermediate, or unfavorable.

In one embodiment, the clinical factor is performance. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self-care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In one embodiment, the clinical factor is histological subclass. In some embodiments, histological samples of tumors are graded according to Elston & Ellis, Histopathology, 1991, 19:403-10, the contents of which are hereby incorporated by reference in their entirety.

In one embodiment, the clinical factor is gender. In one embodiment, the gender is male. In another embodiment the gender is female.

In one embodiment, the clinical factor is disease stage. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In another embodiment, the method further comprises a measurement of an additional biomarker selected from mutational status, single nucleotide polymorphisms, steady state protein levels, and dynamic protein levels. In another embodiment, the method further comprises predicting a clinical response in the patient. In another embodiment, the clinical response is about 1, about 2, about 3, or about 5-year progression/event-free survival.

A variety of clinical factors have been identified, such as age profile and performance status. A number of static measurements of diagnosis have also been utilized, such as cytogenetics and molecular events including, without limitation, mutations in the genes MLL, AML/ETO, Flt3-ITD, NPM1 (NPMc+), CEBPα, IDH1, IDH2, RUNX1, ras, and WT1 and in the epigenetic modifying genes TET2 and ASXL, as well as changes in the cell signaling protein profile.

In some embodiments, the preventive methods comprise administering a treatment to a patient that is likely to be afflicted by cancer as guided by the methods described herein. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, exposure to a cancer-inducing agent (e.g. an environmental agent), and pharmacogenomics information (the effect of genotype on the pharmacokinetic, pharmacodynamic or efficacy profile of a therapeutic).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic clinical factor, as is known in the art. Such clinical factors may include, by way of example, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, or 2, or 3, or 4, or 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a clinical factor for skin cancer. By way of example, smoking is a clinical factor for cancers of the lung, mouth, larynx, bladder, kidney, and several other organs.

Further, in some embodiments, the any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

Further still, in some embodiments, the any one of the following clinical factors may be useful in the methods described herein: one or more of a cell surface marker CD33, a cell surface marker CD34, a FLT3 mutation status, a p53 mutation status, a phosphorylation state of MEK-1 kinase, and phosphorylation of serine at position 70 of Bcl-2.

In some embodiments, the clinical factor is expression levels of the cytokines, including, without limitation, interleukin-6. In some embodiments, interleukin-6 levels will correlate with likelihood of response in MM patients, including a poor patient prognosis or a good patient prognosis.

In some embodiments, the likelihood of response is determined by assessing a percent priming. In certain embodiments, the priming is defined by the following equation:

$$\%\ \text{Priming} = \left[100 * \left(\frac{\text{negative control } AUC - Peptide_1 AUC}{\text{negative control } AUC - \text{Positive } Control_{avg} AUC}\right)\right] Peptide_1 + \left[100 * \left(\frac{\text{negative control } AUC - Peptide_2 AUC}{\text{negative control } AUC - \text{Positive } Control_{avg} AUC}\right)\right] Peptide_2 + \ldots / (n \text{ peptides})$$

wherein:

the AUC (area under a curve) is a sum of fluorescence measurements established by homogenous time-resolved fluorescence (HTRF) or mean signal intensity from fluorescence activated cell sorting (FACS), wherein the signal intensity is a single time point measurement that occurs between about 5 min and about 300 min after the start of priming;

the negative control comprises a baseline negative control for either an area under a curve or a signal intensity;

the positive control comprises a baseline positive control for either an area under a curve or a signal intensity (e.g., any uncoupling agent); and the Peptide is one or more BH3 domain peptides, wherein (n) is normalized with the average number of replicates of the negative and positive controls.

In some embodiments, in combination with the preceding equation, the one or more clinical factors are selected to increase specificity and/or sensitivity of the BH3 profile for association with clinical response.

In some embodiments, the likelihood of response is determined by assessing a percent priming. In certain embodiments, the priming is defined by the following equation:

$$\%\ \text{Priming} = \left[100 * \left(\frac{DMSO\ AUC - Peptide_1 AUC}{DMSO\ AUC - CCCP_{avg} AUC}\right)\right] Peptide_1 + \left[100 * \left(\frac{DMSO\ AUC - Peptide_2 AUC}{DMSO\ AUC - CCCP_{avg} AUC}\right)\right] Peptide_2 + \ldots / (n \text{ peptides})$$

wherein:

the AUC (area under a curve) is a sum of fluorescence measurements established by homogenous time-resolved fluorescence (HTRF) or mean signal intensity from fluorescence activated cell sorting (FACS), wherein the signal intensity is a single time point measurement that occurs between about 5 min and about 300 min after the start of priming;

the DMSO (Dimethyl sulfoxide) comprises a baseline negative control for either an area under a curve or a signal intensity;

the CCCP (Carbonyl cyanide m-chlorophenyl hydrazone) is a chemical inhibitor of oxidative phosphorylation and comprises an effector of protein synthesis by serving as uncoupling agent of the proton gradient established during the normal activity of electron carriers in the electron transport chain in the mitochondria, and the CCCP comprises a baseline positive control; and the Peptide is one or more BH3 domain peptides, wherein (n) is normalized with the average number of replicates of the DMSO and CCCP controls.

In some embodiments, in combination with the preceding equation, the one or more clinical factors are selected to increase specificity and/or sensitivity of the BH3 profile for association with clinical response.

In some embodiments, the likelihood of clinical response is defined by a simplified form of the preceding equation, as shown here:

$$\%\ \text{Priming} = \left[100 * \left(\frac{DMSO_{avg} AUC - Peptide_n AUC}{DMSO_{avg} AUC - CCCP_{avg} AUC}\right)\right]$$

wherein:

the AUC (area under a curve) is a sum of fluorescence measurements established by homogenous time-resolved fluorescence (HTRF) or mean signal intensity from fluorescence activated cell sorting (FACS), wherein the signal intensity is a single time point measurement that occurs between about 5 min and about 300 min after the start of priming;

the DMSO (Dimethyl sulfoxide) comprises a baseline negative control for either an area under a curve or a signal intensity;

the CCCP (Carbonyl cyanide m-chlorophenyl hydrazone) is a chemical inhibitor of oxidative phosphorylation and comprises an effector of protein synthesis by serving as uncoupling agent of the proton gradient established during the normal activity of electron carriers in the electron transport chain in the mitochondria, and the CCCP comprises a baseline positive control; and the Peptide is one or more BH3 domain peptides, wherein (n) is normalized with the average number of replicates of the DMSO and CCCP controls.

In some embodiments, in combination with the preceding equation, the one or more clinical factors are selected to increase specificity and/or sensitivity of the BH3 profile for association with clinical response.

In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS). In some embodiments, the signal intensity is a single time point measurement that occurs between about 5 min and about 300 min.

In some embodiments, the present disclosure provides a method for predicting a patient's responsiveness to a checkpoint inhibitor in a sample, comprising measuring the amount of a Mcl-1/Bim or a BCLXL/Bim heterodimer, wherein the sample comprises an infiltrating lymphocyte population from a solid tumor. The checkpoint inhibitor can an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2. The agent that targets PD-1 can be an antibody or antibody format specific for PD-1, optionally selected from nivolumab, pembrolizumab, and pidilizumab. The agent that targets PD-L1 can an antibody or antibody format specific for PD-L1, optionally selected from atezolizumab, avelumab, durvalumab, and BMS-936559. The agent that targets CTLA-4 can be an antibody or antibody format specific for CTLA-4, optionally selected from ipilimumab and tremelimumab.

In some embodiments, the present disclosure provides a polynucleotide comprising a nucleic acid sequence encoding the antibody or antibody fragment. In some embodiments, a vector comprising the polynucleotide provided; in some embodiments, a host cell comprising the vector is provided.

In some aspects, the present disclosure provides a pharmaceutical composition comprising the antibody or antibody format of any of the antibodies disclosed herein and a pharmaceutically acceptable excipient.

The disclosure also provides kits that can simplify the evaluation of tumor or cancer cell specimens. A typical kit of the disclosure comprises various reagents including, for example, one or more agents (e.g., an antibody as disclosed herein) useful to detect a heterodimer. The kit can further comprise materials necessary for the evaluation, including welled plates, syringes, and the like. The kit can further comprise a label or printed instructions instructing the use of described reagents. The kit can further comprise a treatment to be tested.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or less than 1%. Importantly, all recitations of a reference value preceded by the term "about" are intended to also be a recitation of the reference value alone. Notwithstanding the preceding, in this application the term "about" has a special meaning with regard to pharmacokinetic parameters, such as area under the curve (including AUC, $AUC_t$, and $AUC_\infty$) $C_{max}$, $T_{max}$, and the like. When used in relationship to a value for a pharmacokinetic parameter, the term "about" means from 85% to 115% of the reference parameter.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

This disclosure is further illustrated by the following non-limiting examples.

EXAMPLES

Example 1: Preparation of Monoclonal Antibodies Specific to Bcl-2 Heterodimers Genes encoding human Bcl-xL, Bcl-2, and Mcl-2 were cloned and mutated to delete their transmembrane domains. The mutated genes were then linked to a nucleotide sequence encoding Glutathione-S-transferase (GST) and cloned into pGEX 4T-1 to obtain DNA constructs for expressing Bcl-xL(Δ)-GST, Bcl-2(Δ)-GST, and Mcl-2(Δ)-GST fusion proteins. DNA constructs for expressing full length human Bax, Bak, Bak, Bim, Bid, Bad, Puma, and Noxa, all fused with GST, were prepared by recombinant technology.

All of the DNA constructs were introduced into BL21 (D3) chemically competent *E. coli* cells. Positive transformants were cultured in a suitable medium and expression of the fusion proteins were induced with isopropyl-1-thio-β-D-galactopyranoside. The expressed fusion proteins were purified using Amersham Hitrap Glutathion e column on the ACTA-FPLC (Amersham) and accurately quantified using spectrophotometry.

Bcl-xL(Δ)-GST, Bcl-2(Δ)-GST, or Mcl-2(Δ)-GST were then mixed with Bax-GST, Bak-GST, Bak-GST, Bim-GST, Bid-GST, Bad-GST, Puma-GST, or Noxa-GST at equamolar amounts in PBS.

Aromatic amino acids within the Bim BH3 peptides were derivatized with BPA as described in Table 2. Each of these peptides were tested for binding affinities using fluorescence polarization as Richard, D. J.; et al. Bioorg. Med. Chem. (2013),

TABLE 2

Bim BH3 domain containing peptides used to make heterodimer

| Sequences: | U = bpa; Bpa = 4-benzoylphenylalanine |
|---|---|
| 1 | IUIAQELRRIGDEFNAYYARR |
| 2 | IWIAQELRRIGDEFNAUYARR |
| 3 | IWIAQELRRIGDEFNAYUARR |
| 4 | IWIAQELRRIGDEUNAYYARR |

Selected peptides were then coupled to purified GST-anti-apoptotic Bcl-2 family fusion proteins by exposing the UV light, (450 nM), for 8 hours at room temperature. The heterodimers were purified using a sepharose 12 column (Pharmacia) on a ACTA-FPLC (Amersham), following the method described in Zue et al., Protein Science 6: 781-788 (2007).

Each of the heterodimers (2.mg) was then suspended in monophosphoryl lipid A plus trehalose dicorynomycolate adjuvant (Ribi Immunochem. Research Inc., Hamilton, Mont.). The formed mixture was then injected into Balb/c mice at each hind foot pad once every 3-4 days for 14 times. Three days after the final injection, spleen cells were removed from the mice and a single cell suspension is prepared in a DMEM medium (Gibco/BRL Corp.) supplemented with 1% penicillin-streptomycin. The spleen cells were fused with murine myeloma cells P3X63AgU.1 (ATCC CRL 1597) using 35% polyethylene glycol and cultured in 96-well culture plates.

Hybridomas were selected in super DMEM (DMEM supplemented with 10% fetal calf serum FCS, 100 mM pyruvate, 100 U/ml insulin, 100 mM oxaloacetic acid, 2 mM glutamine, 1% nonessential amino acids (GIBCO/BRL), 100 U/ml penicillin, and 100 μg/ml streptomycin] containing 100 μM hypoxanthine, 0.4 μM aminopterin, and 16 μM thymidine (HAT), (Sigma Chemical Co., St. Louis, Mo.).

Hybridoma cells were fed with 200 μl of super DMEM containing 10% FCS and antibiotics. Ten days after the fusion, supernatants of the hybridoma cultures were collected and screened for the presence of antibodies that were bound to the cognate heterodimer protein and/or to either member of the heterodimer (as negative controls) in a capture ELISA as described in Certo et al., Cancer Cell., 9(5):351-365 (2006).

Briefly, 96-well microtiter plates (Maxisorb; Nunc, Kamstrup, Denmark) were coated with 50 μl (1 μg/ml) of a heterodimer or a member of the heterodimer at 4° C. overnight. The plates were then washed three times with PBS containing 0.05% TWEEN 20™ (PBST) and blocked with 50 μl PBS containing 2.0% bovine serum albumin (BSA) at room temperature for 1 hour. The plates were then washed again three times with PBST. Afterwards, 100 μl of a hybridoma supernatant was added to designated wells. The plates were incubated at room temperature for 1 hour on a shaker apparatus and then washed three times with wash buffer. Next, 50 μl of HRP-conjugated goat anti-mouse IgG Fc (Cappel Laboratories), diluted 1:1000 in assay buffer (0.5% bovine serum albumin, 0.05% % TWEEN 20™, 0.01% Thimersol in PBS), was added to each well. The plates were then incubated for 1 hour at room temperature on a shaker apparatus and washed three times with wash buffer, followed by addition of 50 μl of substrate DACO and incubation at room temperature for 10 minutes. 50 μl of diethyl glycol was added to each well to stop the reaction and absorbance at 450 nm in each well is read in a microliter plate reader.

Hybridoma cells producing antibodies that bind to a heterodimer but not to either member of the heterodimer were then selected. These positive hybridoma cells were cloned twice and the specificity of the produced antibodies were retested. The isotypes of the antibodies having the desired specificity were determined by conventional methods, e.g., using isotype specific goat anti-mouse IgGs (Fisher Biotech, Pittsburgh, Pa.). The specificity of the antibodies in each antiserum was examined by conventional methods, e.g., the immunoprecipitation and FACS assays described in Examples 4 and 5 below.

Example 2: Screening for scFv Antibodies Specific to Bcl-2 Heterodimers Using a Yeast scFv Library A nonimmune human scFv yeast library (using expression vector pYD1) was obtained from Pacific Northwest National Laboratories. In this library, a scFv antibody, in which the heavy and light chains were connected by a flexible polypeptide linker were fused to the adhesion subunit of the yeast agglutinin protein Aga2p and the HA-tag protein. Upon expression, the scFv was located on the surface of a yeast host cell via binding of Aga2P to Aga1P, a cell surface protein (FIG. 4A-D). Each yeast cell typically displayed $1\times10^5$ to $1\times10^6$ copies of the scFv and the surface expression of the scFv. Variations in surface expression can be measured through immunofluorescence labeling of the HA-tag flanking the scFv region (FIG. 4 A-D).

The scFv library described above was introduced into yeast strain EBY100 (Invitrogen) and scFv antibodies having the desired specificity were identified as follows. The EBY yeast cells was first grown overnight in 1 liter of SDCAA medium (containing 20 g dextrose, 6.7 g Difco yeast nitrogen base, 5 g Bacto casamino acids, 5.4 g $Na_2HPO_4$ and 8.56 g $NaH_2PO_4H_2O$). $1\times10^{10}$ yeast cells from the overnight culture were precipitated by centrifugation at 2,500 g for 5 minutes and resuspended in SGCAA medium (a medium identical to SDACC except that it contains galactose instead of dextrose) to an absorbance of about 0.5-1 at 600 nm. The yeast cells were then cultured at 20° C. for 36 h to allow expression of scFv antibodies. Afterwards, the cells are collected by centrifugation at 2,500 g for 5 min. The cell pellet is washed with 25 ml PBS.

Yeast cells expressing scFv antibodies were sorted by flow cytometry. Briefly, about $1\times10^6$ to $1\times10^7$ yeast cells were prepared as described above and collected via centrifugation at 14,000 g for 30 seconds, washed with 1 ml PBS buffer, and mixed with 2 μl of 10 μg/ml anti-HA phycoerythrin monoclonal antibody (SIGMA-ALDRICH) and Bcl-2/Bid heterodimer, in which Bcl-2 was labeled with FITC and Bid was labeled with Texas red. After being incubated at room temperature for 1 hour, the mixture was centrifuged at 12,000 g for 30 seconds to precipitate yeast cells. The cell pellet was then resuspended in 500 μl 10 mM Tris (final cell density about $10^6$/ml) and subjected to cell sorting by flow cytometry as follows.

A flow cytometry protocol was pre-determined using EBY100 yeast cells mixed with the anti-HA phycoerythrin antibody as a positive control and EBY100 yeast cells were mixed with the double-labeled heterodimer as a negative control. Compensation was performed to reject crosstalk between the FITC, Texas red, and phycoerythrin channels of the fluorescence detector. The labeled yeast cells were loaded into a FACS Aria Cell-Sorter (Becton Dickinson, Mountain View, Calif.) and gated on forward- and side scatter channels. An appropriate sort gate in the FITC/Texas red/phycoerythrin positive quadrant was drawn and the top 5% triple positive yeast cells were collected in 1 ml SDCAA media. If necessary, the top 0.1% triple-positive yeast cells were collected to ensure that only cells having high affinity to Bcl-2/Bid heterodimer were sorted.

The identified triple-positive cells were suspended in 10 ml SDCAA and grown over night at 30° C. These cells are then subjected to two rounds of negative selection to exclude cells expressing scFv antibodies that also bind to Bcl-2 or Bid monomer. More specifically, the cells were incubated with FITC-labeled Bcl-2 and Texas red-labeled Bid and following the same procedure described above, FITC and Texas red double negative cells were sorted. The collected cells were labeled with the double-labeled Bcl-2/Bid heterodimer to confirm their binding to the heterodimer.

The identified yeast cells were then diluted and plated to allow formation of individual clones. Plasmid DNAs were isolated from these clones using a Zymoprep kit (Zymo Research, Orange, Calif.) as described in Weaver-Feldhaus et al., Protein Engineering, Design & Selection vol. 18, no. 11, pp 527-536 (2005). The scFv sequence included in each plasmid DNA was determined following the method described in Chao et al., Nature Protocols 1:755-768 (2006).

The identified scFv antibodies were analyzed by ELISA and FACS to confirm their specificity to Bcl-2/Bid heterodimer. The antibodies were then subjected to mutagenesis to select for scFv antibodies having higher affinity and specificity to Bcl-2/Bid heterodimer.

Example 3: Selection of Antibodies Specific to Bcl-2 Heterodimers by Immunoprecipitation Immunoassays (i.e., ELISA, immunoprecipitation assay) were performed to confirm that the antibodies from Example 1 were specific to Bcl-2 heterodimers. (FIG. 2, FIG. 13A, FIG. 13B) Two members of a Bcl-2 heterodimer were conjugated with two fluorescent probes that had distinct emission spectra, i.e., one labeled with fluorescein isothiocyanate (FITC; which emits at 488 nm) and the other labeled with Texas red (which emits at 590 nm). (FIG. 4 A-D) The labeled members were incubated together to allow formation of the Bcl-2 heterodimer, following the method described in Example 1 above. In the experiments of this example, 0.1 g of the heterodimer formed when incubated with 0.5 mL PBS containing 0.05% tween-20 and 50 μL of supernatant from a hydridoma clone that produced an antibody of interest. The non-dimerized labeled members of the heterodimer were used as negative controls. The mixtures were then incubated for 1 hour on ice to allow formation of antibody-antigen complexes, and then 10 μl of GammaBind-G sepharose beads (GE Healthcare, Piscataway, N.Y.) were added to the mixture. After being incubated on ice for 30 minutes on ice with rotation, the mixtures were centrifuged at 10,000×g for 30 seconds. The pelleted beads, which had the antibody-antigen complexes attached, were then washed several times and measured for optical density at OD of 488 nm and an OD of 590 nm. The specificity of the antibody was then determined based on the values of the OD of 488 nm and an OD of 590 nm.

Example 4: Selective Binding and Inhibition of a BIM-BH3 Induced Epitope

Figures 13A, 13B:
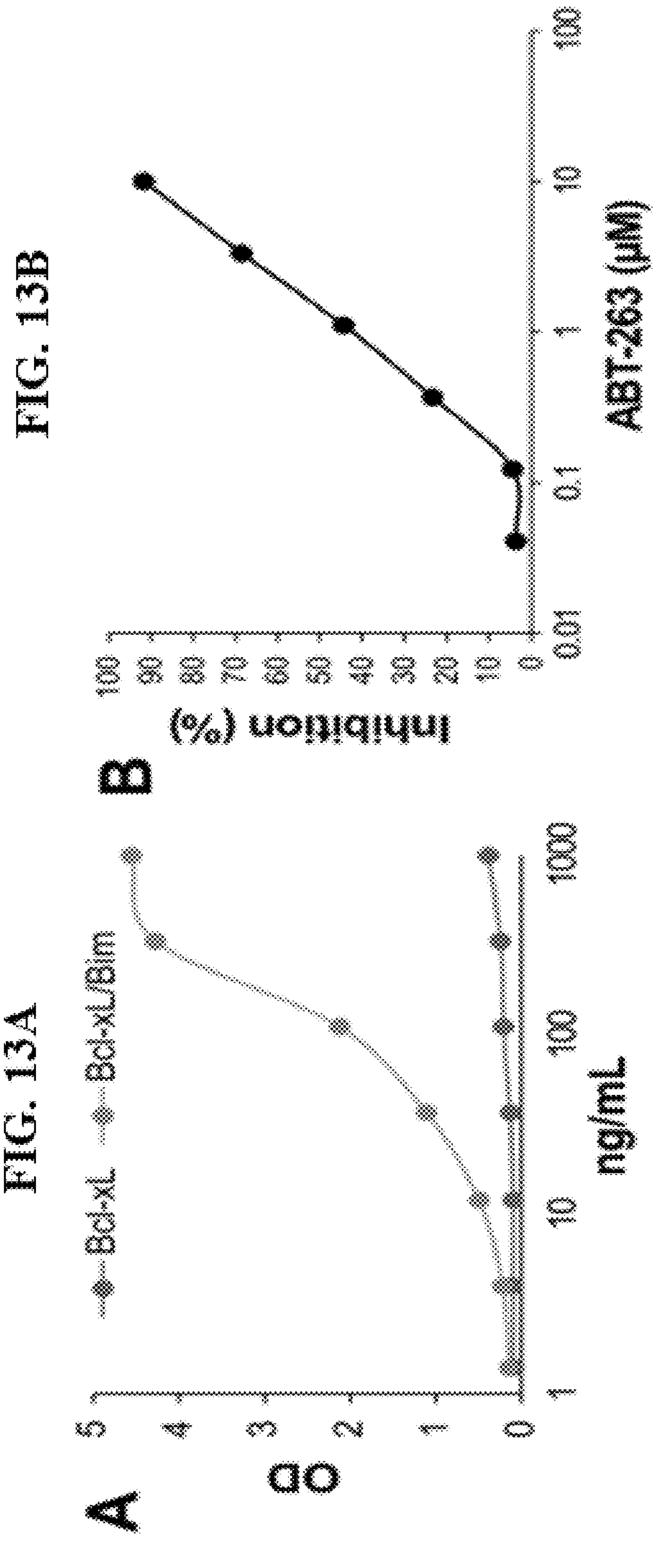
FIG. 13A and FIG. 13B are graphs showing the selective binding of the HSBXB antibody to the Bcl-XL/BIM-BH3 heterodimer.

A monoclonal antibody was then prepared, which is disclosed herein as Heterodimer Specific, Bcl-xL Bim (HSBXB). HSBXB specifically bound to a heterodimer of Bcl-xL and Bim-BH3 domain peptide. To further characterize HSBXB, the antibody was assessed under conditions where Bcl-xL/Bim binding, mediated by the BH3 domain of Bim, was inhibited. ABT-263 is a BH3 domain mimetic that competitively inhibits BH3 domain mediated binding. ABT-263 disrupts Bcl-xL interactions with pro-death proteins (e.g., Bim), leading to the release of Bim from the heterodimer, and resulting in the initiation of apoptosis. When ABT-263 was added, a dose-dependent inhibition of heterodimer antibody signal was observed in heterodimers formed with a peptide comprising the BH3 domain of Bim. Bid-BH3 domain peptide, or no peptide, served as negative controls confirming a heterodimer specificity of the monoclonal antibody. FIG. 3C, FIG. 13A, and FIG. 13B show the results for selective binding of Mab HSBXB to heterodimer Bcl-xL/Bim-BH3. In the experiment shown in FIG. 13A, Bcl-xL-GST was bound to glutathione-coated ELISA plates. Bim-BH3 peptide was then added, or not added as a control, and HSBXB antibody was used to detect complex formation. FIG. 13B shows inhibition of binding by ABT-263. Non-covalent Bcl-xL-GST/Bim BH3 heterodimer was bound to glutathione-coated ELISA plates and treated with ABT-263. ABT-263 was then added to the ELISA plates after addition of peptides and before adding the monoclonal antibody. FIG. 13B demonstrates that ABT263 mediated displacement of the Bcl-xL bound Bim BH3 peptide, which was reflected in a loss of HSBXB binding. The results of this experiment indicate highly selective binding of BH3 peptide to the heterodimer, which correlates to the extent of BH3 peptide binding and demonstrates a dynamic range of binding. A dose-dependent inhibition of heterodimer antibody signal was observed in heterodimers formed with the Bim peptide, BID peptide, or full length Bim protein. ABT263 displaced the Bcl-xL bound Bim and of HSBXB binding. Select Antibodies Specific to Bcl-2/Bim FIG. 3C.

Example 5: Detection of Bcl-xL Bim Heterodimer in Cells and in Tissue

Figure 4A:
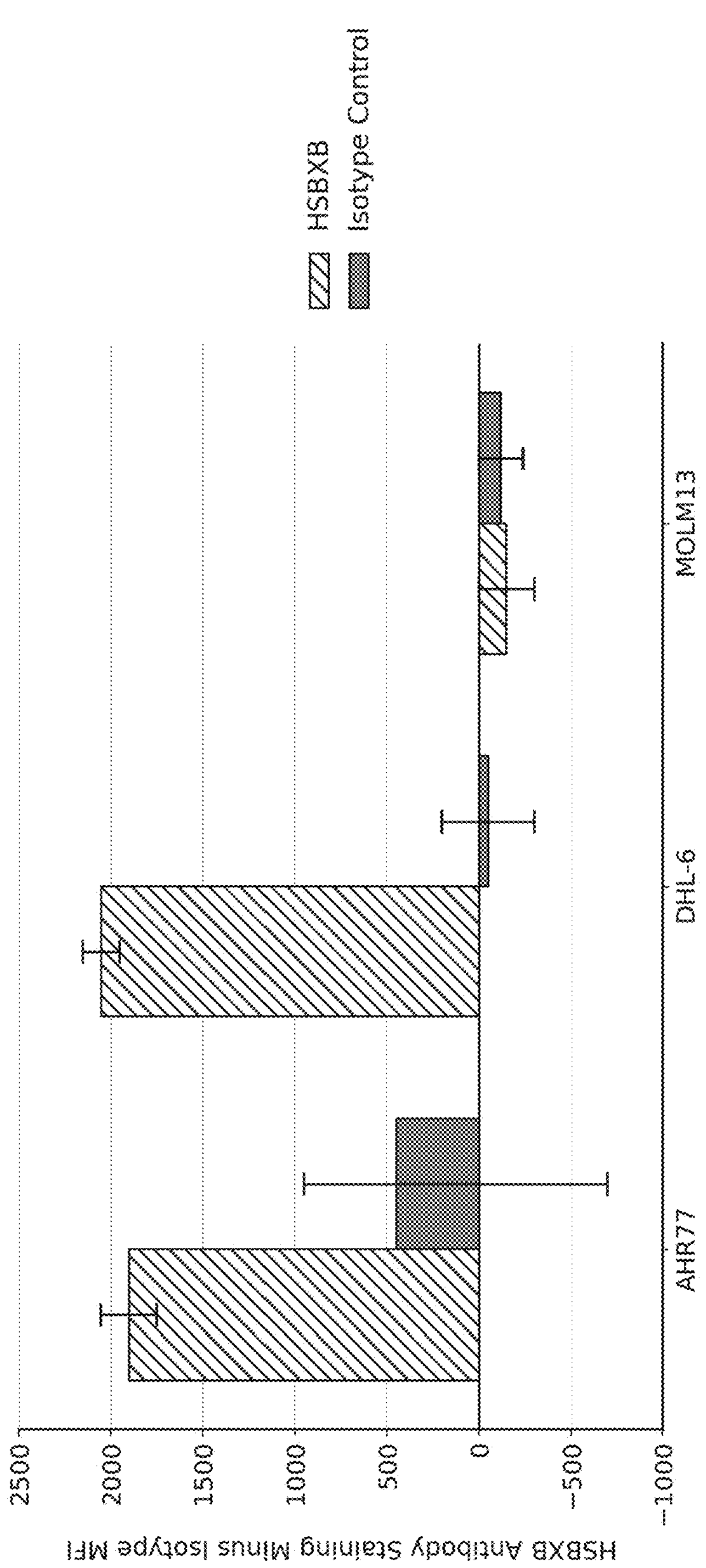
FIG. 4A, FIG. 4B, FIG. 4C, and FIG. 4D show the detection of a Bcl-XL/Bim heterodimer by flow cytometry and immunofluorescence (IF), and demonstrate that the ELISA HSBXB signal correlates with the mitochondrial BH3 profiling readout.
Figure 4B:
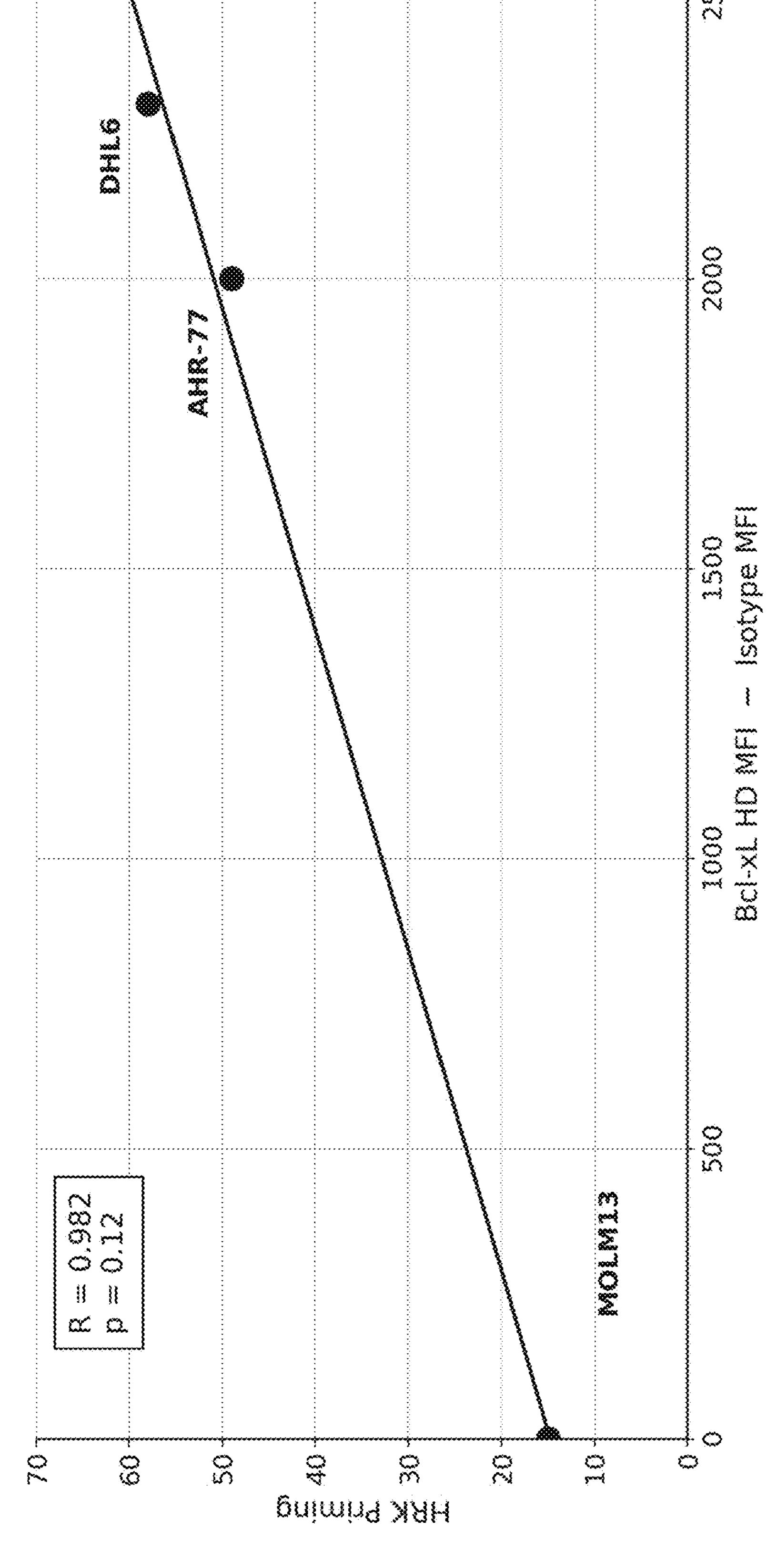
Figure 4C:
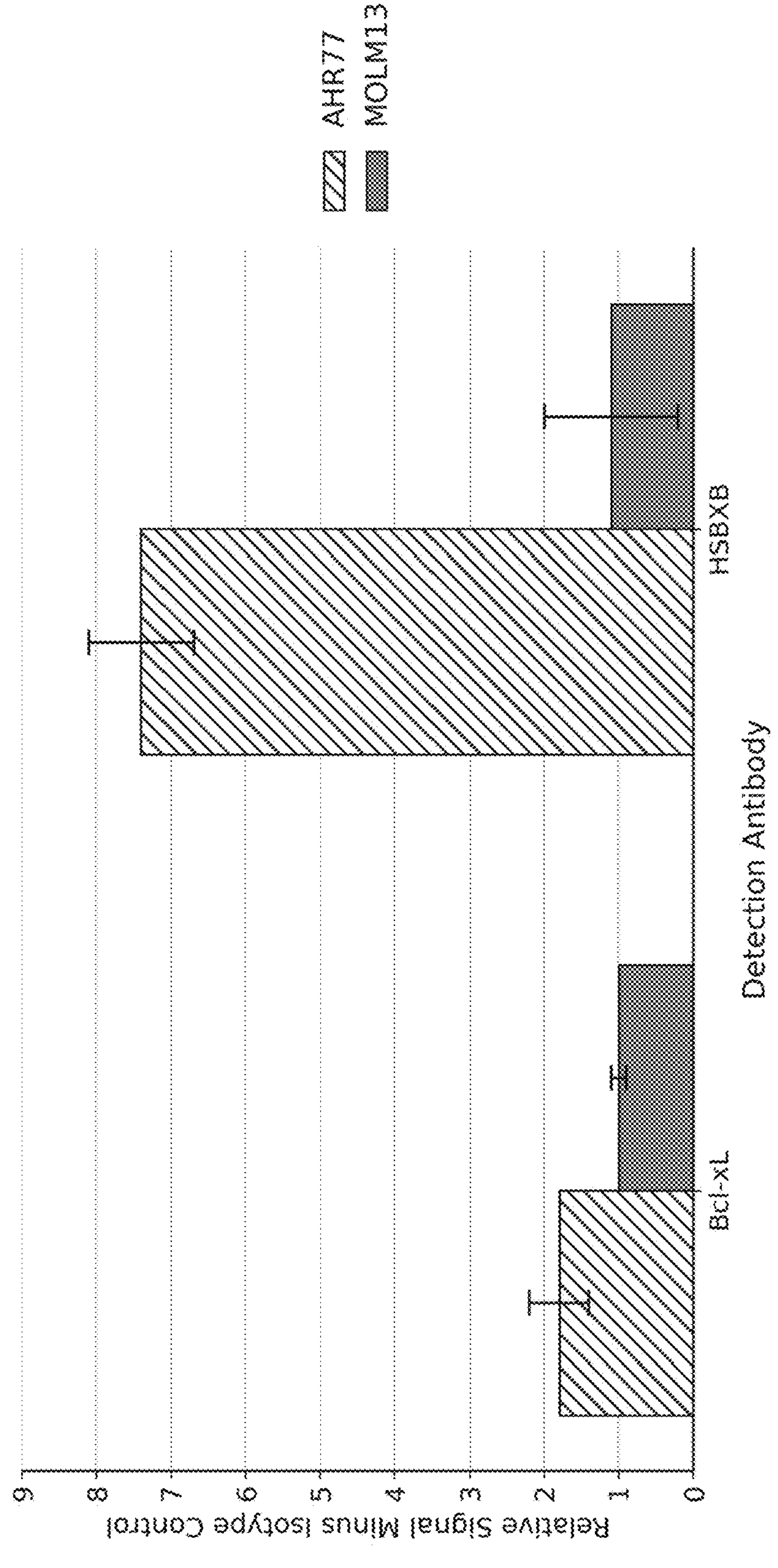
Figure 4D:
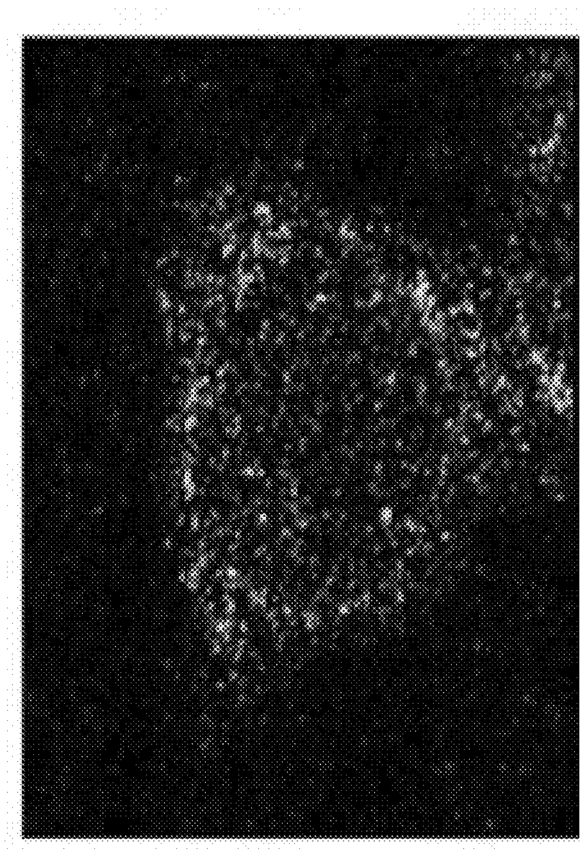

Disclosed herein is the establishment of a method for intracellular staining using the HSBXB antibody, as well as for the use of HSBXB to investigate the functionality of the antibody in determining the priming state of cancer cells. Three cell lines were chosen with varying degrees of Bcl-xL, Bim priming (FIG. 4B, y-axis) as determined by probing cells with a Hrk BH3 domain peptide (biomarker for Bcl-xL dependency). The cell lines, Molm-13, AHR77, and DHL-6 were 17%, 50%, and 60% Bcl-xL (Hrk) primed respectively, and correlation (R=0.982) between the Hrk priming and HSBXB antibody staining was observed (FIG. 4A and FIG. 4B). Also, to confirm the flow cytometric detection of the HSBXB staining, a sandwich ELISA based approach was utilized to capture bound Bcl-xL heterodimer to a plate coated with Bcl-xL antibody, then detected using the HSBXB antibody (FIG. 4C). This approach showed the same staining trend of HSBXB as seen with flow cytometry, and as described in (Pierceal, W. E. et al. Mol Cancer Ther. 2013 December; 12(12):2940-9). Additionally, to demonstrate the detection of the Bcl-xL/Bim heterodimer by IF, SKBR3 cells fixed in 2% PFA and stained with HSBXB (magenta) and Bcl-xL (Alexa 488), which shows that the HSBXB was able to detect the heterodimer. (FIG. 4D)

After being incubated at 4° C. for 30 minutes, the cell antibody mixture was washed with FACS buffer and centrifuged at 0.3×g for 5 minutes to precipitate cells. Cells obtained from cell lines were resuspended in 150 μl of FACS buffer and analyzed by FACScan (Becton Dickinson, Mountain View, Calif.), with flow cytometry parameters predetermined using control cell samples as a negative control sample and anti-Bcl-xL-Rhodamine labeled mitochondria as a positive control. The mitochondrial suspension was loaded into the flow cytometry apparatus using a FACS tube and signals released from HSBXB FITC and Rhodamine were detected. If the mitochondrial suspension was double positive for both FITC and Rhodamine, it indicated that the test antibody was capable of binding to the Bcl-xL:Bim heterodimer. See FIG. 13A.

Example 6: Detecting Bcl-xL Bim Heterodimers in Fixed Cells

In this study, cells were characterized for having a prevalent Mcl-1/Bim or Bcl-xL/Bim heterodimer. The cells were placed on cover slips, and were then fixed with 2-4% formaldehyde (Formaldehyde, 16%, methanol free, Polysciences, Inc.) in PBS for 15 minutes at room temperature.

The cell-containing cover slips were then rinsed with PBS three times for 5 minutes each. The slips were then soaked in a blocking buffer (TBST/5% normal goat serum: to 5 ml ix TBST add 250 μl normal goat serum) for 60 minutes. After the blocking buffer was aspirated, an antibody (i.e., HSBXB, see FIG. 5) specific to either Mcl-1/Bim or Bcl-xL/Bim heterodimer was added to the slips. An anti-human VDAC-1 antibody was also added to localize mitochondria. After incubating the samples at 4° C. overnight, the slips were rinsed for 5 minutes three times with PBS. A fluorochrome-conjugated secondary antibody, diluted in a dilution buffer, was then added. After being incubated for 1-2 hours at room temperature in dark, the slips were rinsed with PBS three times for 2 minutes, and subsequently treated with Prolong Gold Antifade Reagent (Invitrogen, San Diego, Calif.). The slips were then sealed by painting nail polish around the edges of the slips, and the slips were then observed under an inverted fluorescent microscope. Localization of the antibody on mitochondria indicated that the antibody recognized the Mcl-1/Bim heterodimer or Bcl-xL/Bim heterodimer.

Example 7: Comparison of the Bcl-xL Bim Heterodimer Signal with HSBXB to Mitochondrial Profiling Readouts on Patient Samples and Comparison to Clinical Response Prior studies have demonstrated that Bcl-xL dependency, determined by the Hrk peptide readout in the mitochondrial priming assay, correlated to CLL patient response to the CDK-9 inhibitor Alvocidib. (See e.g., PCT Publication WO/2016/115105, Context dependent diagnostics test for guiding cancer treatment, incorporated herein by reference) In that study, the association of priming with patient response was highly significant, with an area under the curve (AUC)=0.83. In mitochondrial profiling, the Hrk priming signal is measured as a function of the positive signal, and complete depolarization of the mitochondria is induced by the chemical inhibitor carbonyl cyanide m-chlorophenylhydrazone (CCCP), while the negative signal is from DMSO treatment as outlined in following formula to obtain a "priming index".

$$\%\ Hrk\ \text{Priming} = \left[1 - \left(\frac{Hrk\ \text{peptide} - CCCP}{DMSO - CCCP}\right)\right] \times 100\%.$$

The HSBXB ELISA signals can be benchmarked from those same samples against the Hrk priming signal obtained and recorded earlier. The total Bcl-xL signal (bound and unbound) can then be determined. The Bcl-xL capture molecule and the second, non-interfering Bcl-Xl detection antibody can be used for this purpose. The HSBXB ELISA signal can be related to the total Bcl-xL ELISA as a maximum (100%) and the background signal as zero. The formula below can be used to calculate a percentage occupancy of Bcl-xL by Bim, the Bcl-xL/Bim priming index:

$$\%\ HSBXB\ \text{determined}\ Bcl\text{-}xL/BIM\ \text{priming} = \left[1 - \left(\frac{HSBXB - \text{total}\ Bcl\text{-}xl}{\text{no primary control} - \text{total}\ Bcl\text{-}xl}\right)\right] \times 100\%$$

The association between the biomarker status (percentage Bcl-xL/Bim priming) and patient responder or non-responder classification can be explored. The system can be optimized using cell lines, including responder and non-responder to ABT-263. Following that, fresh frozen needle biopsied breast cancer tumor tissue (archived) can be obtained from I-Specimen, Lexington, MA. The clinical response and outcome data from tissue donors are available through the provider. Up to 40 such specimens can be obtained and ran through the ELISA.

For analysis: Univariate comparisons can be made using log-rank (Mann-Whitney) and t-tests; and all p values can be calculated using two-sided alternative hypotheses. The p-values can be adjusted to account for multiple comparisons (ratio of 2 biomarkers) by accounting for the false discovery rate using the Benjamini Hochberg method. The predictive ability of the marker can be assessed using the receiver operating characteristic (ROC) area under the curve (AUC) statistic to identify the ideal thresholds. Multivariate analysis can be performed using logistic regression, and significant adjustment variables can include disease stage, age, hormone receptor (PR/ER) status, and cytogenetic risk status. Overall survival (OS) and event-free survival (EFS) can be tested for significant correlation with percentage priming by log-rank test (Mantel-Haenszel) for trend analysis.

The immunohistochemistry (IHC) method can be used to optimize HSBXB in breast cancer solid tumor biopsies, as well as to establish biomarker to clinical outcome. Some of the IHC work can be performed using digital pathology with an algorithm-based IHC signal quantification. The protocols of the present disclosure include various applications of enzymatic, chemical, temperature, and pressure treatment conditions that can enhance epitope detection signals.

IHC assay development is shown in FIG. 24A, FIG. 24B, FIG. 24C, FIG. 25, FIG. 26, FIG. 27, FIG. 28, FIG. 30, FIG. 31, and FIG. 32. An immunoblot of Bcl-xL expression in MEF Bcl-$xL^{-/-}$ cells is shown in FIG. 24A, and IF images and signal intensity of Bcl-xL and HSBXB are shown in FIG. 24B and FIG. 24C. In FIG. 25, an IHC assay is shown of the HSBXB antibody in MEF wildtype and MEF Bcl-$xL^{-/-}$ cells. In FIG. 26, an IHC assay of the HSBXB antibody is shown using HCC1937 human breast cancer cells for untreated (left), treated with the A-1331852 inhibitor (middle), and siRNA-Bcl-xL treated (right). In FIG. 27, an IHC assay of Bcl-xL inhibitor is shown for MEF wild-type (left) and MEF Bcl-$xL^{-/-}$ cells (right). In FIG. 28, an IHC assay of Bcl-xL inhibitor is shown for HCC1937 human breast cancer cells for untreated (left), and siRNA-Bcl-xL treated (right). FIG. 30 shows an IHC assay of HSBxB/BCLxL for MEF wild-type (left) and MEF Bcl-$xL^{-/-}$ cells (right). FIG. 31 shows an IHC assay of HSBxB/BCLxL using HCC1937 human breast cancer cells for untreated (left), A-1331852 treated (middle), and siRNA-Bcl-xL treated (right). FIG. 32 shows an IHC assay of HSBxB/BCLxL for BCL-xL:BIM in SVEC cells that are $BCLxL^{+/+}$.

Initial data indicated that the HSBXB antibody performed well in the formaldehyde fixed and paraffin (FFPE) IHC experiments (see e.g., FIG. 6), and FFPE triple negative breast cancer sections using IHC (FIG. 33A, FIG. 33B, FIG. 33C, FIG. 35A, FIG. 35B, and FIG. 35C). FIG. 35A, FIG. 35B, and FIG. 35C show the results of a two-color IHC on FFPE breast cancer cells. The results show the changing of the HSBXB/anti-Bcl-xL signal in Bcl-xL specific BH3 mimetic treated cells. The signal to noise index of the HSBXB antibody may be improved by exploring additional post-fixation preparation of human breast cancer xenograft FFPE samples and benchmark the results against ELISA and flow cytometry readouts in matched fresh frozen tissue obtained from I-Specimen, Lexington, MA, USA, as well as matched FFPE and pre-fixed human/mouse xenograft biopsies.

The experiments of this example demonstrate, inter alia, that there is a broad spectrum of application for the IHC, as HSBXB was observed to bind across several tissue derived cancers (FIG. 34).

IHC staining conditions can be optimized, and the sensitivity and specificity for detecting the heterodimer and the monomer can be carried out in sections of FFPE tissue. Cutoff values can be determined by establishing Lowest Levels of Quantification (LLOQ) and Highest Levels of Quantification (HLOQ). Quantitation through image analysis and visual scoring can enable IHC interpretation to be reduced to single values of signal density and the distribution of signal within defined boundaries.

Example 8: Correlation of HSBXB Bcl-xL Signal to Clinical Response in Archived Patient Samples To demonstrate the correlation between HSBXB/Bcl-xl signal and clinical response in archived patient samples, about 50-75 archived Her2+ breast cancer tumor tissue can be collected from naïve pretreatment and refractory pretreatment patients (i.e., acquired from I-specimen, Lexington, MA). Needle biopsies can then be thin sectioned and dispersed in 8 replicates in a 96 well plate. Individual wells can then be exposed to the HSBXB antibody at relevant concentrations (i.e., 1, 2, 3, 4, 5, 6, 7, 8, 9, 10) as well as to the Bcl-xL antibody. The HSBXB/Bcl-xL signal can then be determined. Data can be correlated to clinical response data (Herceptin, Lapatinib with or without PI3Kinase delta treatment).

Next, the experiments of this example demonstrate, inter alia, how to establish conditions for measuring HSBXB and Bcl-xL1 signal by Immunofluorescence (IF) microscopy. This can be carried out using a standard imaging system and microscope. In the case of fixed tissue, there is no reason to provoke or deplete the Bcl-xL/BIM heterodimer formation, or priming. Instead one can rely on the signal generated by the Bcl-xL antibody as internal maximum signal attainable. For the fixed breast cancer cells, this can be calculated using the median signal intensity for the anti-Bcl-xL IgG intracellular binding. For calculation of HSBXB determined priming, the following formula can be utilized:

$$\%\ HSBXB\ \text{determined}\ Bcl\text{-}xL/BIM\ \text{priming} = \left[1 - \left(\frac{\text{signal}\ Bcl\text{-}xl}{\text{signal}\ HXBSB}\right)\right] \times 100\%$$

Upon establishing imaging methods, up to 50-75 archived Her2+patient tumor biopsy samples that are paraffin embedded thin sections on slides (purchased from I-Specimen) can be examined using fluorescence microscopy. The signal specimens are each HER2+ and have clinical response, clinical outcome, as well as prognostic marker annotation. This analysis can be carried out using Quantitative IF microscopy, and can be used to measure the staining intensity of HSBXB as well as anti-Bcl-xL on a per cell basis and at the mitochondria, in the cytosol, or on the microtubules. These measurements can be compared to signals from adjacent, non-tumor tissue. Signals can then be reported per whole cell or specific subcellular region and compared to the same for each specimen. A skilled pathologist can use histological variation within tumors and can measure Bcl-2 and Mcl-1 expression levels in replicate slides. These additional measurements can be considered for inclusion in the correlation analysis.

The Biomarker can then be analyzed by statistical analysis by testing the association between the biomarker status (percentage Bcl-xL priming) and patient responder or non-responder classification. Univariate comparisons can be made using the Mann-Whitney test; and all reported P values can be two sided. The threshold for significance for the primary analysis to account for multiple comparisons (ratio of 2 biomarkers) can then be determined. The predictive ability of markers can be assessed using the area under the curve (AUC) statistic. Multivariate analysis can be performed using logistic regression and significant adjustment variables may include, disease stage, age, hormone receptor (e.g. PR, ER) status, and cytogenetic risk status. Overall survival (OS) and event-free survival (EFS) can then be tested for significant correlation and trends with percentage priming by a log-rank test.

In order to prepare Mcl-1/Bim (HSMCB) and Bcl-2/Bim (HSBLB) specific monoclonal Abs, and validate as mitochondrial priming detectors, one may expand the range of Bcl-2 family heterodimer specific antibodies (HSA) to Mcl-1 and Bcl-2. To this end, purified Mcl-1-GST, and Bcl2-GST fusion proteins can be covalently conjugated with Bim-modified-BH3 peptides. Monoclonal antibodies can be prepared and screened by Abpro (Lexington, MA). The readout fidelity and utility of the biomarker function in detecting mitochondrial priming can be established in cell lines. For hybridoma creation, Five Swiss Webster mice can be immunized with 50 micrograms of antigen in combination with Complete Freund's adjuvant for each target antigen. Antibodies can be made as previously described above.

The stained chips can then be dehydrated by incubation sequentially in 95% ethanol two times, 10 seconds each, in 100% ethanol two times, 10 seconds each, and finally in xylene two times, 10 seconds each. The chips can then be mounted with cover slips and examined using Fluorescence and UV microscopy for staining patterns. The staining patterns obtained from cancer tissue samples can then be compared with those obtained from adjacent normal tissues. (See, e.g. FIG. 6)

Figure 9B:
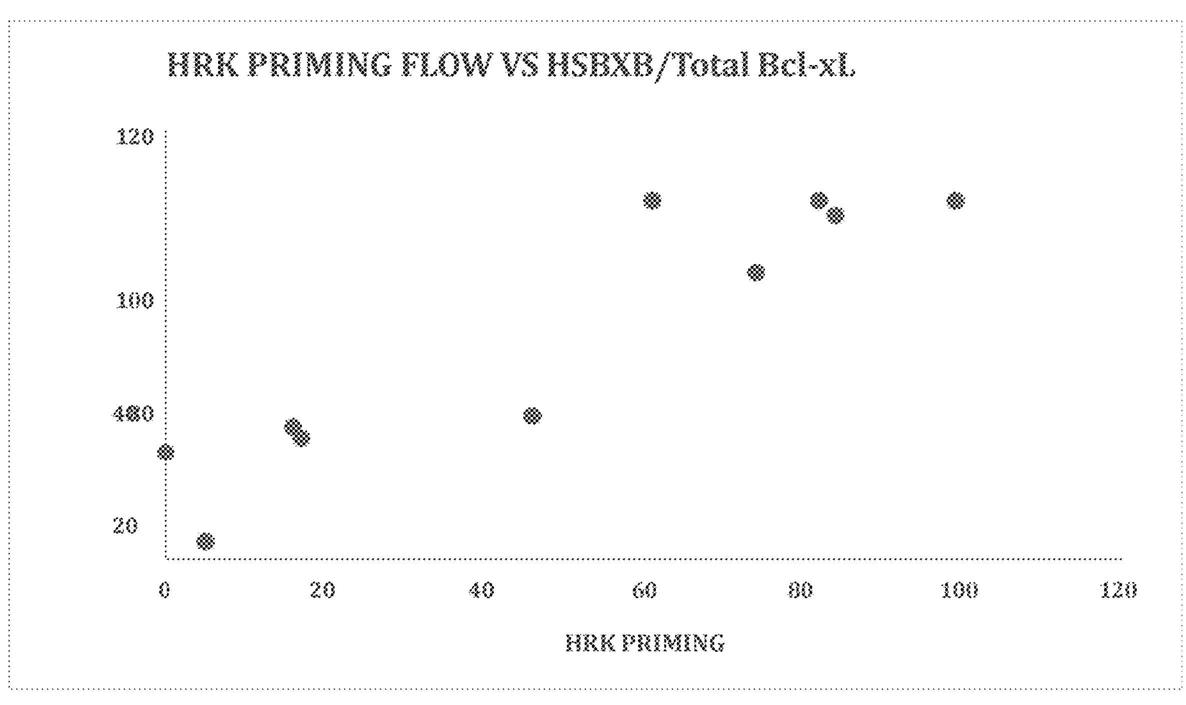
Figures 10A, 10B, 10C:
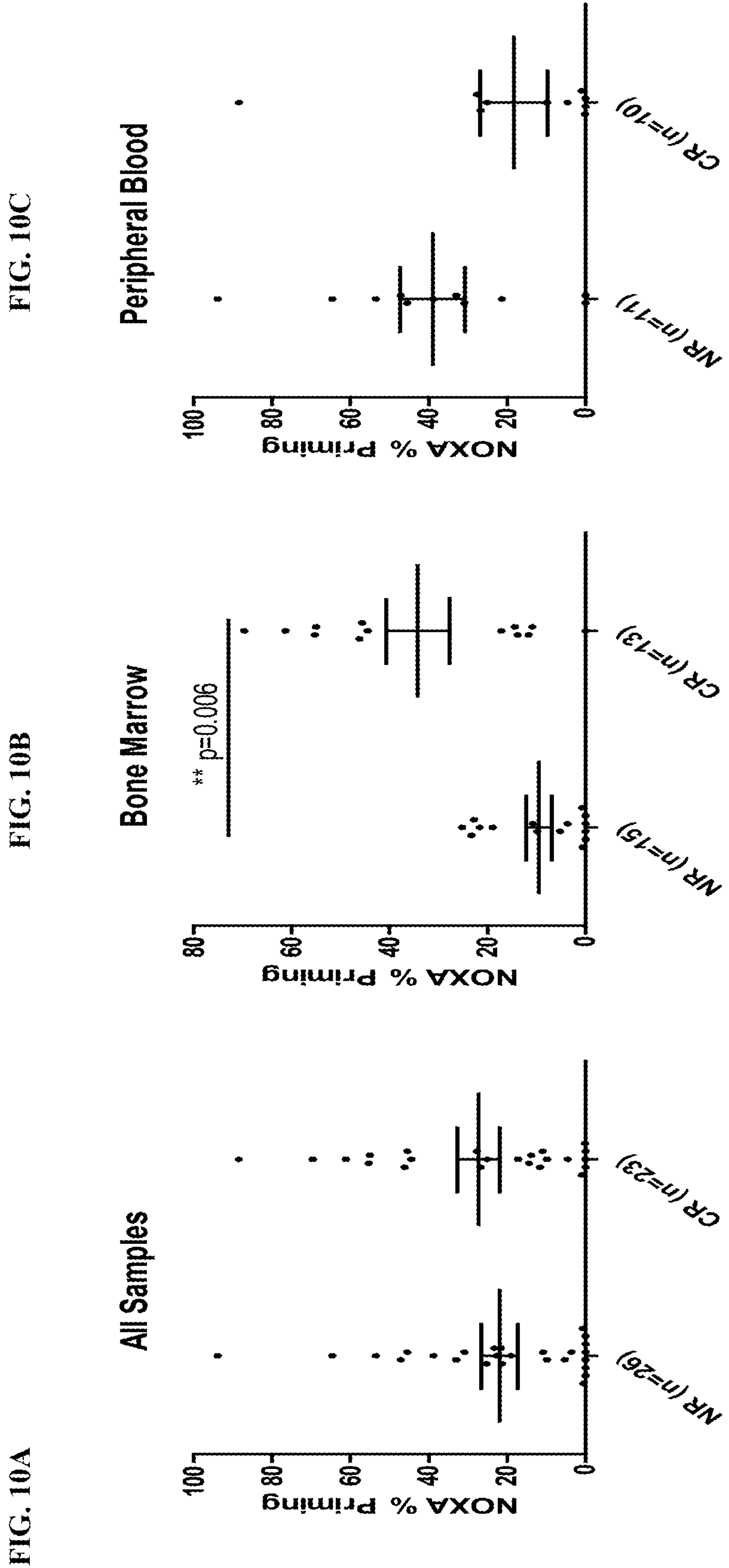
FIG. 10A, FIG. 10B, and FIG. 10C show the context dependent readout for all samples (FIG. 10A), bone marrow (FIG. 10B), and peripheral blood (FIG. 10C).
Figure 11C:
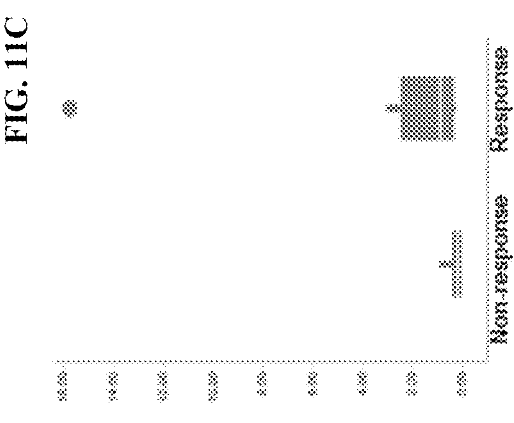
FIG. 11A, FIG. 11B, and FIG. 11C show the context specific Bcl-2, Bcl-xL dependencies in the peripheral blood (PB) or bone marrow (BM) as it relates to FLAM sensitivity.
Figure 11B:
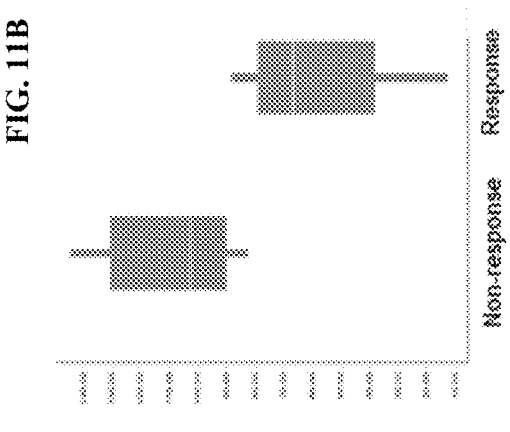
Figure 11A:
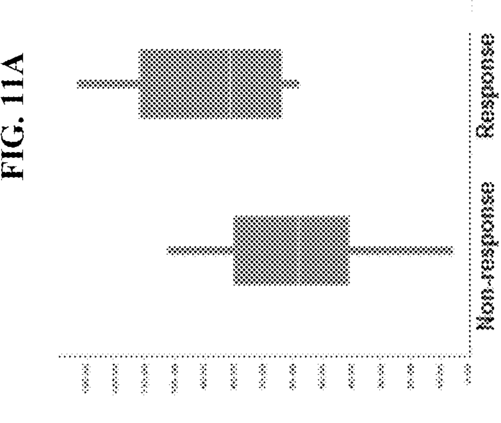
Figure 12C:
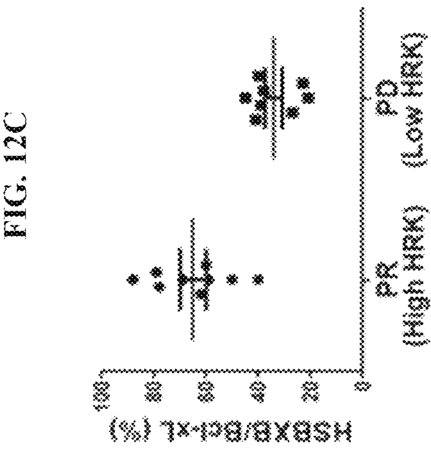
FIG. 12A, FIG. 12B, and FIG. 12C are graphs showing how the HSBXB antibody correlates to HRK and patient response.
Figure 12B:
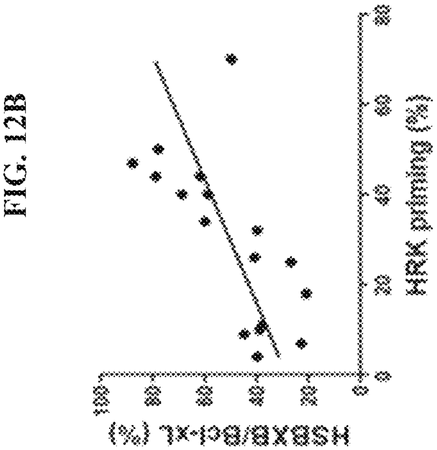
Figure 12A:
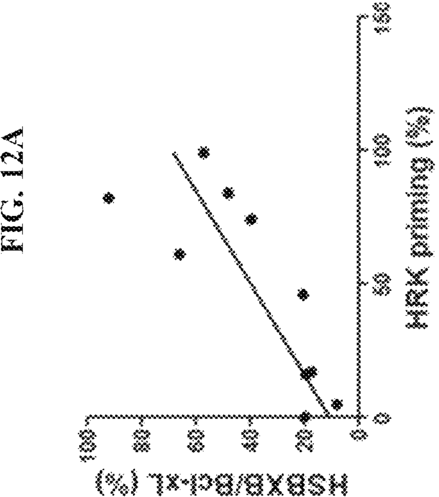

Example 9: Bcl-xL Bim Heterodimer Signal Correlates to Hrk Priming on Gated Blast Cell Population from AML Patient Samples. Predicate Readout Guides Biomarker Development AML patient samples were BH3 profiled in the experiments of this example. The Blast cell population showed Hrk priming, as well as response to the Hrk BH3 peptide that is selective for Bcl-xL. In parallel, AML patient samples were fixed and stained with the FITC labeled HSBXB antibody and the Rhodamine labeled Bcl-xL antibody. The Blast cell gated signal was resolved on FACS. HSBXB generated Bcl-xL/Bim Heterodimer readout to Total Bcl-xL signal ratio is plotted against the Hrk peptide generated signal from AML patient samples. See FIG. 9A, FIG, FIG. 9B. Also see FIG. 12A, FIG. 12B, and FIG. 12C which shows that the HSBXB signal correlates to HRK and patent response in both AML patient samples (FIG. 12A) and CLL patient samples (FIG. 12B). Pretreatment HRK signals of this patient group, were shown to associate with alvocidib treatment (FIG. 12C). Also, see FIG. 15A, FIG. 15B, and FIG. 15C, which show the correlation of percent HRK versus HSBXB/BCLXL in AML patient samples.

Example 10: Profiling Bcl-2 Heterodimers in Tumor Cell Lines Following Treatment with Bcl-xL Targeted BH3 Mimetic Compound The experiments of this example demonstrated a surprise result in that the HSBXB antibody was shown to function as a pharmacodynamic marker, detecting the shift in the Bcl-xL/Bim heterodimer as a result of treatment with Bcl-Xl selective BH3 mimetic A1155463. In these experiments, Bcl-xL expressing ATH66 cells were treated with the compound for 16 hours, then fixed with paraformaldehyde, permeabilized with non-ionic detergent and stained with HSBXB-FITC and with anti-Bcl-xL-Rhodamine. The signals were resolved using flow cytometry. The ratio of the signals provided the Bcl-xL priming index. This was observed to diminish over a time course that coincided with the occurrence of apoptosis, which was determined by DAPI staining and Annexin 5 surface staining. For example, see FIG. 8, and FIG. 14A, FIG. 14B, and FIG. 14C, which show that the HSBXB signal shifts in response to a Bcl-xL selective BH3 mimetic when treated with A-1155463.

Example 11: Immunofluorescence (IF) Stainings of the HSBXB Antibody, Changes in Localization of HSBXB, and Si-RNA Knockdown of Bcl-xL in Human Breast Cancer Cells Drug response to the Bcl-xL inhibitor, A-1331852, or the MEK inhibitor, Selumetinib, was compared in two types of human breast cancer cells, HCC1937 and BT-474, as shown in FIG. 16A and FIG. 16B. In both cell types, addition of the A-1331852 inhibitor resulted in a decrease in cell viability, while the MEK inhibitor did not decrease cell viability in either breast cancer cell type. Immunofluorescence (IF) stainings of the HSBXB antibody and the Bcl-XL inhibitor, A-1331852, are shown in FIG. 17 in untreated human breast cancer cells, HCC1937 and BT-474. IF stainings and relative signal intensity were obtained from human breast cancer cells, HCC1937, treated with or without the A-1331852 inhibitor, or treated with or without the HSBXB antibody, as shown in FIG. 18. The HSBXB antibody had a lower signal intensity in the inhibitor treated and control samples. Changes in the localization of Bcl-xL and HSBXB in response to the A-1331852 inhibitor were observed in HCC1937 cells (FIG. 19). In FIG. 23, an IF images are shown that demonstrate both Bcl-xL and HSBXB are observed in SVEC wild type cells and mitochondrial-primed SVEC cells.

Using siRNA, Bcl-xL-siRNA was transfected into the HCC1937 cells and Bcl-xL was knocked down, which resulted in a lower signal intensity of both Bcl-xL and HSBXB (FIG. 20, FIG. 22), and a reduced percentage of total positivity for both HSBXB (FIG. 29A) and BCLxL (FIG. 29B). The knock down of Bcl-xL in the HCC1937 cells was confirmed by IF staining, as no HSBXB was observed in the siRNA treated cells (FIG. 21).

Example 12: A Method for Predicting Cancer Patient Response to Immuno-Oncology Therapy by Assessing the Apoptotic Potential of the Infiltrating Lymphocytes in Solid Tumors by Measuring the Bcl-2 Family Heterodimers Relative to the Unbound Bcl-2 Family Proteins by In Situ IHC Apoptosis plays an important role in T cell immunity by the controlled elimination of cells during selection, including in tumors where these cells infiltrate and effect immune response against the tumor cells. The efficacy of PD-1/L1 blocking antibodies, for instance, is contingent on the presence of tumor-specific PD-1+ T cells being negatively regulated by PD-L1 expressing cells in the tumor, as well as the longevity of these cells. (Kuhnger, M. et. A., ASCO Journal Jun. 12, 2017 from 162.234.150.177) The goal of these treatments is to impact tumor immunity by interrupting a functionally intact PD-1/PD-L1 complexes with monoclonal antibodies. This enables T cells to mediate cancer cell killing. The PD-L1 expression level, location in the tumor, and longevity each impact the efficacy of this therapeutic strategy. Accurate information regarding the predisposition of infiltrating lymphocytes to respond to PDL-1 modulating therapies or other immune-oncology therapies is important in guiding use of these drugs.

The experiments of this example are guided by the understanding of the adaptive immune system mechanism for impacting immune oncology for therapeutic response. It has been observed that T cell responses for tumor antigens occurs via signaling cues from surrounding lymphocytes, for instance Myeloid derived suppressor cells, and Regulatory T cells (Wensveen, 1 Klaas P. J. M. van Gisbergen, I et al Immunity 32, 754-765, Jun. 25, 2010; Carrington, E N et al PNAS|Mar. 31, 2015|vol. 112|no. 13). The Bcl-2 family heterodimer state impacts this signaling and provides a metric for anticipating successful enhancement of immune response directed against tumor cells.

In one embodiment, the propensity for T cell longevity and activation can be assessed by examining the pro-apoptotic molecule Noxa bound to the antagonist Mcl-1. In addition, the propensity for T cell longevity and activation can be assessed by measuring the Bim/Mcl-1 heterodimer in situ using IHC on FFPE non-small cell lung patient biopsied tissue. The results may align with a correlation as suggested in the literature where this mechanism of modulating T-cell population in innate immunity has been described. (i.e., Wensveen, Klaas P. J. M. van Gisbergen, et al Immunity 32, 754-765, Jun. 25, 2010). Measuring the Mcl-1/Bim heterodimer in the infiltrating T-cell populations can provide a metric for predicting the responsiveness of PDL-1 targeted drugs as well as other immune oncology modulating therapies.

Example 13: A Method for Generating Heterodimer Antibodies

Disclosed herein is a method of isolating, selecting, and purifying a heterodimer antibody (e.g., a Mcl-1/Bim-BH3 heterodimer antibody) from an immunized mouse. The isolation, selection, and purification of a heterodimeric antibody allows for an investigation of the functionality of the heterodimer, such as determining the priming state of a cancer cell, and detecting whether a patient is sensitive to a cancer treatment including with immune modulating drugs. The purified heterodimeric antibodies produced by the methods disclosed herein can be used to detect a heterodimer comprising two B-cell lymphoma 2 (BCL-2) proteins in a solid tumor sample from a patient or a liquid tumor from a patient.

As shown schematically in FIG. 36, a mouse is initially immunized with a covalent heterodimer antigen (e.g., a Mcl-1/Bim-BH3). A whole cell enzyme-linked immunosorbent assay (ELISA) can be used to test for the presence of the antigen-specific antibody in the immunized mouse serum as well as analyze the antibody titer. Repeated boosters can be performed to increase the antibody titer. An increase in titer is typically observed with each repeated booster. Once a sufficient titer has been achieved (e.g., serum dilutions of up to 1:150,000), the spleen of the mouse is harvested, and the splenic B cells containing the heterodimer are then selected using two affinity-based selection steps: first, the splenic B cells are passed through a magnetic column for negative selection, and then the splenic B cells are passed through a positively charged magnetic column selection. To perform the negative magnetic column-based selection, the splenic B cells are placed onto a negatively charged column that has been coated with both glutathione-derivatized magnetic-beads and a recombinant fusion protein containing one monomer of the heterodimer fused to GST (e.g., a Mcl-1GST). The flow through from the magnetic column for negative selection is then collected, which represents the splenic B cells that did not bind to the monomeric recombinant fusion protein, and thus do not contain the heterodimer. This flow-through containing the B cells from the magnetic column for negative selection is then passed onto a second magnetic column that has been positively coated with the covalent heterodimer antigen (e.g., a Mcl-1/Bim-BH3) for positive affinity selection. Cells containing heterodimer-specific antibodies are bound to the magnetic column for positive selection, and then eluted and collected from the positive selection column. The selected cells containing the heterodimer antibodies can then be grown in media with supplements for B cell growth (e.g., IL-4, LPS, and CD40-ligand). Cells can then be isolated and sub-cloned by standard and routine molecular biology methods, and the supernatants can then be screened (e.g., by an ELISA) for antibodies that have superior heterodimer-specific binding and production.

At this stage of the method, the complete sequence of the antibody (e.g., Ig heavy and light chains) that demonstrates the optimal screening signal (e.g., based on an ELISA) from the supernatants can be identified. For example, the full length of the antibody can be determined using the 5' or 3' Race System (i.e., RACE PCR) for rapid amplification of cDNA ends. In these experiments of the method, standard internal primers from the variable region of the mouse heavy and light chain can be used to generate the full length sequence.

Once the optimum heterodimer antibody has been isolated and selected, standard and routine molecular biology methods can be used to clone the isolated heterodimer antibody into an expression vector and expression system (e.g., 293T cells) for purification and large-scale antibody production. The specific binding of the antibody can then be tested in a control assay. For example, a control assay can be an ELISA where the plate has been coated with both the heterodimer antigen (e.g., Mcl-1/Bim, positive) and monomer antigen (e.g., Mcl-1, negative). In some embodiments, the control assay is an immunofluorescence (IF) staining using a cell line that expresses both proteins of the heterodimer (e.g., Mcl-1 and Bim). For example, the IF staining of a Mcl-1/Bim heterodimer in a cell that expresses both proteins of the Mcl-1/Bim heterodimer can be compared to the IF staining of a Mcl-1/Bim heterodimer in a different cell that does not express both proteins of the Mcl-1/Bim heterodimer (i.e., the proteins can be knocked down as a control). In some embodiments, the control assay comprises immunohistochemistry (IHC) staining of a cell line that expresses both proteins of the heterodimer (e.g., Mcl-1 and Bim), compared to an IHC staining of a cell line that does not express both proteins of the heterodimer. In some embodiments, the control assay comprises IHC staining on Formalin-Fixed Paraffin-Embedded (FFPE) blocks, which can be derived from a cell line, a control cell line, xenograft tissue, and patient tissue. In some embodiments, the control assay comprises flow cytometry.

One example of these methods related to isolating, selecting, and purifying a heterodimer antibody is shown in FIG. 37, FIG. 38, and FIG. 39. The data in FIG. 37 shows the selective binding of IgG clone 9E05 to the Mcl-1/Bim heterodimer. This clone was produced using the methods disclosed herein. Purified supernatant from clone 9E05 was titrated using the affinity selection described above, i.e., glutathione-derivatized magnetic-beads (negative selection), and a recombinant fusion protein containing one monomer of the heterodimer fused to GST (e.g., a Mcl-1GST), and beads coated with Mcl-1-GST/Bim BH3 (positive selection); the clone was then further resolved using ELISA screening and routine cloning to yield a highly pure heterodimeric antibody, as shown in FIG. 37. The data in FIG. 38 shows the selective binding of the 9E05 clone to the modified BPA4 peptide, which is present in the formation of the Mcl-1/Bim heterodimer. Plates were coated with either the Mcl-1/Bim heterodimer, Mcl-1 monomer, or BPA4 peptide alone. The data in FIG. 39 shows the selective binding of the 9E05 clone to the modified BPA4 peptide, which is present in the formation of the Mcl-1/Bim heterodimer. Plates were coated with either the Mcl-1/Bim heterodimer with modified BPA peptides, native Bim biotin, or truncated Bim peptide. FIG. 40 is an IF image showing Mcl-1/Bim heterodimer specific for clone E905 and Mcl-1 polyclonal rabbit antibody. FIG. 41 is an IF image showing Mcl-1/Bim heterodimer specific for clone E905 and Mcl-1 polyclonal rabbit antibody. FIG. 42 is an IF image showing Mcl-1 monomer specific for clone 15D02 and Mcl-1 polyclonal rabbit antibody. FIG. 43 is an IF image showing that the Mcl-1/Bim heterodimer antibody (HSMCB), requires Bim to bind in situ.

In some embodiments, the methods of the present disclosure related to isolating, selecting, and purifying a heterodimer antibody (e.g., a Mcl-1/Bim-BH3 heterodimer antibody) from an immunized mouse can be modified. For example, when the cells containing heterodimer-specific antibodies are eluted and collected from the positive selection column, as described above, the eluted cells containing heterodimer-specific antibodies can be fluorescently labelled (e.g., a fluorescent dye, tag, probe), followed by the culturing of the cells. In some embodiments, the cells are labelled with covalent Mcl-1-GST/Bim BH3-FITC. The labelled cells can then be sorted, for example, by Flow Cytometry and those cells displaying the optimum signal can be gated on the Flow Cytometer and isolated. This step can then be repeated (i.e., culturing of isolated cells from Flow Cytometer, followed by another round of Flow Cytometry), and cells displaying the optimum binding characteristics can be further cloned as described above.

All of the features disclosed herein may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method for predicting a patient's sensitivity to a cancer treatment, comprising:

(a) contacting a sample with an antibody or antibody format that recognizes a heterodimer comprising two B-cell lymphoma 2 (BCL-2) proteins, wherein the antibody or antibody format comprises:

(i) a heavy chain variable region comprising heavy chain CDR1, CDR2, and CDR3 sequences, wherein the heavy chain CDR1 sequence is GHTFTEHYIN (SEQ ID NO: 1), the heavy chain CDR2 sequence is WIFPGSGSTYYNEKFKG (SEQ ID NO: 2); and the heavy chain CDR3 sequence is SYSNFWFAY (SEQ ID NO: 3); and (ii) a light chain variable region comprising light chain CDR1, CDR2, and CDR3 sequences, wherein the light chain CDR1 sequence is RASQSIGTSIH (SEQ ID NO: 4), the light chain CDR2 sequence is KYASESIS (SEQ ID NO: 5), and the light chain CDR3 sequence is QQSNSWPTT (SEQ ID NO: 6), the sample being a specimen from a solid tumor of the patient;

(b) detecting a signal that indicates the amount of the heterodimer (c) determining a ratio of the amount of heterodimer present in the sample from step (b) to a reference value, wherein the reference value comprises the amount of one of the BCL-2 protein monomers of the heterodimer in the sample, and (d) determining a correlation between the ratio of the amount of heterodimer in the sample to the amount of one of the BCL-2 protein monomers of the heterodimer in the sample, the ratio being predictive of the patient's sensitivity to the cancer treatment.

2. The method of claim 1, further comprising administering a cancer treatment to the patient if the ratio is predictive of sensitivity to the cancer treatment.

3. The method of claim 1, wherein the heterodimer comprises B-cell lymphoma extra large ("BCLXL") and BCL-2 Interacting Mediator of cell death ("BIM").

4. The method of claim 1, wherein the cancer treatment comprises a BH3 mimetic.

5. The method of claim 4, wherein the BH3 mimetic is selected from ABT-737 and ABT-263 (navitoclax), Venetoclax (Venclexta, ABT-199), S63845, AMG176, ADZ5991, A-1155463, A1331852, EU5346, or combinations thereof.

6. The method of claim 1, wherein the cancer treatment comprises a checkpoint inhibitor.

7. The method of claim 6, wherein the checkpoint inhibitor is an agent that targets one of T Cell Immunoglobulin and Mucin Domain-3 ("TIM-3"), B and T Lymphocyte Attenuator ("BTLA"), Programmed Cell Death Protein 1 ("PD-1"), Cytotoxic T Lymphocyte Antigen 4 ("CTLA-4"), B7 Homolog 4 ("B7-H4"), Glucocorticoid-Induced TNFR-Related Protein ("GITR"), galectin-9, Herpesvirus Entry Mediator ("HVEM"), Programmed Death-Ligand 1 ("PD-L1"), Programmed Death-Ligand 2 ("PD-L2"), B7 Homolog 3 ("B7-H3"), Cluster of Differentiation 244 ("CD244"), Cluster of Differentiation 160 ("CD160"), T cell Immunoreceptor with Ig and ITIM Domains ("TIGIT"), Signal Regulatory Protein Alpha ("SIRPα"), Inducible T-cell COStimulator ("ICOS"), Cluster of Differentiation 172a ("CD172a"), and Transmembrane and Immunoglobulin Domain Containing 2 ("TMIGD2").

8. The method of claim 1, wherein the antibody or antibody format comprises:

(i) a heavy chain variable region sequence comprising an amino acid sequence having at least 95% identity with SEQ ID NO: 7; and (ii) a light chain variable region sequence comprising an amino acid sequence having at least 95% identity with SEQ ID NO: 8.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 1

Gly His Thr Phe Thr Glu His Tyr Ile Asn
1               5                   10


<210> SEQ ID NO 2
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 2

Trp Ile Phe Pro Gly Ser Gly Ser Thr Tyr Tyr Asn Glu Lys Phe Lys
1               5                   10                  15

Gly


<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 3

Ser Tyr Ser Asn Phe Trp Phe Ala Tyr
1               5


<210> SEQ ID NO 4
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 4

Arg Ala Ser Gln Ser Ile Gly Thr Ser Ile His
1               5                   10


<210> SEQ ID NO 5
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 5

Lys Tyr Ala Ser Glu Ser Ile Ser
1               5


<210> SEQ ID NO 6
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 6
```

```
Gln Gln Ser Asn Ser Trp Pro Thr Thr
1               5


<210> SEQ ID NO 7
<211> LENGTH: 211
<212> TYPE: PRT
<213> ORGANISM: Artificial Sequence
<220> FEATURE:
<223> OTHER INFORMATION: Synthetic Sequence

<400> SEQUENCE: 7

Gln Val Gln Leu Gln Gln Ser Gly Pro Glu Leu Val Lys Pro Gly Ala
1               5                   10                  15

Ser Val Lys Ile Ser Cys Lys Ala Ser Gly His Thr Phe Thr Glu His
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Tyr Asn Glu Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Ser Tyr Ser Asn Phe Trp Phe Ala Tyr Trp Gly Gln Gly Thr
            100                 105                 110

Leu Val Thr Val Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp
    210


<210> SEQ ID NO 8
<211> LENGTH: 214
<212> TYPE: PRT
<213> ORGANISM: Artificial Sequence
<220> FEATURE:
<223> OTHER INFORMATION: Synthetic Sequence

<400> SEQUENCE: 8

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80
```

```
Glu Asp Ile Ala Asp Tyr Tyr Cys Gln Gln Ser Asn Ser Trp Pro Thr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
    210


<210> SEQ ID NO 9
<211> LENGTH: 718
<212> TYPE: DNA
<213> ORGANISM: Artificial Sequence
<220> FEATURE:
<223> OTHER INFORMATION: Synthetic Sequence

<400> SEQUENCE: 9

tctagaatga agttgcctgt taggctgttg gtgctgatgt tctggattcc tgcttccttg      60

agcgacatct tgctgactca gtctccagcc atcctgtctg tgagtccagg agaaagagtc     120

agtttctcct gcagggccag tcagagcatt ggcacaagca tacactggta tcagcaaaga     180

acaaatggtt ctccaaggct tctcataaag tatgcttctg agtctatctc tggcatccct     240

tccaggttta gtggcagtgg atcagggaca gattttactc ttagcatcaa cagtgtggag     300

tctgaggata ttgcagatta ttactgtcaa caaagtaata gctggccaac cacgttcgga     360

ggggggacca agctggaaat aaaacgggct gatgctgcac caactgtatc catcttccca     420

ccatccagtg agcagttaac atctggaggt gcctcagtcg tgtgcttctt gaacaacttc     480

taccccaaag acatcaatgt caagtggaag attgatggca gtgaacgaca aaatggcgtc     540

ctgaacagtt ggaccgatca ggacagcaaa gacagcacct acagcatgag cagcaccctc     600

acgttgacta aggacgagta tgaacgacat aacagctata cctgtgaggc cactcacaag     660

acatcaactt cacccattgt caagagcttc aacaggggag agtgttagca gcggccgc       718


<210> SEQ ID NO 10
<211> LENGTH: 233
<212> TYPE: PRT
<213> ORGANISM: Artificial Sequence
<220> FEATURE:
<223> OTHER INFORMATION: Synthetic Sequence

<400> SEQUENCE: 10

Met Lys Leu Pro Val Arg Leu Leu Val Leu Met Phe Trp Ile Pro Ala
1               5                   10                  15

Ser Leu Ser Asp Ile Leu Leu Thr Gln Ser Pro Ala Ile Leu Ser Val
            20                  25                  30

Ser Pro Gly Glu Arg Val Ser Phe Ser Cys Arg Ala Ser Gln Ser Ile
```

```
        35                  40                  45

Gly Thr Ser Ile His Trp Tyr Gln Gln Arg Thr Asn Gly Ser Pro Arg
    50                  55                  60

Leu Leu Ile Lys Tyr Ala Ser Glu Ser Ile Ser Gly Ile Pro Ser Arg
65                  70                  75                  80

Phe Ser Gly Ser Gly Ser Gly Thr Asp Phe Thr Leu Ser Ile Asn Ser
                85                  90                  95

Val Glu Ser Glu Asp Ile Ala Asp Tyr Tyr Cys Gln Gln Ser Asn Ser
            100                 105                 110

Trp Pro Thr Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Gly Glu Cys
225                 230


<210> SEQ ID NO 11
<211> LENGTH: 1344
<212> TYPE: DNA
<213> ORGANISM: Artificial Sequence
<220> FEATURE:
<223> OTHER INFORMATION: Synthetic Sequence

<400> SEQUENCE: 11

cttaagtcag gtccagctac agcagtctgg acctgagctg gtgaagcctg gggcttcagt      60

gaagatatcc tgcaaggctt ctggccacac cttcactgaa cactatataa attgggtgaa     120

gcagaggcct ggacagggac ttgagtggat tggatggatt tttcctggaa gtggtagtac     180

ttactacaat gagaagttca agggcaaggc cacacttact gtagacaaat cctccagcac     240

agcctacatg ttgctcagca gcctgacctc tgaggactct gcggtctatt tctgtgcaag     300

aagctatagt aacttctggt ttgcttactg gggccaaggg actctggtca ctgtctctgc     360

caaaacaaca gccccatcgg tctatccact ggcccctgtg tgtggagata caactggctc     420

ctcggtgact ctaggatgcc tggtcaaggg ttatttccct gagccagtga ccttgacctg     480

gaactctggc tccctgtcca gtggtgtgca caccttccca gcagtcctcc agtctgacct     540

ctacaccctc agcagctcag tgactgtaac ctccagcacc tggcccagcc agtccatcac     600

ctgcaatgtg gcccacccgg caagcagcac caaggtggac aagaaaattg agcccagagg     660

gcccacaatc aagccctgtc ctccatgcaa atgcccagca cctaacctct tgggtggacc     720

atccgtcttc atcttccctc caaagatcaa ggatgtactc atgatctccc tgagccccat     780

agtcacatgt gtggtggtgg ctgtgagcga ggatgaccca gatgtccaga tcagttggtt     840

tgtgaacaac gtggaagtac acacagctca gacacaaacc catagagagg attacaacag     900

tactctccgg gtggtcagtg ccctccccat ccagcaccag gactggatga gtggcaagga     960
```

```
gttcaaatgc aaggtcaaca acaaagacct cccagcgccc atcgagagaa ccatctcaaa   1020

acccaaaggg tcagtaagag ttccacaggt atatgtcttg cctccaccag aagaagagat   1080

gactaagaaa caggtcactc tgacctgcat ggtcacagac ttcatgcctg aagacattta   1140

cgtggagtgg accaacaacg ggaaaacaga gctaaactac aagaacactg aaccagtcct   1200

ggactctgat ggttcttact tcatgtacag caagctgaga gtggaaaaga agaactgggt   1260

ggaaagaaat agctactcct gttcagtggt ccacgagggt ctgcacaatc accacacgac   1320

taagagcttc tcccggaccc cggg                                          1344
```

```
<210> SEQ ID NO 12
<211> LENGTH: 365
<212> TYPE: PRT
<213> ORGANISM: Artificial Sequence
<220> FEATURE:
<223> OTHER INFORMATION: Synthetic Sequence

<400> SEQUENCE: 12

Met Leu Leu Ser Ser Leu Thr Ser Glu Asp Ser Ala Val Tyr Phe Cys
1               5                   10                  15

Ala Arg Ser Tyr Ser Asn Phe Trp Phe Ala Tyr Trp Gly Gln Gly Thr
            20                  25                  30

Leu Val Thr Val Ser Ala Lys Thr Thr Ala Pro Ser Val Tyr Pro Leu
        35                  40                  45

Ala Pro Val Cys Gly Asp Thr Thr Gly Ser Ser Val Thr Leu Gly Cys
    50                  55                  60

Leu Val Lys Gly Tyr Phe Pro Glu Pro Val Thr Leu Thr Trp Asn Ser
65                  70                  75                  80

Gly Ser Leu Ser Ser Gly Val His Thr Phe Pro Ala Val Leu Gln Ser
                85                  90                  95

Asp Leu Tyr Thr Leu Ser Ser Ser Val Thr Val Thr Ser Ser Thr Trp
            100                 105                 110

Pro Ser Gln Ser Ile Thr Cys Asn Val Ala His Pro Ala Ser Ser Thr
        115                 120                 125

Lys Val Asp Lys Lys Ile Glu Pro Arg Gly Pro Thr Ile Lys Pro Cys
    130                 135                 140

Pro Pro Cys Lys Cys Pro Ala Pro Asn Leu Leu Gly Gly Pro Ser Val
145                 150                 155                 160

Phe Ile Phe Pro Pro Lys Ile Lys Asp Val Leu Met Ile Ser Leu Ser
                165                 170                 175

Pro Ile Val Thr Cys Val Val Val Ala Val Ser Glu Asp Asp Pro Asp
            180                 185                 190

Val Gln Ile Ser Trp Phe Val Asn Asn Val Glu Val His Thr Ala Gln
        195                 200                 205

Thr Gln Thr His Arg Glu Asp Tyr Asn Ser Thr Leu Arg Val Val Ser
    210                 215                 220

Ala Leu Pro Ile Gln His Gln Asp Trp Met Ser Gly Lys Glu Phe Lys
225                 230                 235                 240

Cys Lys Val Asn Asn Lys Asp Leu Pro Ala Pro Ile Glu Arg Thr Ile
                245                 250                 255

Ser Lys Pro Lys Gly Ser Val Arg Val Pro Gln Val Tyr Val Leu Pro
            260                 265                 270

Pro Pro Glu Glu Glu Met Thr Lys Lys Gln Val Thr Leu Thr Cys Met
        275                 280                 285
```

-continued

```
Val Thr Asp Phe Met Pro Glu Asp Ile Tyr Val Glu Trp Thr Asn Asn
    290                 295                 300

Gly Lys Thr Glu Leu Asn Tyr Lys Asn Thr Glu Pro Val Leu Asp Ser
305                 310                 315                 320

Asp Gly Ser Tyr Phe Met Tyr Ser Lys Leu Arg Val Glu Lys Lys Asn
                325                 330                 335

Trp Val Glu Arg Asn Ser Tyr Ser Cys Ser Val Val His Glu Gly Leu
            340                 345                 350

His Asn His His Thr Thr Lys Ser Phe Ser Arg Thr Pro
        355                 360                 365
```